US010481102B2

(12) United States Patent
Jeanne et al.

(10) Patent No.: US 10,481,102 B2
(45) Date of Patent: Nov. 19, 2019

(54) MULTI-AXIS POSITIONING DEVICE

(71) Applicant: NEWPORT CORPORATION, Irvine, CA (US)

(72) Inventors: Alain Jeanne, Amilly (FR); Stéphane Bailloux, Ferrieres (FR); Laurent Courtemanche, Chécy (FR)

(73) Assignee: NEWPORT CORPORATION, Irvine, CA (US)

( * ) Notice: Subject to any disclaimer, the term of this patent is extended or adjusted under 35 U.S.C. 154(b) by 0 days.

(21) Appl. No.: 16/053,711

(22) Filed: Aug. 2, 2018

(65) Prior Publication Data
US 2018/0340895 A1 Nov. 29, 2018

Related U.S. Application Data

(62) Division of application No. 15/320,718, filed as application No. PCT/US2014/045464 on Jul. 3, 2014, now Pat. No. 10,073,043.

(51) Int. Cl.
*G01N 21/95* (2006.01)
*H01L 21/66* (2006.01)
(Continued)

(52) U.S. Cl.
CPC ......... *G01N 21/8851* (2013.01); *G01B 11/26* (2013.01); *G01N 21/9501* (2013.01);
(Continued)

(58) Field of Classification Search
CPC ............ G01N 21/8851; G01N 21/9501; H01L 21/67288; H01L 22/12; H01L 21/68; G01B 11/26
See application file for complete search history.

(56) References Cited

U.S. PATENT DOCUMENTS 5,140,242 A 8/1992 Doran et al.
5,204,712 A 4/1993 Bouwer et al.
(Continued)

FOREIGN PATENT DOCUMENTS

KR 2013 0120971 11/2013
WO WO 16/003472 1/2016

OTHER PUBLICATIONS

International Preliminary Report on Patentability dated Jan. 12, 2017 in International Patent Application No. PCT/US2014/045464 filed: Jul. 3, 2014 and published as: WO/2016/003472 on: Jan. 7, 2016.

(Continued)

*Primary Examiner* — Sang H Nguyen
(74) *Attorney, Agent, or Firm* — Schmeiser, Olsen & Watts LLP

(57) ABSTRACT

A multi-axis positioning system that may be used in conjunction with an inspection system includes multiple position sensors corresponding to multiple axes in conjunction with multiple motors also corresponding to multiple axes to provide high accuracy, high load and extended travel for controllable movement of an object in up to 6 degrees of freedom. Some embodiments of the multi-axis positioning system may include an x-y stage assembly, a bottom plate assembly coupled to the x-y stage assembly, a top plate assembly coupled to the bottom plate assembly, and a chuck secured to the top plate assembly with multiple position sensors configured to measure displacement between the x-y stage assembly and top plate assembly.

19 Claims, 29 Drawing Sheets

(51) Int. Cl.
*H01L 21/68* (2006.01)
*G01B 11/26* (2006.01)
*G01N 21/88* (2006.01)
*H01L 21/67* (2006.01)

(52) U.S. Cl.
CPC ........ *H01L 21/67288* (2013.01); *H01L 21/68* (2013.01); *H01L 22/12* (2013.01)

(56) References Cited

U.S. PATENT DOCUMENTS

| | | | |
|---|---|---|---|
| 5,475,728 A | 12/1995 | Smith et al. | |
| 6,149,506 A * | 11/2000 | Duescher | B24B 1/00 |
| | | | 451/178 |
| 6,646,719 B2 | 11/2003 | Lee et al. | |
| 6,756,751 B2 | 6/2004 | Hunter | |
| 10,254,499 B1 * | 4/2019 | Cohen | G02B 6/4463 |
| 2003/0156270 A1 | 8/2003 | Hunter | |
| 2004/0080730 A1 | 4/2004 | Binnard | |
| 2004/0140780 A1 | 7/2004 | Cahill et al. | |
| 2005/0012920 A1 | 1/2005 | Jeanne et al. | |
| 2005/0045821 A1 * | 3/2005 | Noji | G01N 23/225 |
| | | | 250/311 |
| 2005/0134862 A1 | 6/2005 | Hill | |
| 2008/0180053 A1 * | 7/2008 | Lee | G03F 7/70716 |
| | | | 318/649 |
| 2008/0309276 A1 | 12/2008 | Xu | |
| 2010/0178044 A1 | 7/2010 | Ohno | |
| 2010/0280654 A1 | 11/2010 | Rice et al. | |
| 2010/0290138 A1 | 11/2010 | Thomas et al. | |
| 2014/0071580 A1 | 3/2014 | Higginson et al. | |
| 2015/0040711 A1 | 2/2015 | Kim et al. | |

OTHER PUBLICATIONS

International Search Report and Written Opinion dated Mar. 31, 2015 in International Patent Application No. PCT/US2014/045464 filed: Jul. 3, 2014 and published as: WO/2016/003472 on: Jan. 7, 2016.

Extended European Search Report dated Jan. 31, 2018 in European Application No. EP 14896890.2 filed: Jul. 3, 2014.

Office Action dated May 25, 2018 in U.S. Appl. No. 15/320,718, filed Dec. 20, 2016 and published as: 2017/0153186 on Jun. 1, 2017.

* cited by examiner

MULTI-AXIS POSITIONING DEVICE

RELATED PATENT APPLICATION(S)

This application is a divisional of U.S. patent application Ser. No. 15/320,718, filed Dec. 20, 2016, naming Alain Jeanne et al. as inventors, titled "Multi-Axis Positioning Device", which is a national stage application under 35 U.S.C. section 371 of International Patent Application No. PCT/US2014/045464, filed Jul. 3, 2014, naming Alain Jeanne et al. as inventors, titled "Multi-Axis Positioning Device", which are all incorporated by reference herein in their entirety.

BACKGROUND

Multi-axis positioning devices may be used for adjusting the height and parallelism of a sample such as a semiconductor wafer in a processing machine such as a semiconductor wafer inspection tool. Multi-axis positioning devices typically control positioning of Z-axis displacement, rotation about an X-axis, and rotation about a Y-axis while the semiconductor wafer is moving in the x-y directions under a semiconductor processing machine, such as an optical inspection system. The multi-axis positioning device may be used to dynamically compensate for non-flatness of the wafer and should be stiff to provide high bandwidth positioning.

Some multi-axis positioning devices that are currently available may have certain performance deficiencies. For example, some multi-axis positioning device designs are too complicated and may also increase a risk particulate contamination as a result of certain geometries. Some multi-axis positioning devices are configured such that it is difficult to maintain the co-location of a focal point in an x-y plane as the tip and tilt angles are adjusted. In addition, mechanically driven systems may be tool bulky in some instances. What have been needed are multi-axis positioning devices that are stable, rigid, minimize complexity and have a low mass in order to allow a high throughput. What has also been needed are multi-axis positioning devices that accurately measure the position of a sample being positioned so as to allow displacement along the various translational and rotational axes while maintaining a known position of the inspection location on the sample.

SUMMARY

Some embodiments of a multi-axis positioning system may include an x-y stage assembly including a base that may be secured to a stable surface and an upper stage of the x-y stage assembly. The x-y stage assembly may also include a first linear actuator that is configured to produce controllable displacement of the upper stage relative to the base along a first x-y stage axis, and a second linear actuator that is configured to produce controllable displacement of the upper stage relative to the base along a second x-y stage axis, the first x-y stage axis being substantially perpendicular to the second x-y stage axis. The upper stage of the x-y stage assembly may include an upper surface of the upper stage that includes a plurality of flat smooth active reference surfaces that are configured to slidingly receive a plurality of respective passive reference surfaces and that each include a pressurized gas port. The multi-axis positioning system may also include a bottom plate assembly having a bottom plate body and a plurality of passive reference surfaces which are secured to or otherwise disposed on the bottom plate body. In particular, the passive reference surfaces may be disposed on a bottom surface of the bottom plate body and positioned on an outer portion of the bottom plate body so as to be aligned with respective active reference surfaces of the x-y stage assembly. The bottom plate assembly may also have a plurality of resilient suspension members which are disposed on an outer portion of the bottom plate body and extending upward from a top portion of the bottom plate. The bottom plate assembly may also include at least one piezoelectric motor which is secured to the bottom plate body and including a piezoelectric motor mount surface whereby the piezoelectric motor is configured to rotate the mount surface relative to the bottom plate body about the central axis of the bottom plate. The multi-axis positioning system may also include a top plate assembly having a top plate body, including a plurality of suspension member mounts which are disposed on an outer portion of the top plate body that receive an upper end of respective resilient suspension members of the bottom plate. A thin slotted flexure assembly may be coupled between the bottom plate and top plate, and include a flexure body which incorporates a central aperture that has a central axis. The flexure assembly may also include a plurality of slots which extend radially from the central axis and central aperture and which terminate inwardly of an outer radial edge of the flexure body. The slots delineate at least one fixed sector of the flexure body and at least one circumferentially adjacent moveable sector of the flexure body. An inner portion of the at least one fixed sector may be secured to a respective piezoelectric motor mount surface of the bottom plate assembly, and an inner portion of the at least one moveable sector may be secured to the top plate assembly. The flexure assembly may be configured to allow tip, tilt and Z axis relative movement between the bottom plate assembly and top plate assembly, and to transmit relative θ displacement from the at least one piezoelectric motor of the bottom plate assembly to the top plate assembly. A plurality of Z axis motors may be disposed and operatively coupled between corresponding outer portions of the bottom plate and respective outer portions of the top plate, and be configured to generate Z axis displacement between the respective outer portions of the bottom plate and top plate. A plurality of Z axis position sensors may be operatively coupled to the top plate and configured to measure Z axis displacement of the top plate. At least one θ position sensor may be operatively coupled between the upper stage of the x-y stage assembly and the top plate assembly, and which is configured to measure relative displacement in a θ rotation direction between the upper stage and the top plate. The multi axis positioning system may also include at least one θ motor which is operatively coupled between the bottom plate assembly and the upper stage of the x-y stage assembly, with the at least one θ motor being configured to rotate the bottom plate assembly in a θ direction relative to the upper stage. A precision bearing assembly may be operatively coupled between the upper stage of the x-y stage assembly and the bottom plate body. The precision bearing assembly may be configured to restrict θ rotation of the bottom plate assembly relative to the x-y stage assembly to rotation about a central axis of the precision bearing assembly with the central axis being fixed relative to the upper stage. The multi-axis positioning system may also include a control system which is operatively coupled to the motors, position sensors and linear actuators of the positioning system.

Some embodiments of a multi-axis positioning system may include a translation stage which is configured to provide displacement in two dimensions between a base and an upper stage of the translation stage. A bottom plate may be rotatably coupled to the translation stage such that an axis of rotation of the bottom plate in a θ rotation direction is perpendicular to a plane defined by the two dimensions of displacement of the translation stage. At least one bottom plate motor may be operatively coupled between the bottom plate and the translation stage, with the at least one bottom plate motor being configured to rotate the bottom plate assembly in the θ rotation direction relative to the translation stage. A top plate may be operatively coupled to the bottom plate, with at least three Z axis motors disposed and operatively coupled between corresponding outer portions of the bottom plate and respective outer portions of the top plate. The Z axis motors may be configured to generate displacement between the respective outer portions of the bottom plate and top plate in a Z axis direction substantially parallel to the axis of rotation of the bottom plate. The multi-axis positioning system may also include a chuck which is configured to releasably secure a specimen secured to the top plate. The multi-axis positioning system may also include at least three Z axis position sensors which are disposed and operatively coupled between the upper stage of the translation stage and the top plate and which are configured to measure relative displacement in the Z axis direction between the upper stage and the top plate. The multi-axis positioning system may also include at least three θ position sensors which are operatively coupled between the upper stage of the translation stage and the top plate and which are configured to measure relative angular displacement in the θ rotation direction between the upper stage and the top plate. A controller system may be operatively coupled to the Z axis motors, the at least one bottom plate motor, the Z axis position sensors, and the θ position sensors. The controller system is configured to control actuation of the Z axis motors and at least one bottom plate motor.

Some embodiments of an optical inspection system may include an optical inspection tool including a light source, an optical objective, a detector assembly, an optical train which optically couples the light source, optical objective and detector and an inspection tool controller that is configured to process optical information received by the detector assembly. The optical inspection system may also include a multi-axis positioning system. The multi-axis positioning system may include a translation stage which is configured to provide displacement in two dimensions between a base and an upper stage of the translation stage. The multi-axis positioning system may also include a bottom plate assembly which is rotatably coupled to the translation stage such that an axis of rotation of the bottom plate in a θ rotation direction is perpendicular to a plane defined by the two dimensions of displacement of the translation stage. A bottom plate motor may be operatively coupled between the bottom plate and the translation stage, with the at least one bottom plate motor being configured to rotate the bottom plate assembly in the θ rotation direction relative to the translation stage. A top plate may be operatively coupled to the bottom plate with at least three Z axis motors disposed and operatively coupled between corresponding outer portions of the bottom plate and respective outer portions of the top plate. The Z axis motors may be configured to generate displacement between the respective outer portions of the bottom plate and top plate in a Z axis direction substantially parallel to the axis of rotation of the bottom plate. The multi-axis positioning system may also include a chuck assembly which is secured to the top plate and which is configured to releasably secure a specimen thereto. The chuck assembly may be disposed in communication with an optical path of the optical objective of the optical inspection tool. At least three Z axis position sensors may be disposed and operatively coupled between the upper stage of the translation stage and the top plate. The Z axis position sensors may be configured to measure relative displacement in the Z axis direction between the upper stage and the top plate. At least three θ position sensors may be operatively coupled between the upper stage of the translation stage and the top plate, and which are configured to measure relative angular displacement in the θ rotation direction between the upper stage and the top plate. A positioning system controller may be operatively coupled to the Z axis motors, the at least one bottom plate motor, the Z axis position sensors and the θ position sensors. The positioning system controller may be configured to control actuation of the Z axis motors and at least one bottom plate motor.

Some embodiments of a method for inspecting a specimen may include loading the specimen into a chuck of a multi-axis positioning system. The multi-axis positioning system may include a translation stage and a bottom plate which is rotatably coupled to the translation stage. The multi-axis positioning system may also include a top plate which is operatively coupled to the bottom plate such that the top plate may be displaced relative to the bottom plate along a Z axis, a tip axis, a tilt axis and along a θ rotation direction. The chuck may be secured to the top plate in some cases. The method for inspecting a specimen may also include measuring a position of one or more test features disposed on the specimen to generate test feature position data, with the test feature position data including a Z axis position of the one or more test features along an optical axis of an objective of an optical inspection tool. The method for inspecting a specimen may also include storing the test feature position data in a memory storage device and generating a look up chart of a surface orientation of the specimen from the test feature position data. The method for inspecting a specimen may also include translating the specimen relative to the objective in an x-y plane perpendicular to the optical axis of the objective, while positioning the specimen with the multi-axis positioning system. Positioning of the specimen may be carried out according to the look up chart using θ position data feedback from a plurality of θ position sensors which are disposed and operatively coupled between the translation stage and top plate of the multi-axis positioning system. The positioning may also use Z axis position feedback from a plurality of Z axis position sensors which are disposed and operatively coupled between the translation stage and top plate of the multi-axis positioning system. The specimen may be translated such that an upper surface of the specimen remains perpendicular to an optical axis of the objective and the upper surface of the specimen remains at a constant distance from the objective.

Some embodiments of a method for inspecting a specimen may include loading the specimen into a chuck of a multi-axis positioning system, with the multi-axis positioning system including a translation stage, and a bottom plate which is rotatably coupled to the translation stage. The multi-axis positioning system may also include a top plate which is operatively coupled to the bottom plate such that the top plate may be displaced relative to the bottom plate along a Z axis, a tip axis, a tilt axis and along a θ rotation direction. The multi axis position system may also include a chuck assembly which is secured to the top plate. The method for inspecting a specimen may also include translating the specimen relative to an optical inspection tool while positioning the specimen with the multi-axis positioning system using theta position data feedback from a plurality of θ position sensors which are disposed and operatively coupled between the translation stage and top plate of the multi-axis positioning system, and using Z axis position feedback from a plurality of Z axis position sensors which are disposed and operatively coupled between the translation stage and top plate of the multi-axis positioning system.

Certain embodiments are described further in the following description, examples, claims and drawings. These features of embodiments will become more apparent from the following detailed description when taken in conjunction with the accompanying exemplary drawings.

BRIEF DESCRIPTION OF THE DRAWINGS

The drawings illustrate embodiments of the technology and are not limiting. For clarity and ease of illustration, the drawings may not be made to scale and, in some instances, various aspects may be shown exaggerated or enlarged to facilitate an understanding of particular embodiments.

DETAILED DESCRIPTION

Figure 1:
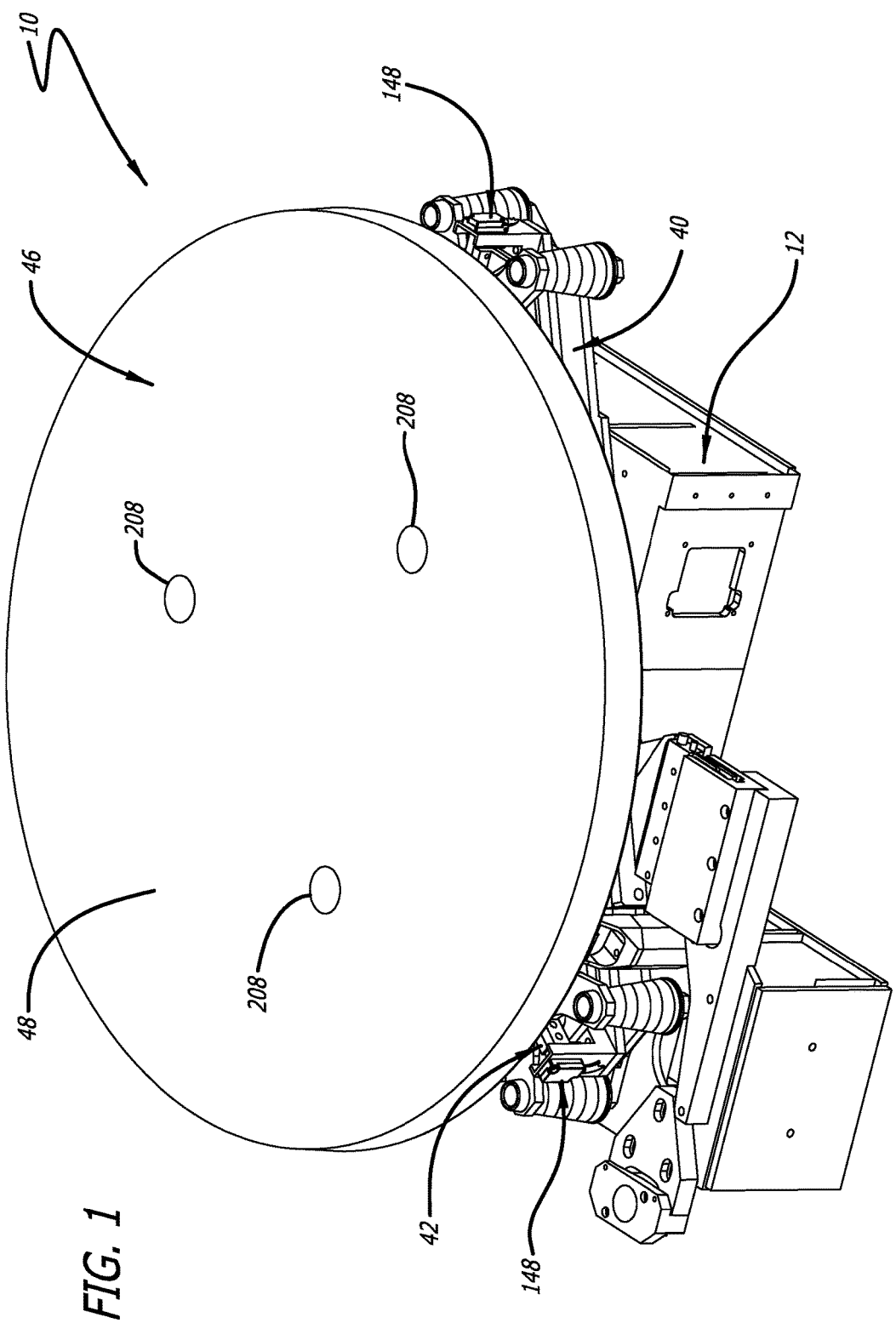
FIG. 1 is a perspective view of an embodiment of a multi-axis positioning system.

Embodiments discussed herein are generally directed to multi-axis positioning systems which may be used to precisely position specimens for the purpose of inspection, processing, manufacturing or any other suitable purpose regarding the specimens. In some cases specimens may include semiconductor based wafer chips or the like which may be fabricated or inspected using the multi-axis positioning system. In some cases the multi-axis positioning system embodiments discussed herein may be particularly suitable for positioning large semiconductor wafer chips, such as semiconductor wafer chips having an outer transverse dimension or diameter of about 400 mm to about 500 mm. The ability of multi-axis positioning system embodiments to provide for precise linear and angular positioning of a specimen along and about multiple axes allows such embodiments to be used in conjunction with suitable optical inspection equipment or the like for the purpose of precisely positioning specimens which are being inspected or otherwise processed. Multi-axis positioning system embodiments discussed herein may also be used in conjunction with any suitable fabrication equipment or the like for the purposes of precisely positioning specimens which are being fabricated. The multi-axis positioning system may be configured such that different elements such as various sub-assemblies of the multi-axis positioning system provide for translational and/or rotational motion of a specimen along or around each respective axis.

The position of the specimen during rotational and/or translational motion may be determined using at least one position sensor which may be suitably configured into the multiple axis positioning system. For some embodiments, multiple position sensors may be suitably configured into the multiple axis positioning system with the multiple position sensors being used to determine the position of the specimen about or along one or more axes during positioning or while at rest. The position sensors of the multiple axis positioning system which are discussed hereafter may include any suitable position sensor type or types such as encoders, for example optical encoders, ultrasonic encoders, communication with interferometers or the like. Specimen position data from the position sensors may be in communication with a controller system of the multi-axis positioning system, with the controller system being configured to analyze and record specimen position data received from one or more of the position sensors.

The controller system of the multi-axis positioning system may also be used to generate a signal to one or more of the motors of the multi-axis positioning system to rotate and/or translate the specimen to any desired position or orientation. The specimen position data which may be stored in a storage device of the controller system may be shared or otherwise communicated by the controller system with the respective controller systems of inspection equipment and/or fabrication equipment in order to facilitate the inspection and/or fabrication process. For example, the controller system may send or otherwise communicate specimen position data to a controller system of an optical inspection tool. The controller system of the optical inspection tool may in turn process the specimen position data and subsequently communicate positioning information or feedback to the controller system of the multi axis positioning system. The controller system of the multi axis positioning system may then generate a signal to translate or rotate the specimen to any desired position or orientation such that specific features of the specimen can be inspected by the optical inspection tool. The controller system of the multi-axis positioning system may thus be instructed by external controller systems (such as the controller system of the optical inspection tool) to translate and/or rotate the specimen to a desired position.

Figure 2:
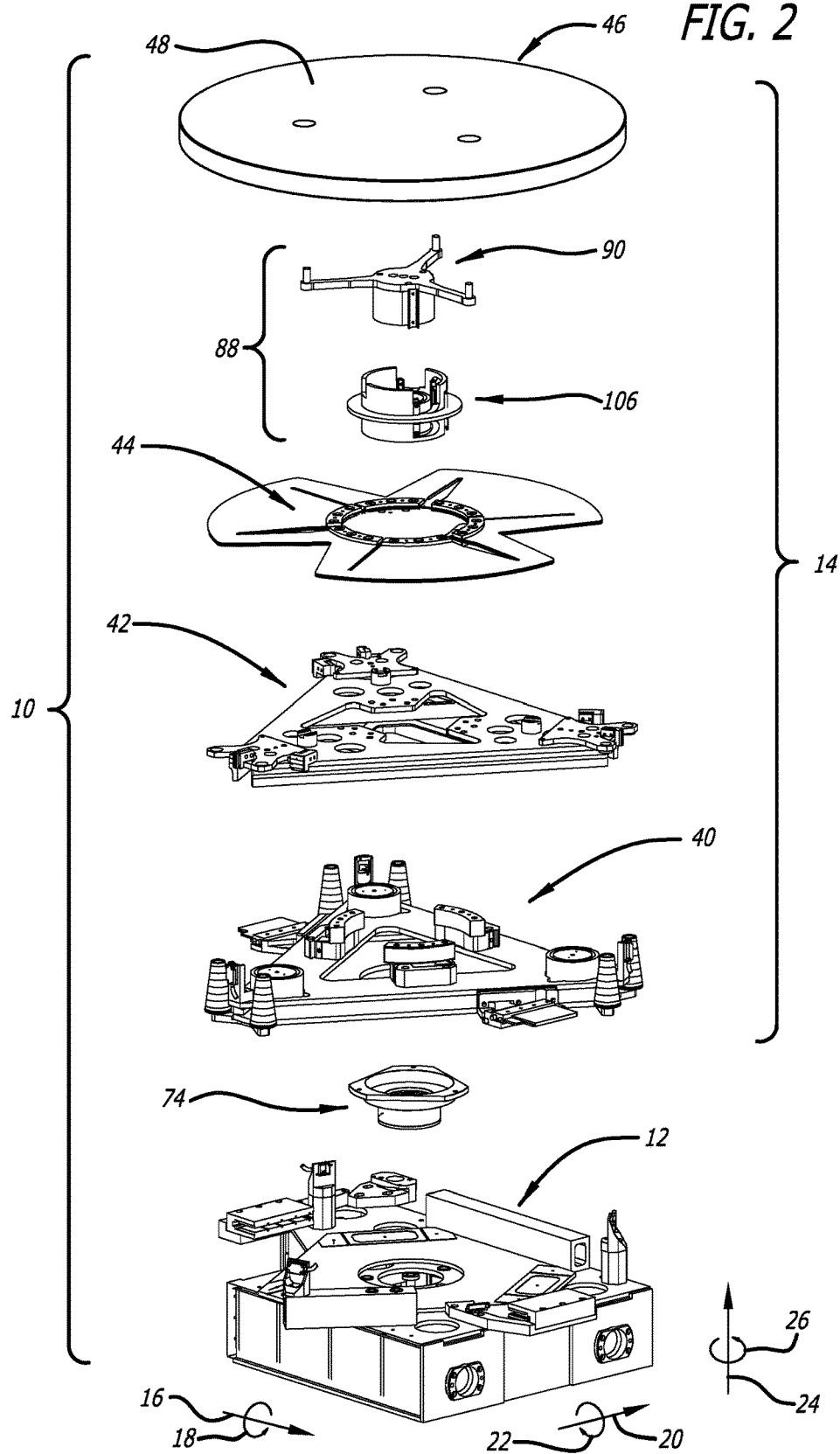
FIG. 2 is an exploded view of the multi-axis positioning system of FIG. 1.

As discussed above, embodiments of the multi-axis positioning system may be configured such that different elements of the multi-axis positioning system provide for the translational and rotational motion of the specimen along or about the multiple axes. Some sub-assembly elements of multi-axis positioning system 10 may include a translation stage which is configured as an x-y stage assembly 12 and a Z, Theta (θ), Tip, Tilt, (ZTTT) assembly 14 which is secured to the x-y stage assembly 12 both of which are shown in FIG. 2. An embodiment of a fully assembled multi-axis positioning system 10 is shown in FIG. 1. FIG. 2 also shows multiple axes which may be used in order to discuss the relative orientation of various motions of the x-y stage assembly 12, the ZTTT assembly 14, and the specimen which may be secured to the ZTTT assembly 14. Axis 16 is oriented along the positive X axis, hence translation of any element along axis 16 is translation along the X axis 16. Rotation about the X axis 16 in the positive direction (as indicated by arrow 18) shall be depicted as rotation in the Tilt angular direction 18. Similarly axis 20 is oriented along the positive Y axis, hence translation of any element along axis 20 is translation along the Y axis 20. Rotation about the Y axis 20 in the positive direction (as indicated by arrow 22) shall be depicted as rotation in the Tip angular direction 22. Axis 24 is oriented along the positive Z axis, hence translation of any element along axis 24 is translation along the Z axis 24. Rotation about the Z axis 24 in the positive direction (as indicated by arrow 26) shall be depicted as rotation in the θ angular direction 26. The X, Y, and Z axes discussed herein are all generally orthogonal to each other.

During use, the specimen which is to be positioned using the multi-axis positioning system 10 may be secured to a portion of a ZTTT assembly 14 such as a chuck 46. The x-y stage assembly 12 may be configured to provide for the linear motion of the specimen along the X axis 16 and/or along the Y axis 20 relative to a reference surface (not shown) to which the x-y stage assembly may be secured. The ZTTT assembly 14 may be configured to provide for the linear motion of the specimen along the Z axis 24 and to provide for the rotational motion of the specimen about the θ angular direction 26, about the Tilt angular direction 18, and about the Tip angular direction 22. For some embodiments of the multi-axis positioning system 10, the ZTTT assembly 14 may be coupled to the x-y stage assembly 12 such that the ZTTT assembly 14 may rotate with respect to the x-y stage assembly 12 about the θ angular direction 26. Typically positioning of the specimen which is performed by the multi-axis positioning system 10 is performed according and in response to signals generated by a controller system 28 of the multi-axis positioning system 10. What follows is a discussion of the various elements of the multi-axis positioning system 10 and the function which each of the elements contributes in positioning the specimen in response to positioning signals generated by the controller system 28 and communicated to the various respective motors of the multi-axis positioning system 10.

The manner in which the various elements of the ZTTT assembly 14 are coupled to each other allows for the translational motion of the chuck assembly 46 (and therefore a specimen secured to the chuck assembly 46) along the Z axis 24 with respect to the x-y stage assembly 12, as well as for rotational motion of the chuck in the θ angular direction 26, the Tilt angular direction 18, and the Tip angular direction 22 all with respect to the x-y stage assembly 12. Any suitable motors such as electromagnetic motors, piezoelectric motors, or the like may be included within the ZTTT assembly 14 in order to provide motive force to translate and/or rotate the chuck assembly 46 of the ZTTT assembly 14 with respect to the x-y assembly 12 along and/or about the multiple axes. For example a plurality of motors such as three electromagnetic motors may be suitably positioned and operatively coupled between the top plate assembly 42 and the bottom plate assembly 40 and may be used to translate the top plate assembly 42 (and therefore the chuck assembly 46) away from or towards the bottom plate assembly 40 along the Z axis 24. These motors may also be used in order to rotate the top plate assembly 42 (and therefore the chuck assembly 46) about the Tip axis 22 and/or the Tilt axis 18. Another source of motive force such as an electromagnetic motor or motors may be operatively coupled between the x-y stage assembly 12 and the bottom plate assembly 40, generating a motive force which provides θ rotation 26 of the bottom plate assembly 40 about the Z axis 24 with respect to the x-y stage assembly 12. At least one additional motor, such as a piezoelectric motor, may be operatively coupled between the bottom plate assembly 40 and the top plate assembly 42, with the at least one piezoelectric motor providing a motive force which also generates θ axis rotation 26 of the top plate assembly 42 about the Z axis 24 with respect to the bottom plate assembly 40.

Figure 3:
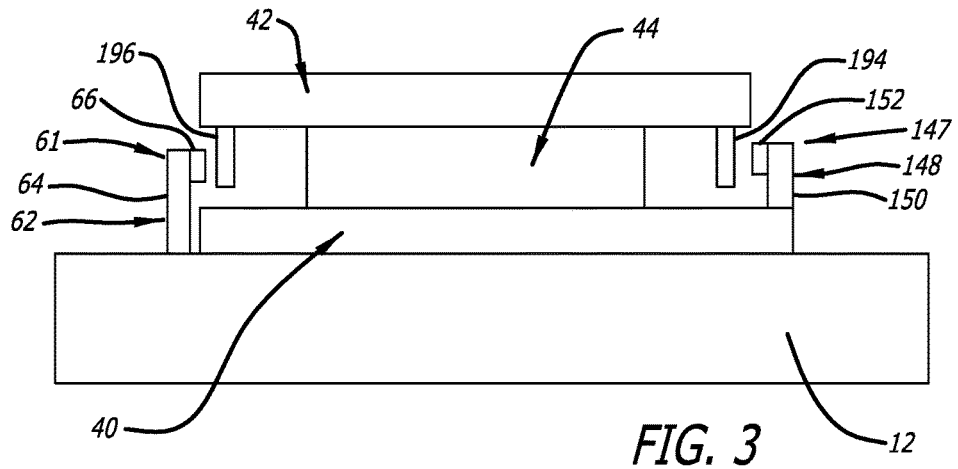
FIG. 3 is a two dimensional block diagram of the multi-axis positioning system of FIG. 1.

As discussed above the multi-axis positioning system 10 may incorporate multiple position sensors. Some position sensor configurations may include optical encoders which may be used to measure the position of the top plate assembly 42 relative to other sub-components of the multi-axis positioning system 10. The optical encoders of the multi-axis positioning system may include Z axis encoder assemblies 147 and θ encoder assemblies 61. FIG. 3 is a two dimensional block diagram showing representations of several sub-assemblies of the multi-axis positioning system 10, as well as representations of a Z axis encoder assembly 147 and θ encoder assembly 61. The block diagram shown in FIG. 3 does not in general accurately depict the relative size or shape of each sub-assembly which is depicted in the block diagram; the block diagram is intended to illustrate the general physical and functional relationship of the encoder assemblies with respect to each sub-assembly of the multi-axis positioning system 10 which is depicted in the block diagram.

FIG. 3 depicts representations of the x-y stage assembly 12, the bottom plate assembly 40, the flexure assembly 44, the top plate assembly 42, sub-assemblies of a θ optical encoder assembly 61, and sub-assemblies of a Z axis encoder assembly 147. The θ optical encoder assembly 61 includes a θ encoder strip 196 and a θ encoder post assembly 62 which includes a θ encoder post 64 and a θ encoder reader 66. As can be seen in the block diagram, the θ optical encoder assembly 61 is disposed and operatively coupled between the x-y stage assembly 12 and the top plate assembly 42. The θ encoder assembly 61 is configured to measure the θ axis 26 angular displacement of the top plate assembly 42 with respect to the x-y stage assembly 12 when the θ encoder reader 66 measures θ axis 26 position data from the θ encoder strip 196, the θ encoder strip 196 being rigidly secured to the top plate assembly 42. The Z axis encoder assembly 147 includes a Z encoder strip 194 and a Z encoder post assembly 148 which includes a Z encoder post 150 and a Z encoder reader 152. The Z axis encoder assembly 147 is disposed and operatively coupled between the bottom plate assembly 40 and the top plate assembly 42. The Z axis optical encoder assembly 147 is configured to measure the Z axis 24 displacement of the top plate assembly 42 with respect to the bottom plate assembly 40 when the Z encoder reader measures Z axis 24 position data from the Z encoder strip 194, the Z encoder strip 194 being secured to the top plate assembly 42.

Figure 4:
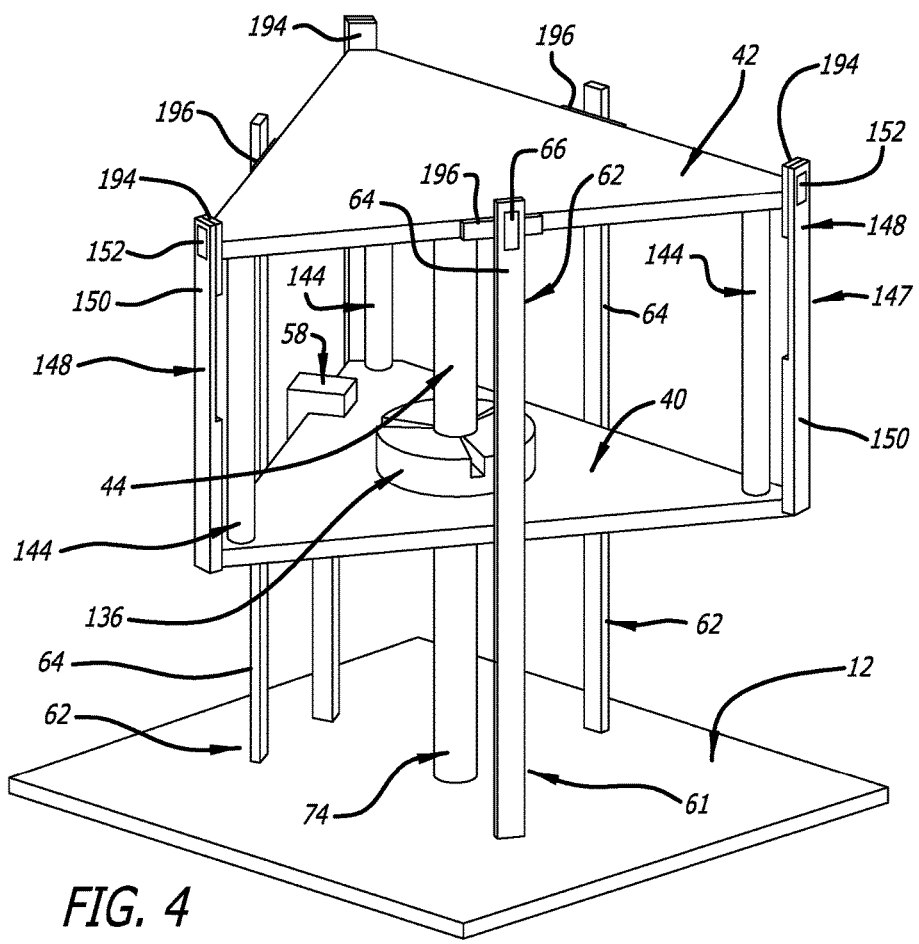
FIG. 4 is a three dimensional block diagram of the multi-axis positioning system of FIG. 1.

FIG. 4 is a three dimensional block diagram of the multi-axis positioning system 10 of FIG. 1 which is intended to further clarify the position of the encoder assemblies with respect to various sub-assemblies of the multi-axis positioning system 10. Again the block representations of the sub-assemblies of the multi-axis positioning system 10 depicted in FIG. 4 are not intended to accurately represent the specific structure of each sub assembly, they are intended to show the functional relationships between the encoders and other various sub-assemblies. The representation of the multi-axis positioning system 10 in FIG. 4 includes the x-y stage assembly 12, the bottom plate assembly 40, the top plate assembly 42, piezoelectric motor assemblies 136, a θ motor assembly 58, and three Z motor assemblies 144. Also represented are a flexure assembly 44 and a precision bearing assembly 74.

As discussed above the three Z axis encoder assemblies 147 are disposed and operatively coupled between the bottom plate assembly 40 and the top plate assembly 42 as further shown in FIG. 4. The three Z axis encoder assemblies 147 include three Z encoder post assemblies 148 which are each rigidly secured to the bottom plate assembly 40. Each Z encoder post assembly 148 includes a Z encoder post 150 and a Z encoder reader 152. Each Z axis encoder assembly 147 is configured to measure the Z axis 24 displacement of the top plate assembly 42 with respect to the bottom plate assembly 40 when each Z encoder reader 152 measures Z axis 24 position data from a respective Z encoder strip 194 which is rigidly secured to the top plate assembly 42. Three θ encoder assemblies 61 are disposed and operatively coupled between the x-y stage assembly 12 and the top plate assembly 42 as represented in FIG. 4. The three θ encoder assemblies 61 include three θ encoder post assemblies 62 which are each rigidly secured to the x-y stage assembly 12. Each θ encoder post assembly 62 includes a θ encoder post 64 and a θ encoder reader 66. Each θ axis encoder assembly 61 is configured to measure the θ axis 26 displacement of the top plate assembly 42 with respect to the x-y stage assembly 12 when each θ encoder reader 66 measures θ axis 26 position data from a respective θ encoder strip 196 which is rigidly secured to the top plate assembly 42.

Figure 5:
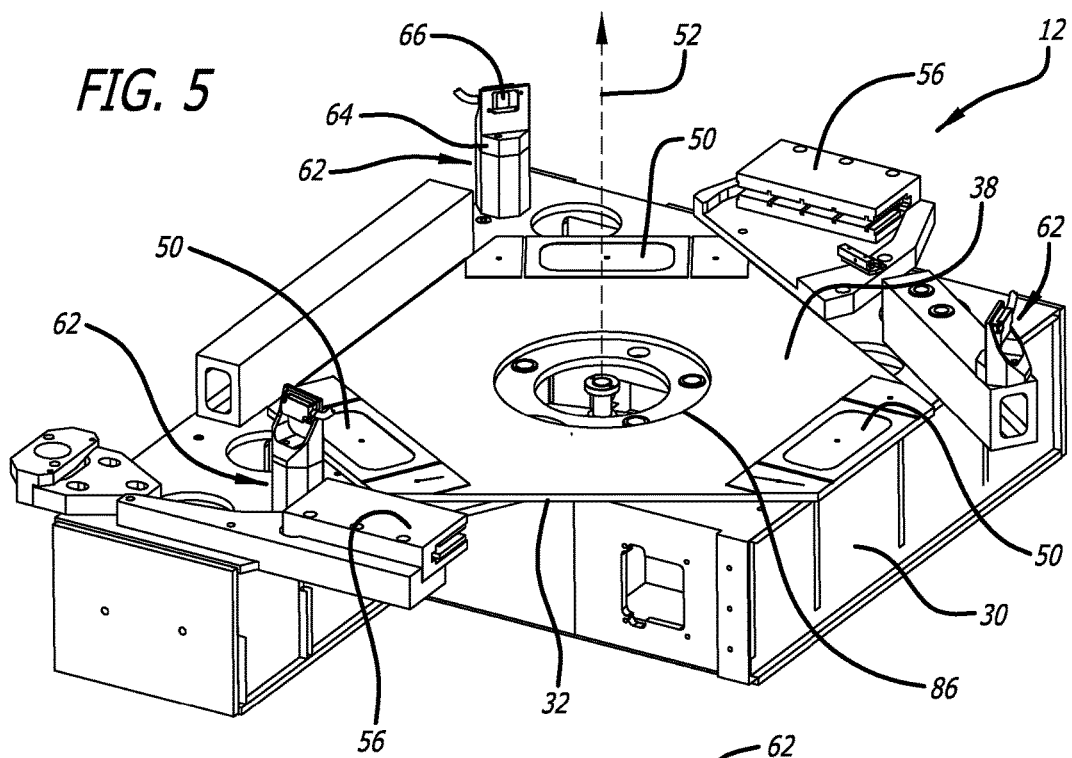
FIG. 5 is a perspective view of an x-y stage assembly.
Figure 6:
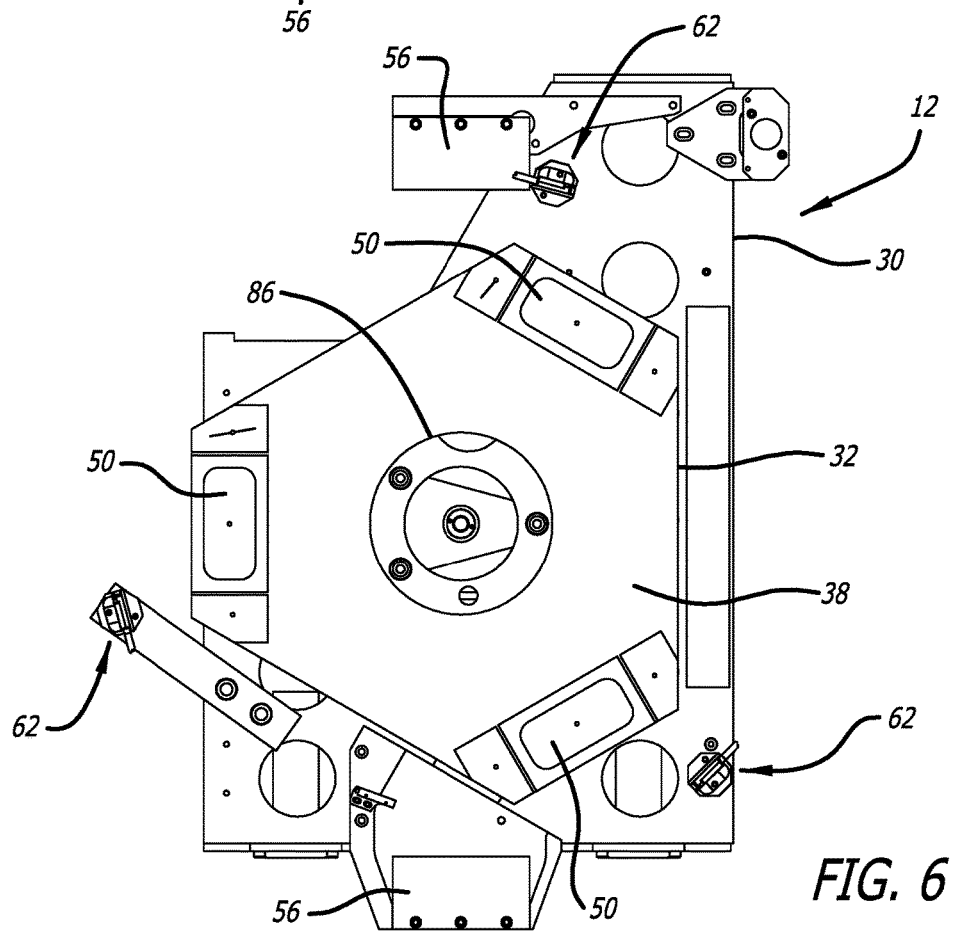
FIG. 6 is an elevation view of the x-y stage assembly of FIG. 5.

FIGS. 5 and 6 depict the embodiment of the x-y stage assembly 12 which may include a base 30 which may be secured to any suitable surface (typically any suitable stable surface adjacent inspection or processing equipment). The x-y stage assembly 12 may include a first linear actuator and a second linear actuator (both not shown) both of which are configured such that they are in operative communication with the controller system 28. The x-y stage assembly 12 may also include an upper stage 32 which may be operatively coupled to the first linear actuator and the second linear actuator. The first linear actuator may be configured such that when it is activated by the controller system 28, it produces a controllable displacement of the upper stage 32 along the X axis 16 relative to the base 30. The second linear actuator may be configured such that when it is activated by the controller system 28 it produces a controllable displacement of the upper stage along the Y axis 20 relative to the base 30. Thus the first linear actuator and the second linear actuator of the x-y stage assembly 12 are configured to produce a controllable displacement of the upper stage 32 of the x-y stage assembly 12 along the X axis 16 and/or the Y axis 20 at the direction of the controller system 28. The motion of the specimen 220 which is provided by the embodiment of the x-y stage assembly 12 of the multi-axis positioning system 10 thus includes translation along the X axis 16 and/or the Y axis 20. The ZTTT assembly 14, however, is configured to provide a much wider range of translational and rotational motion to the specimen 220. An illustration of the specimen 220 secured to the chuck 46 is shown in the block diagram of FIGS. 51 and 53.

The ZTTT assembly may be suitably coupled to an upper surface 38 of the upper stage 32 of the x-y stage assembly 12. The ZTTT assembly 14 may be configured using elements which are light weight such that the overall weight of the ZTTT assembly 14 on the x-y stage assembly 12 is not excessive. The ZTTT assembly 14 may include the bottom plate assembly 40, the top plate assembly 42, the flexure assembly 44, and the optional chuck assembly 46 all of which are shown in FIGS. 1 and 2. The specimen 220 (see FIG. 51) which is to be positioned by the multi-axis positioning system 10 may be secured to the chuck assembly 46 of the ZTTT assembly 14. The chuck assembly 46 may include a chuck body 48 which may be configured as a rigid disk structure as shown in FIG. 2. The chuck body 48 may be rigidly secured to a top plate body 43 of the top plate assembly 42 such that any translation or rotational motion of the top plate assembly 42 around or about the various axes of motion is transmitted directly to the chuck assembly 46 without relative movement between the chuck assembly 46 and the top plate body 43. Because the chuck assembly 46 is constrained to move in tandem with the top plate assembly 42, the position of the chuck assembly 46 can be indirectly measured by measuring the position of the top plate assembly 42 using one or more of the position sensors.

The x-y stage assembly embodiment 12 depicted in FIGS. 5 and 6 may also include a plurality of flat smooth active reference surfaces 50. For the embodiment shown, the upper stage 32 of the x-y stage assembly 12 includes three active reference surfaces 50 which may be flat parallel surfaces lying in a common plane disposed at equal radial distances from a central axis 52 of the x-y stage assembly 12. The active reference surfaces 50 are also circumferentially disposed along the x-y stage upper surface 38 at angles of about 120 degrees from each other about the central axis 52 of the x-y stage assembly 12 in a circumferential orientation. Each active reference surface 50 may be configured to operatively couple to respective passive reference surfaces 114 (see FIG. 15) which are disposed on the bottom plate assembly 40. A cushion of air may be generated between respective active reference surfaces 50 and passive reference surfaces 114 by forcing a stream of pressurized air into a space or gap disposed between the respective reference surfaces 50 and 114 which are disposed in opposed relation to each other. Such a cushion of air may provide for low friction displacement between the respective active references surfaces 50 and passive reference surfaces 114. The x-y stage assembly 12 may also include at least one θ motor magnet assembly 56. Each θ motor magnet assembly 56 is a subcomponent of a θ motor assembly 58. The θ motor assembly 58 may include both the θ motor magnet assembly 56 and a θ motor coil assembly 60. Each θ motor coil assembly 60 may be suitably disposed on the bottom plate assembly 40. As shown in FIGS. 5 and 6, two θ motor magnet assemblies 56 are disposed on the x-y stage upper surface 38 spaced substantially equidistant from the central axis 52 of the x-y stage assembly 12. Additionally, the θ motor magnet assemblies 56 are disposed circumferentially about the central axis 52 of the x-y stage assembly 12 such that they are spaced at an angular separation of about 180 degrees in the θ angular direction 26.

As discussed above, the translational and rotational motion of the top plate assembly 42 (and the specimen 220 which is secured to the top plate assembly 42 by the chuck assembly 46) with respect to the x-y stage assembly 12 may be measured as specimen position data using position sensors which are operatively coupled to the controller system 28. The position sensor configurations may include encoders, or any other suitable type of position sensing device that can generate a measurable signal. The x-y stage assembly embodiment 12 which is shown in FIGS. 5 and 6 incorporates a plurality θ encoder post assemblies 62. Each θ encoder post assembly 62 is a sub-assembly of a θ encoder assembly 61 which may be operatively coupled between the x-y stage assembly 12 and the upper plate assembly 42 (see FIGS. 3 and 4). In some cases, the θ encoder assemblies 61 are disposed at an outer edge or perimeter of the upper plate assembly 42. Each θ encoder assembly 61 may also include a θ encoder strip 196 which is rigidly secured to the top plate assembly 42 (see FIG. 18). Each θ encoder post assembly 62 may include a θ encoder post 64 and a θ encoder reader 66 which is disposed on a distal end of each θ encoder post 64. Each θ encoder post 64 may be rigidly secured to and extend from the x-y stage upper surface 38. In some cases the θ encoder posts 64 may be substantially perpendicular to the x-y stage upper surface 38. The extension of the θ encoder posts 64 from the x-y stage upper surface 38 may be configured to allow for the θ encoder readers 66 to be operatively coupled to the θ encoder strips 196 of the top plate assembly 42. The θ encoder post assemblies 62 may be radially spaced substantially equidistant from the central axis 52 of the x-y stage assembly 12, and the θ encoder post assemblies 62 may have a circumferential angular separation in the θ angular direction 26 of about 120 degrees.

Figure 7:
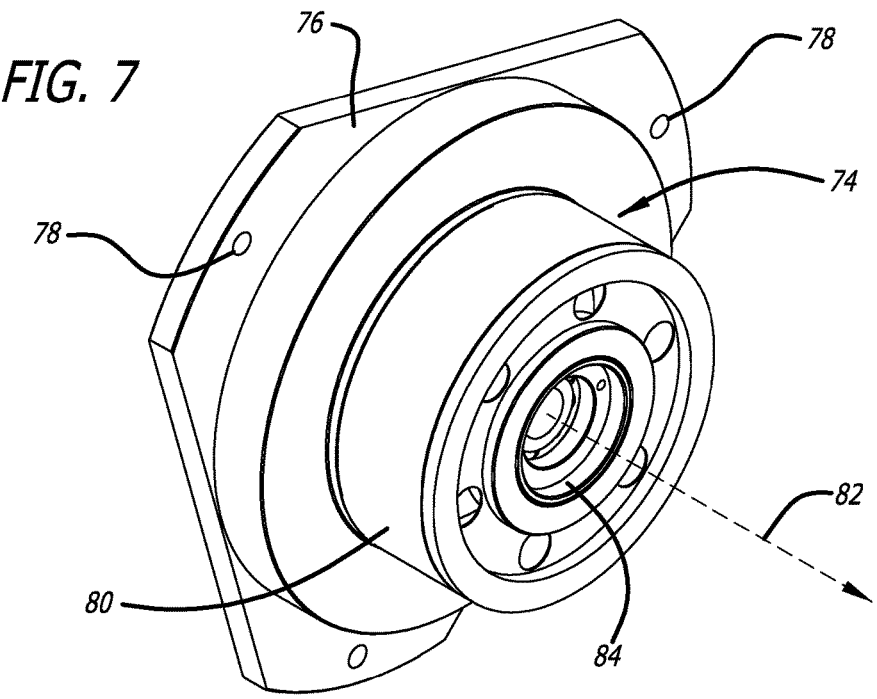
FIG. 7 is a perspective view of a precision bearing assembly.
Figure 8:
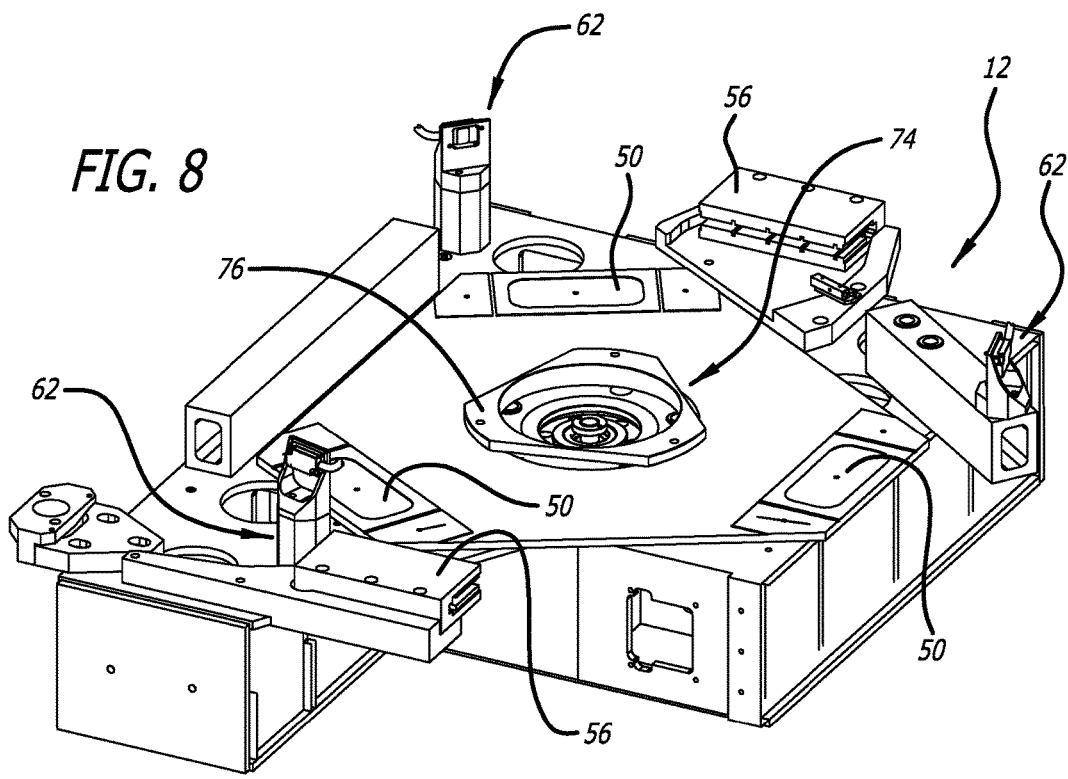
FIG. 8 is a perspective view of the precision bearing assembly of FIG. 7 coupled to the x-y stage assembly of FIG. 5.

The x-y stage assembly 12 may be rotationally coupled to the bottom plate assembly 40 of the ZTTT assembly 14 by the precision bearing assembly 74 or the like which is shown in FIG. 7. The precision bearing assembly 74 may include a bearing base 76 which can be configured as a generally triangular shape with bearing mounting holes 78 at each apex of the triangle. The precision bearing assembly 74 may also include a bearing shaft 80 which can be configured in a generally cylindrical shape, with the bearing shaft 80 being configured to rotate with respect to the bearing base 76 around a central axis 82 of the precision bearing assembly 74. The bearing shaft 80 may also include a threaded mounting section 84 which is symmetrically disposed about the central axis 82 of the bearing shaft 80 and which may be configured to couple to a bearing aperture 86 (see FIG. 5) which is disposed on the x-y stage upper surface 38. The threaded mounting section 84 of the precision bearing assembly 74 is coupled to the bearing aperture 86 with the bearing shaft 80 disposed within the bearing aperture 86. As shown in FIG. 8, movement of the bearing base 76 is thus restricted to rotation in the θ axis angular direction 26 when the precision bearing assembly 74 is secured to the x-y stage assembly 12.

Figure 9:
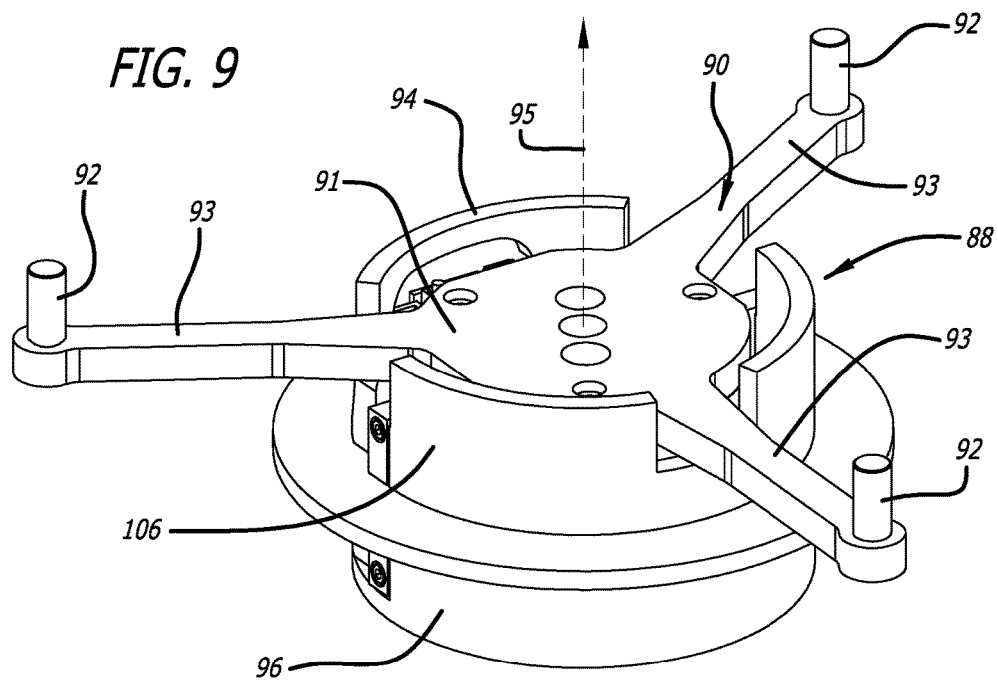
FIG. 9 is a perspective view of a lift pin ejector assembly including an ejector motor housing.

The ZTTT assembly 14 may also include a lift pin ejector assembly 88 which is shown in FIG. 9. The lift pin ejector assembly 88 may include a lift pin assembly 90 which may have a lift pin assembly base 91 configured as a generally circular disk. The lift pin assembly base may include multiple lift pins 92 which are typically parallel to each other and disposed at the outer or distal ends of multiple lift pin arms 93. The lift pin assembly 90 which is depicted in FIG. 9 has three lift pin arms 93 which are disposed at an angular separation of about 120 degrees about a lift pin assembly central axis 95. The lift pin ejector assembly 88 may also include a lift pin assembly aperture 94 which is configured to accept the lift pin assembly 90 (the lift pin assembly 90 being free to slide in and out of the lift pin assembly aperture 94), and a precision bearing assembly boss 96 which is configured to couple to the precision bearing assembly 74. The lift pin ejector assembly 88 may also include an ejector motor (not shown) which is disposed within an ejector motor housing 106 and which may include an ejector motor coil (not shown), an ejector motor magnet (not shown) which is operatively couple to the ejector motor coil. The ejector motor may be operatively coupled to the controller system 28. The ejector motor coil may be coupled to the lift pin assembly 90, and the ejector motor magnet may be secured to the ejector motor housing 106. In use, the lift pin ejector assembly 88 is configured to controllably advance the lift pins 92 along the Z axis 24 in order to remove the specimen 220 from the chuck assembly 46. This occurs when the controller system 28 activates the ejector motor by applying a suitably configured electric current to the ejector motor coils. The electric current running through the ejector motor coils creates a magnetic field which interacts with the ejector motor magnet and causes the movement of the ejector motor coils (which are coupled to the lift pin assembly 90). The movement of the ejector motor coils results in the controlled upward advancement of the lift pin assembly 90 along the Z axis 24. The lift pins 92 should be long enough and properly positioned below the chuck 46 such that they are configured to extend completely corresponding apertures 208 of the chuck 48. The position of the lift pin assembly 90 may be measured by an ejector motor encoder (not shown) which may then transmit position data of the lift pin assembly 90 to the controller system 28.

Figure 10:
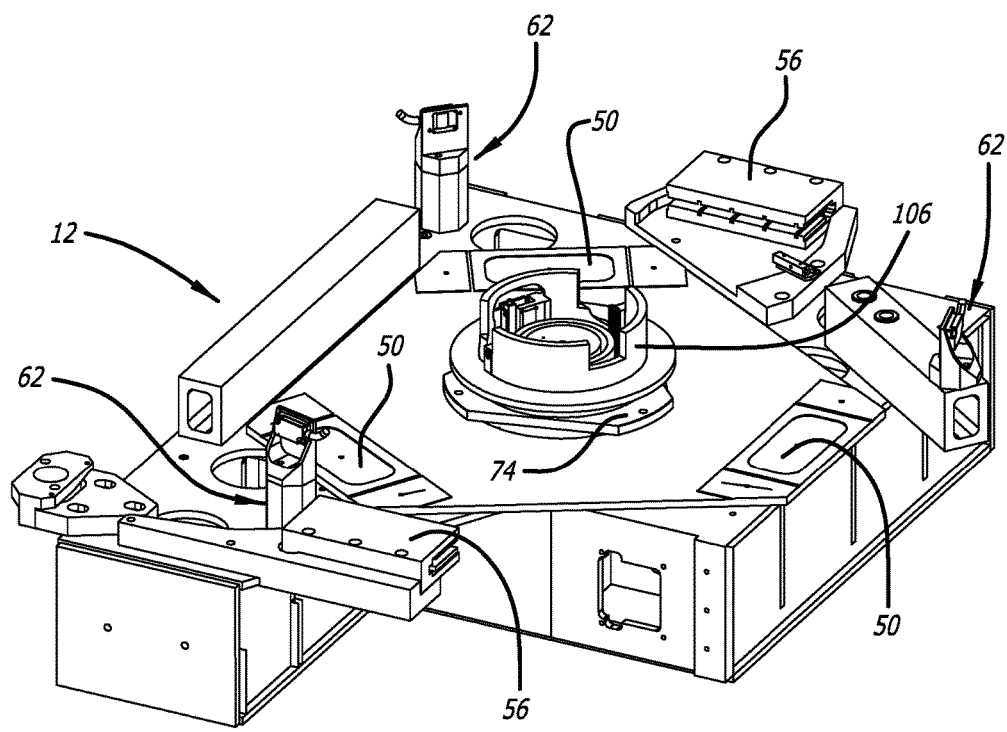
FIG. 10 is a perspective view of the ejector motor housing of FIG. 9 coupled to the x-y stage assembly of FIG. 5.
Figure 11:
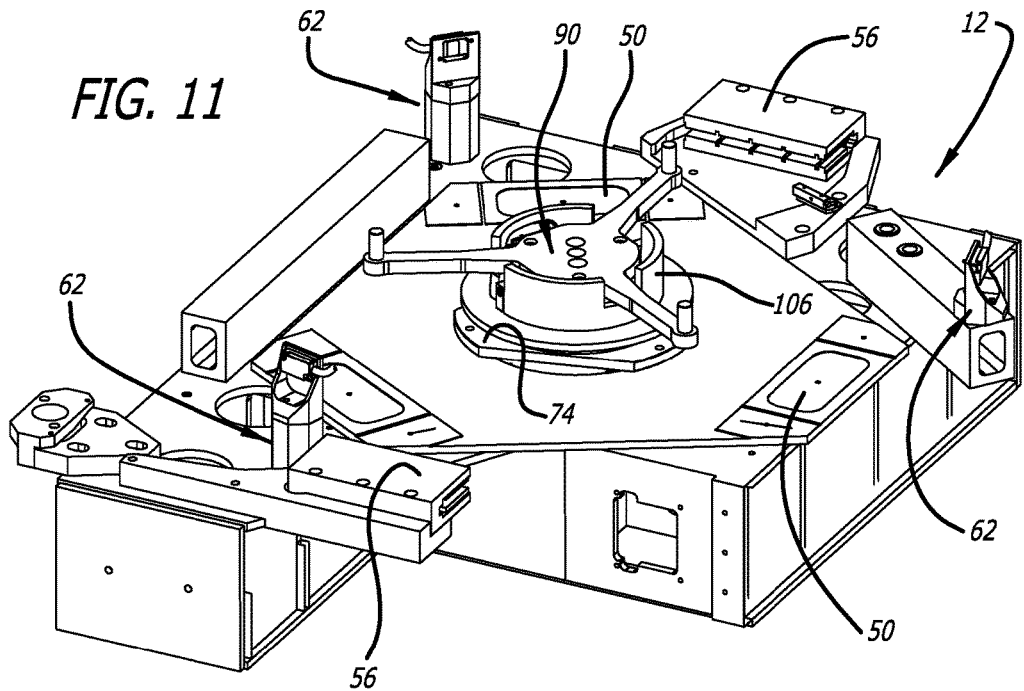
FIG. 11 is a perspective view of the lift pin ejector assembly of FIG. 9 coupled to the x-y stage assembly of FIG. 5.

FIG. 10 depicts the ejector motor housing 106 (which contains the ejector motor, the ejector motor coil, the ejector motor magnet, and the ejector motor encoder 104) coupled to the precision bearing assembly 74, and FIG. 11 depicts the lift pin assembly 90 coupled to the ejector motor housing 106. The lift pin ejector assembly 88 is coupled to the precision bearing assembly 74 such that the lift pin ejector assembly 88 rotates with the precision bearing assembly 74 as the precision bearing assembly 74 is rotated in the θ angular direction 26. For purposes of illustration, the lift pin ejector assembly 88 is shown installed into the precision bearing assembly 74 in FIG. 11, however practically the bottom plate assembly 40 would likely be coupled to the precision bearing assembly 74 prior to the installation of the lift pin ejector assembly 88.

Figure 12:
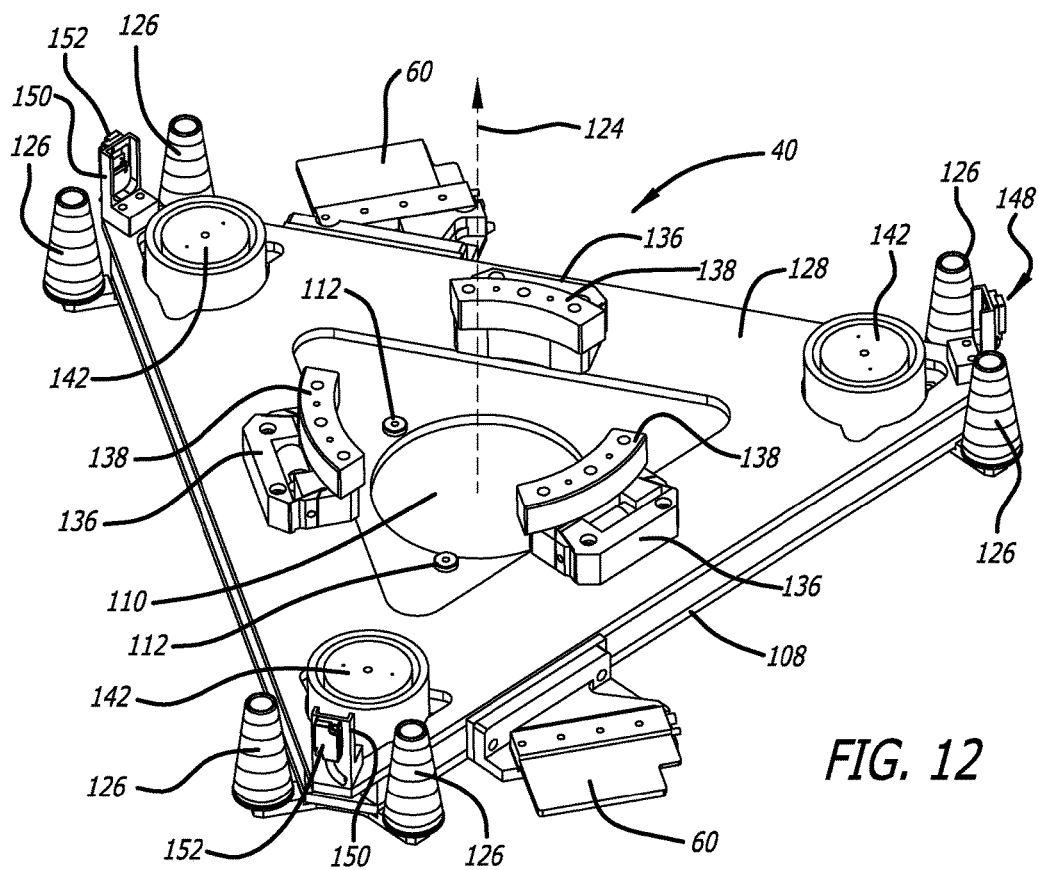
FIG. 12 is a perspective view of a bottom plate assembly embodiment.
Figure 13:
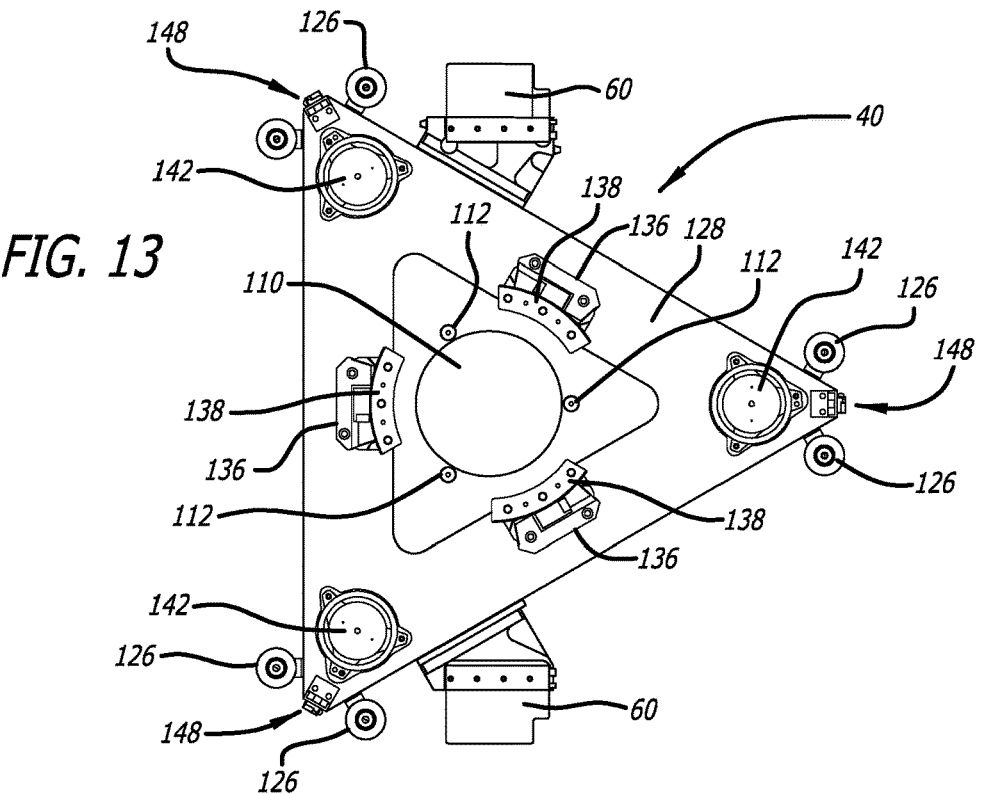
FIG. 13 is an elevation view of the bottom plate assembly embodiment of FIG. 12.
Figure 16:
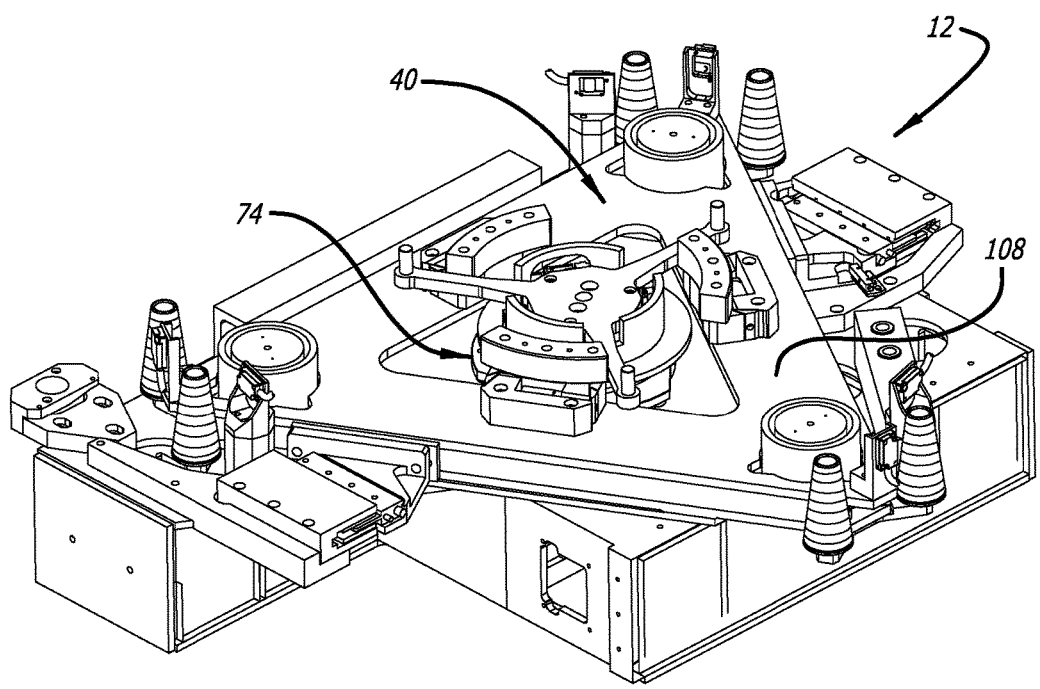
FIG. 16 is a perspective view of the bottom plate assembly of FIG. 12 coupled to x-y stage assembly, the precision bearing assembly, and the lift pin ejector assembly all of FIG. 11.
Figure 17:
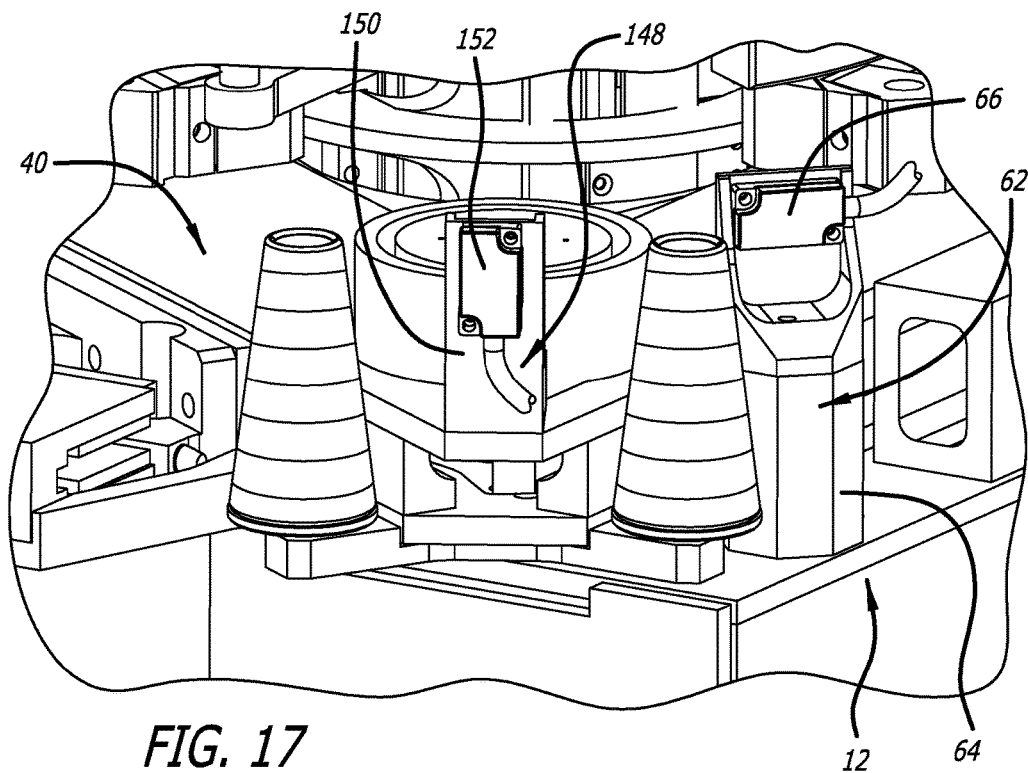
FIG. 17 is an enlarged view of FIG. 16 showing multiple resilient suspension members.

The bottom plate assembly 40 of the ZTTT assembly 14 is shown in FIGS. 12 and 13, and may include a bottom plate body 108. The bottom plate body 108 may be configured in a generally triangular shape with a circular central aperture 110 disposed at the center of the triangle with the central aperture 110 being configured to allow clearance for the lift pin ejector assembly 88. The bottom plate assembly 40 may be operatively coupled to the upper stage 32 of the x-y stage assembly 12 by the precision bearing assembly 74. Fasteners (not shown) may be inserted through the bearing mounting holes 78 of the precision bearing assembly 74 and through mounting holes 112 in the bottom plate body 108 (see FIG. 12) thereby securing the bottom plate body 108 to the precision bearing assembly 74. FIG. 16 shows the bottom plate assembly 40 fastened to the precision bearing assembly 74 which is in turn secured to the x-y stage assembly 12.

The bottom plate assembly 40 may include a plurality of passive reference surfaces 114 which are disposed on a bottom surface 116 (see FIG. 15) of the bottom plate body 108. The passive reference surfaces 114 may be disposed on the bottom surface 116 of the bottom plate body 108, with each passive reference surface 114 having a bottom surface 115 which is substantially parallel to the bottom surface 116 of the bottom plate body 108. In some cases, all of the bottom surfaces 115 lie in a common plane with each other. Each passive reference surface 114 may be positioned at an outer edge or perimeter near an apex of the generally triangular shaped bottom plate body 108 such that when the bottom plate assembly 40 is coupled to the x-y stage assembly 12 the passive reference surfaces 114 are each operatively aligned with their respective active reference surfaces 50 of the x-y stage assembly 12 such that a cushion of air may be formed between the respective surfaces to allow low friction displacement therebetween. In order to provide the cushion of air, each active reference surface 50 may include at least one pressurized gas port 118 and a vacuum port 120 (see FIG. 14). Each pressurized gas port 118 may be connected to a source of pressurized gas 121 (such as an air pump) by pressure lines 122 which may be an air tight elongate flexible tubular member. The source of pressurized gas 121 may be configured to provide a flow of gas, such as air, through each pressure line 122 to a respective pressurized gas port 118 of the active reference surfaces 50. The vacuum port 120 of each active reference surface 50 may be connected to a vacuum source 123 (such as a vacuum pump) by a vacuum line 125 which may be an elongate air tight flexible tubular member. The vacuum source 125 may be configured to provide a vacuum to the vacuum port 120 via each vacuum line 125.

Each pressurized gas port 118 may include at least one pressure groove 119 which may be configured as a slot which is in fluid communication with a respective pressurized gas port 118. Each pressure groove 119 may extend radially from a respective pressurized gas port along the surface of the active reference surfaces 50. Each pressure groove 119 may be configured to direct a portion of pressurized gas which flows from a respective pressurized gas port 118 across a surface of the active reference surfaces 50 for more even distribution of the pressurized gas over the surface of the active reference surfaces 50. Each pressure groove 119 thus acts to distribute a portion of the outflow of gas from its respective pressurized gas port 118 along the length of the pressure groove 119 and beyond. A flow of gas from each pressurized gas port 118 and from its respective pressure grooves 119, and between each active reference surface 50 and its respective passive reference surface 114 may act to provide a pneumatic cushion which slightly separates the active reference surfaces 50 of the upper stage 32 of the x-y stage assembly 12 from the bottom surfaces 115 of the respective passive reference surfaces 114 of the bottom plate body 108. In most cases, all of the active reference surfaces 50 and passive reference surfaces 114 are parallel to each other.

Figure 14:
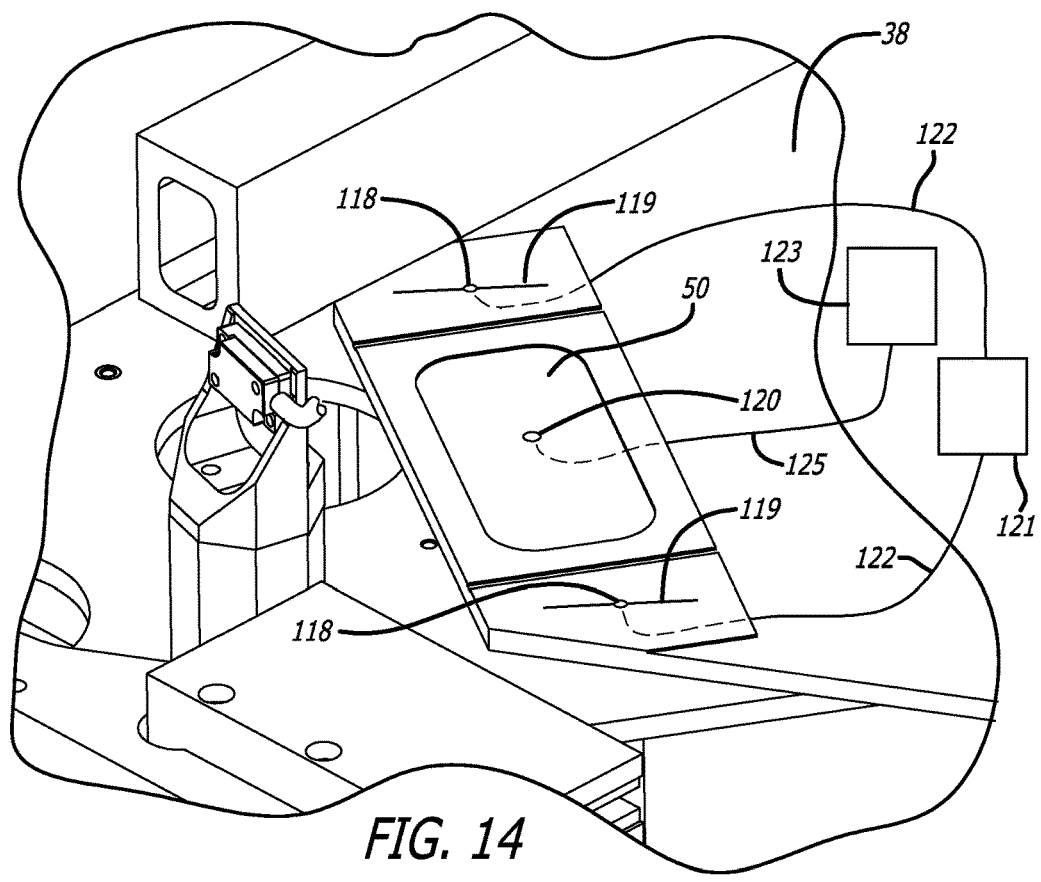
FIG. 14 is an enlarged view of FIG. 5 showing an embodiment of an active reference surface of an upper stage of the x-y stage assembly of FIG. 5.
Figure 15:
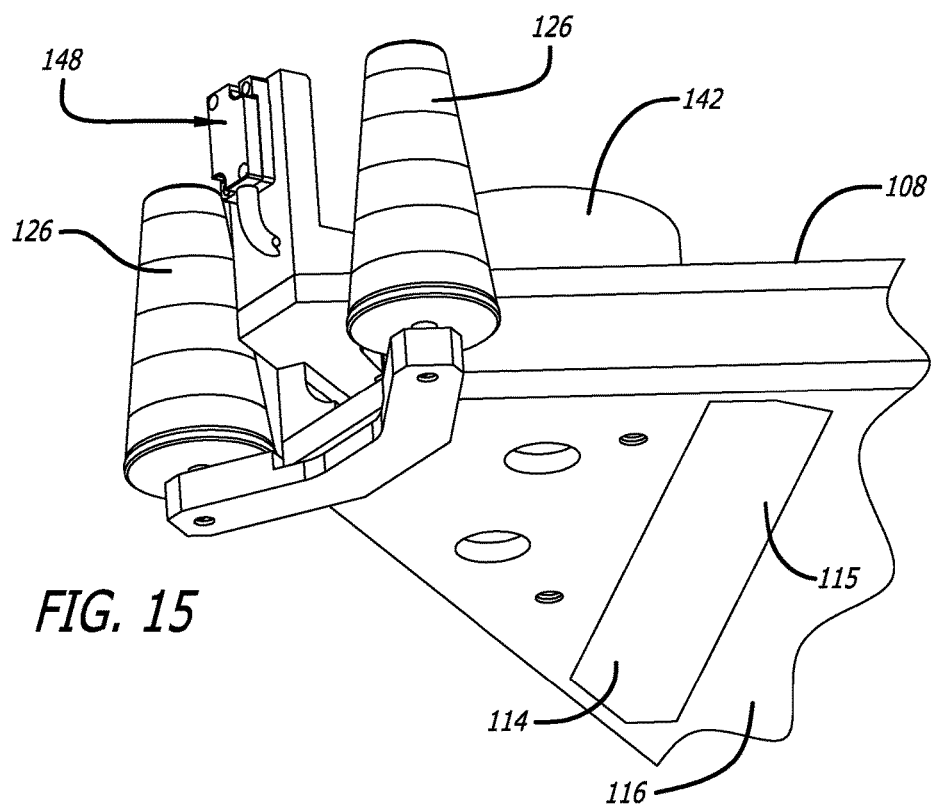
FIG. 15 is an enlarged view of a bottom surface of the bottom plate assembly embodiment of FIG. 12 showing an embodiment of a passive reference surface.

The precision bearing assembly 74 allows the lower plate assembly 40 to rotate in the θ angular direction 26 on this pneumatic cushion relative to the x-y stage assembly 12. Each active reference surface 50 may also include a vacuum port 120 as shown in FIG. 14. The vacuum ports 120 are configured to create a vacuum between the active reference surfaces 50 and the passive reference surfaces 114 when the gas flow to the pressurized gas ports 118 has been reduced or terminated. This application of vacuum between the reference surfaces 50 and 114 removes the air cushion therebetween and draws the respective reference surfaces 50 and 114 together into physical contact with each other which produces a static friction that prevents the rotation of the bottom plate assembly 40 around a central axis 124 of the bottom plate assembly 40 in the θ angular direction 26. As such, when the vacuum is applied to the vacuum ports 120, this application of vacuum effectively locks the position of the bottom plate assembly 40 with respect to the position of the upper stage 32 of the x-y stage assembly 12. The embodiments of the x-y stage 12 and bottom plate assembly shown in FIGS. 14 and 15 are configured with the passive reference surfaces 114 secured to the bottom plate assembly 40 and the active reference surfaces 50 (including the vacuum ports 120 and the pressurized gas ports 118) formed into the upper stage of the x-y stage. Other embodiments may be configured such that the passive reference surfaces 114 are disposed on the upper stage 32 of the x-y stage assembly 12 and the active reference surfaces 50 (including the vacuum ports 120 and the pressurized gas ports 118) are disposed on the bottom surface 116 of the bottom plate body 108. The expulsion of gas from each of the pressurized gas port 118 or the application a vacuum to each of the vacuum ports 120 may be regulated by the controller system 28 of the multi-axis positioning system 10.

As mentioned above, the bottom plate assembly 40 may also include at least one θ motor coil assembly 60 which is a subcomponent of the respective θ motor assembly 58. Each θ motor assembly 58 may be disposed and operatively coupled between the x-y stage assembly 12 and the bottom plate assembly 40. As shown in FIGS. 12 and 13, the bottom plate assembly 40 includes two θ motor coil assemblies 60 which are radially spaced substantially equidistant from a central axis 124 of the bottom plate assembly 40. Additionally, the θ motor coil assemblies 60 are disposed circumferentially about the central axis 124 of the bottom plate assembly 40 such that they are spaced at an angular separation of about 180 degrees in the θ angular direction 26. Each θ motor coil assembly 60 is configured to operatively engage a respective θ motor magnet assembly 56 (see FIG. 11) in order to form a θ motor assembly 58 which effectively operates as an electromagnetic voice coil type motor, however any suitable other type of motor could be used as well. Each θ motor assembly 58 may be operatively coupled to the controller system 28, and each θ motor assembly 58 may rotate the bottom plate assembly 40 in the θ angular direction 26 (with respect to the x-y stage assembly 12) when a suitably configured signal such as an electrical current is sent to each θ motor coil assembly 60 by the controller system 28 thereby creating magnetic fields about each θ motor coil assembly 60 each of which interact with a respective θ motor magnet assembly 56 (which may be permanent magnets in some cases). For other embodiments of the bottom plate assembly 40 and the x-y stage assembly 12, each θ motor coil assembly 60 may be secured to the x-y stage assembly 12 and each θ motor magnet assembly 56 may be secured to the bottom plate assembly 40.

Figure 20:
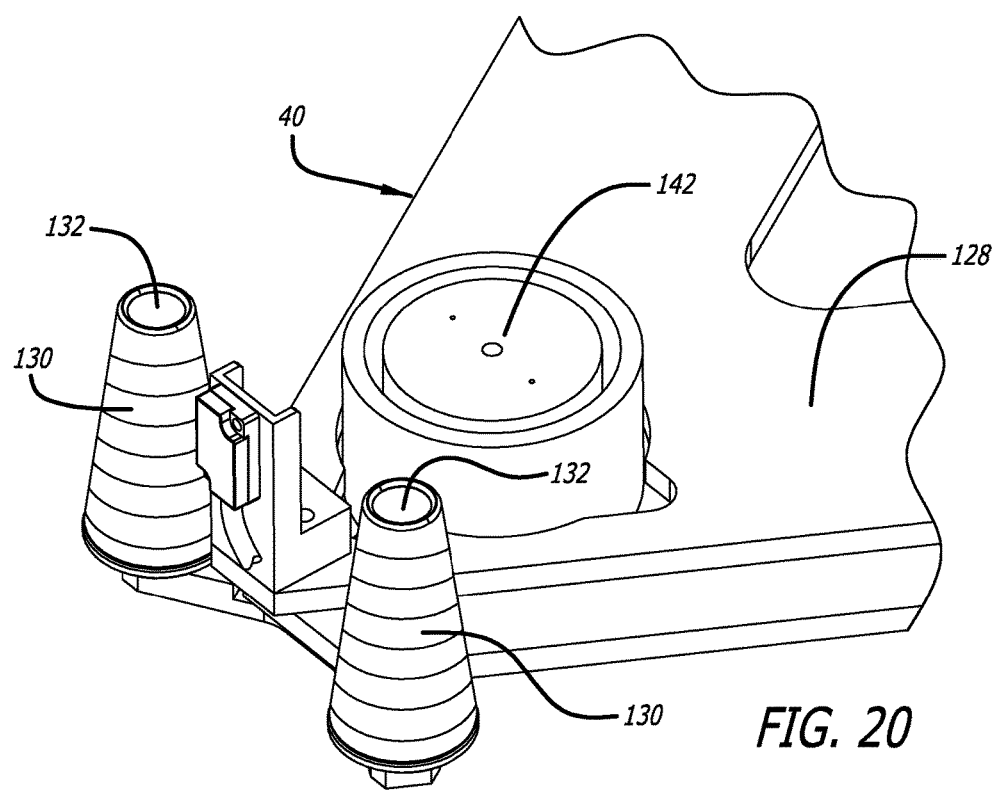
FIG. 20 is an enlarged view of the bottom plate embodiment of FIG. 12 depicting a Z motor magnet assembly disposed on the bottom plate.

The bottom plate assembly 40 may also include at least one resilient suspension member assembly 126 which is configured to resiliently suspend the top plate assembly 42 above the bottom plate assembly 40. For the bottom plate assembly embodiment 40 shown, a total of six resilient suspension member assemblies 126 are secured to the bottom plate assembly 40. For the embodiment 40 shown, 2 resilient suspension member assemblies 126 are disposed at each apex of the triangular shaped bottom plate body 108 and are radially spaced substantially equal from each other about the central axis 124 of the bottom plate assembly 40. Each resilient suspension member assembly 126 may extend upward from an upper surface 128 of the bottom plate assembly 40. Each resilient suspension member assembly 126 may include a suspension member spring 130 which may be disposed over a respective suspension member pin 132 (see FIG. 20). As shown in FIG. 20, each suspension member spring 130 may be configured as a tapered coil spring which is disposed over its respective suspension member pin 132. Each suspension member pin 132 may be configured to slidably engage with a respective suspension member receptacles 134 (see FIG. 30) which are disposed on the top plate body 43.

Figure 30:
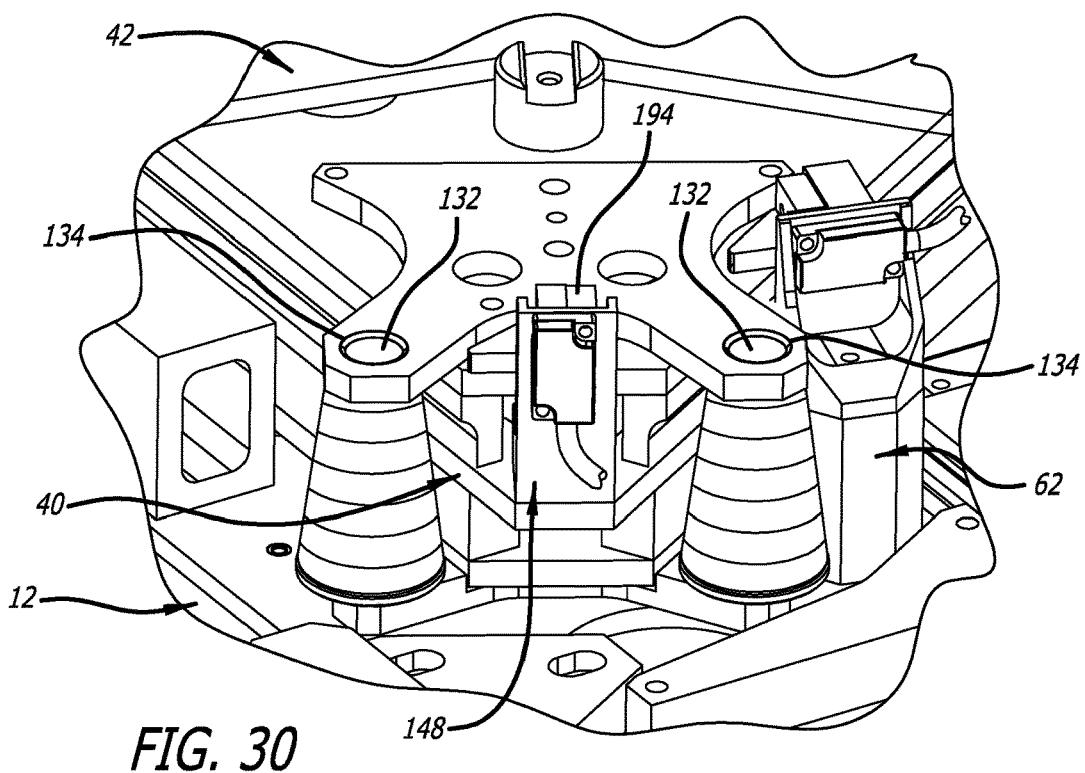
FIG. 30 is an enlarged view of FIG. 25.

FIG. 30 shows two suspension member pins 132 engaged with their respective suspension member receptacles 134 thereby confining the respective suspension member springs 130 between a bottom surface 129 of the top plate assembly 42 and the upper surface 128 of the bottom plate assembly 40, with each suspension member spring 130 providing a restorative force between the top plate assembly 42 and the bottom plate assembly 40. Each resilient suspension member assembly 126 of the bottom plate assembly 40 is thus configured to engage with a respective suspension member receptacle 134 of the top plate assembly 42 in order to provide a type of resilient displaceable suspension between the top plate assembly 42 and the bottom plate assembly 40 with a neutral position that positions the top plate assembly 42 above and parallel to the bottom plate assembly 40. Any motion of the top plate assembly 42 in the Z axis direction 24 away from the neutral position will be resisted by the resilient suspension member assemblies 126 which are operatively engaged with the suspension member receptacles 134.

The bottom plate assembly may also include at least one additional source of rotational motive force such as a piezoelectric motor assembly 136. FIGS. 12 and 13 show three piezoelectric motor assemblies 136 which are secured to the upper surface 128 of the bottom plate assembly 40. The three piezoelectric motor assemblies 136 are radially spaced such that they are substantially equidistant from the central axis 124 of the bottom plate assembly 40, and additionally the three piezoelectric motor assemblies 136 are disposed circumferentially about the central axis 124 of the bottom plate assembly 40 such that they are spaced at an angular separation of about 120 degrees. Each piezoelectric motor assembly 136 may include a piezoelectric motor mount surface 138, and each piezoelectric motor assembly 136 is configured to rotate the piezoelectric motor mount surface 138 relative to the bottom plate body 108 about the central axis 124 of the bottom plate assembly 40.

Figure 36:
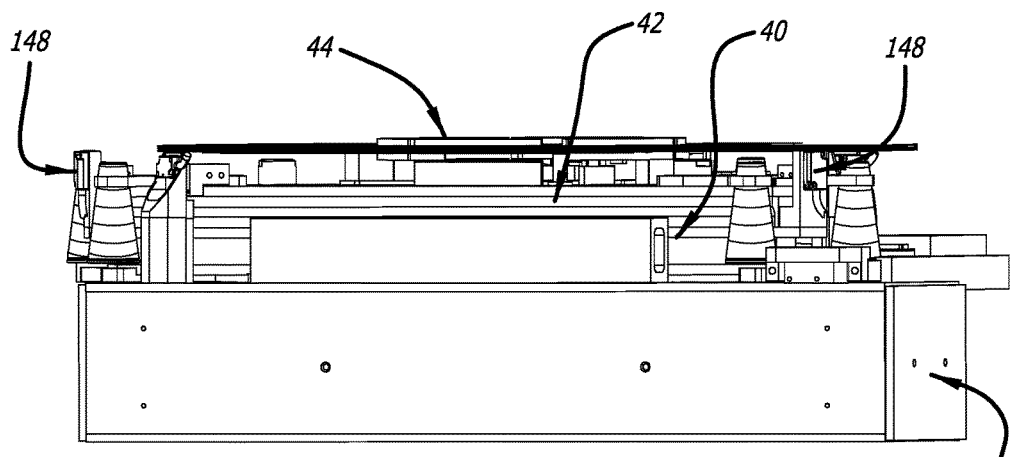
FIG. 36 is an elevation view of the embodiment of FIG. 33.

Additionally each piezoelectric motor assembly 136 may be operatively coupled to the controller system 28 and each piezoelectric motor assembly 136 may include an integral position measurement device which may include a linear encoder or the like. Such an encoder referred to as a piezoelectric motor encoder 140 (not shown), may also be in operative communication with the controller system 28. Each piezoelectric motor encoder 140 may be configured to measure position data of each respective piezoelectric motor mount surface 138 relative to the bottom plate assembly 40. This position data may then be processed by the controller system 28. Each piezoelectric motor assembly 136 may also include a piezoelectric element 141 (not shown) which is configured to expand and contract in a circumferential direction after the application of a voltage across the piezoelectric element 141 from the controller system 28. The three piezoelectric motor assemblies 136 may be operatively coupled to the top plate assembly 42 by the flexure assembly 44 which is shown in FIG. 36. Activation of the three piezoelectric motor assemblies 136 by the controller system 28 will result in the rotation of the top plate assembly 42 in the θ angular direction 26 with respect to the bottom plate assembly 40 with the rotational motive force from the piezoelectric motor assemblies 136 being transmitted to the top plate assembly 42 through the flexure assembly 44. The piezoelectric motor assemblies 136 are configured to provide fine θ axis 26 rotation of the top plate assembly 42 with respect to the bottom plate assembly 40.

The bottom plate assembly may also include at least one Z motor magnet assembly 142. The Z motor magnet assembly 142 is a subcomponent of the Z axis motor assembly 144 which may also include a respective Z motor coil assembly 146 which may be suitably disposed on the top plate assembly 42 (see FIG. 21). The bottom plate assembly embodiment 40 as shown in FIGS. 12 and 13 includes three Z motor magnet assemblies 142 which are secured to the upper surface 128 of the bottom plate assembly 40 and which are radially spaced substantially equidistant from the central axis 124 of the bottom plate assembly 40 (near each apex at an outer edge or perimeter of the triangle shaped bottom plate body 108). Additionally, the three Z motor magnet assemblies 142 are disposed circumferentially about the central axis 124 of the bottom plate assembly 40 such that they are spaced at an angular separation of about 120 degrees. Each Z motor magnet assembly 142 is configured to operatively couple to its respective Z motor coil assembly 146 in order to form the Z axis motor assembly 144 as shown in more detail in FIGS. 22-24. Each Z axis motor assembly 144 is configured to generate Z axis 24 displacement between respective outer portions of the bottom plate assembly 40 and the top plate assembly 42 which is discussed in more detail below referencing FIGS. 26-29.

As has been discussed the motion of the top plate assembly 42 with respect to the bottom plate assembly 40 may be measured with one or more position sensors. The position sensor configurations may include encoders. The multi-axis positioning system 10 includes three Z axis encoder assemblies 147 which are disposed and operatively coupled between the bottom plate assembly 40 and the top plate assembly 42. Each Z axis encoder assembly 147 includes a Z encoder post assembly 148 and Z encoder strip 194. Each Z encoder post assembly includes a Z encoder post 150 and a Z encoder reader 152 which is disposed at a distal end of the Z encoder post 150 and which is operatively coupled to the controller system 28. The bottom plate assembly 40 may include at least one Z encoder post assembly 148.

Figure 47:
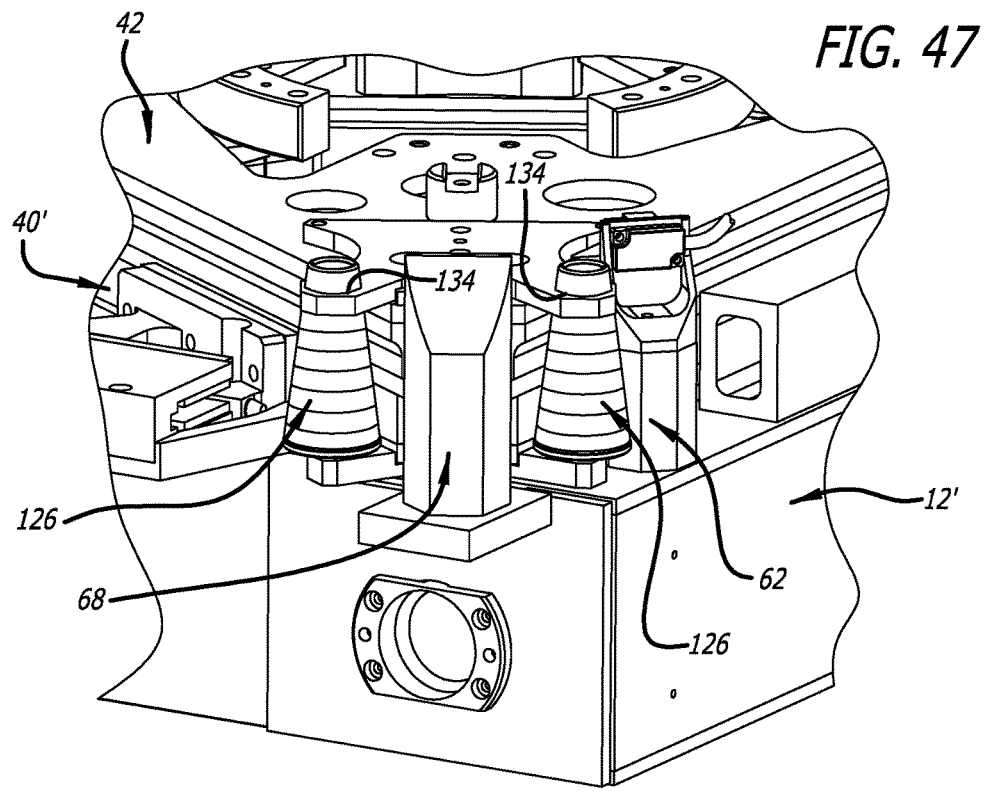
FIG. 47 is an enlarged view of FIG. 46.

FIGS. 12 and 13 depict three Z encoder post assemblies 148 which are radially spaced substantially equidistant from the central axis 124 of the bottom plate assembly 40 (near each apex of the triangle shaped bottom plate body 108). Additionally the Z encoder post assemblies 148 are disposed circumferentially about the central axis 124 of the bottom plate assembly at an angular separation of about 120 degrees. Each Z encoder post 150 may be rigidly secured to and extend from the upper surface 128 of the bottom plate assembly 40. In some cases each Z encoder post may be substantially perpendicular to the upper surface 128 of the bottom plate assembly 40. The extension of the Z encoder posts from the upper surface 128 may be configured to allow for each Z encoder reader 152 to be operatively coupled to each respective Z encoder strip 194 which is rigidly secured to the top plate assembly 42 (see FIG. 18). Each Z encoder strip 194 may be configured to have a scale pitch of about 5 μm to about 20 μm. FIG. 47 also depicts a θ encoder strip 196 of the top plate assembly 42 aligned with a θ encoder post assembly 62 which is secured to the x-y stage assembly 12'. Each θ encoder strip 196 may be configured to have a scale pitch of about 5 μm to about 20 μm.

Figure 18:
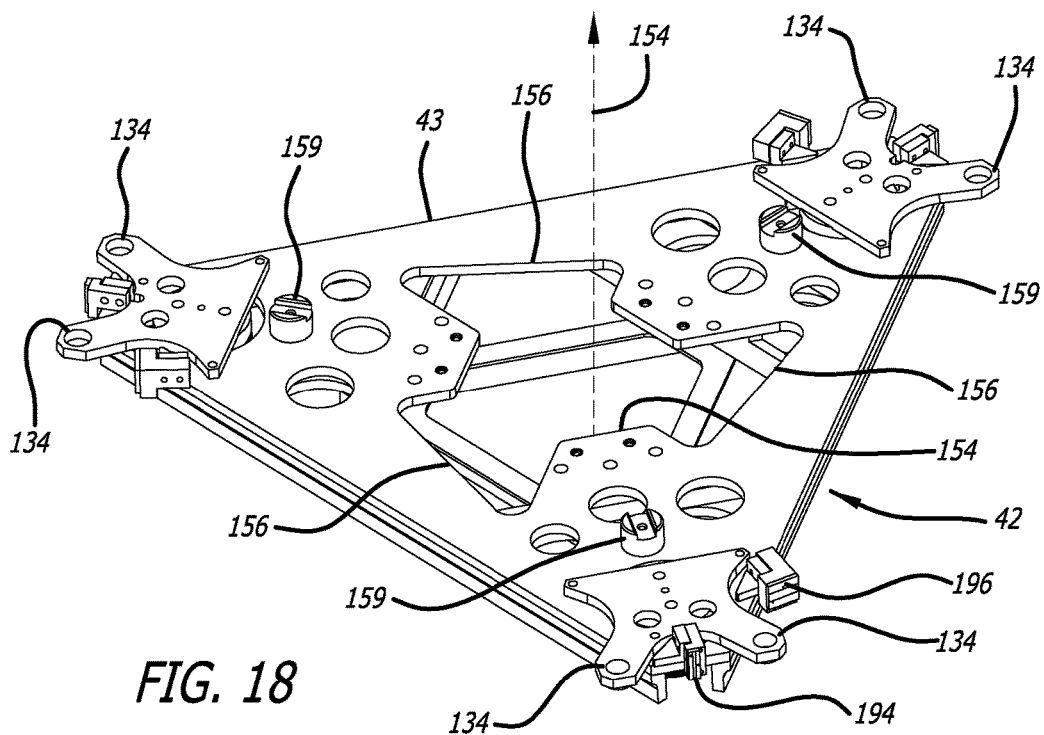
FIGS. 18 and 19 are perspective views of a top plate assembly.
Figure 19:
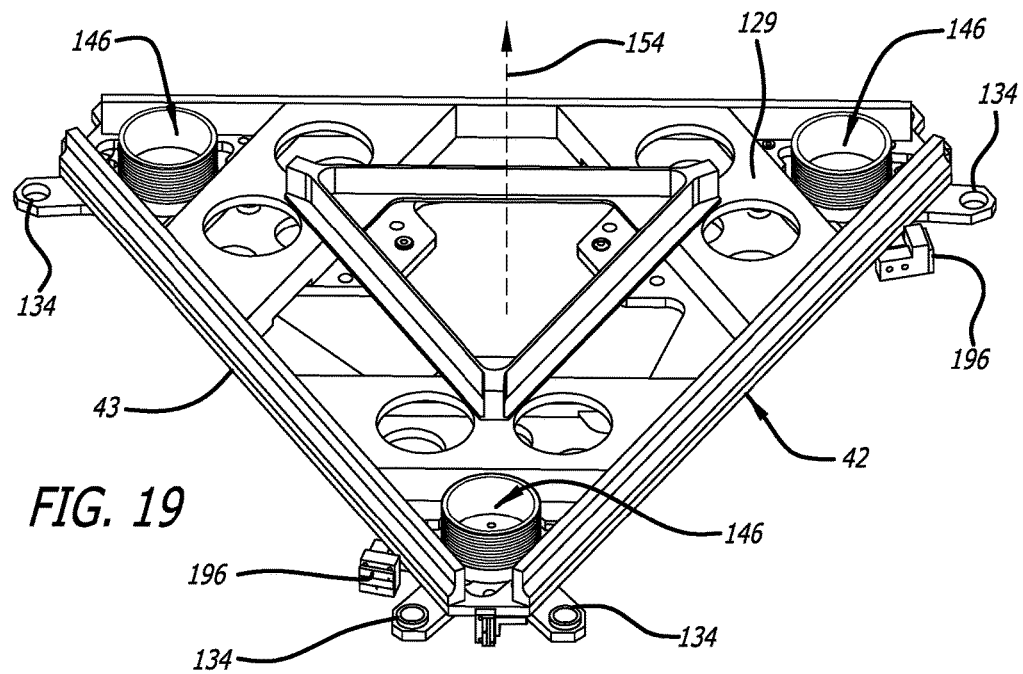
Figure 25:
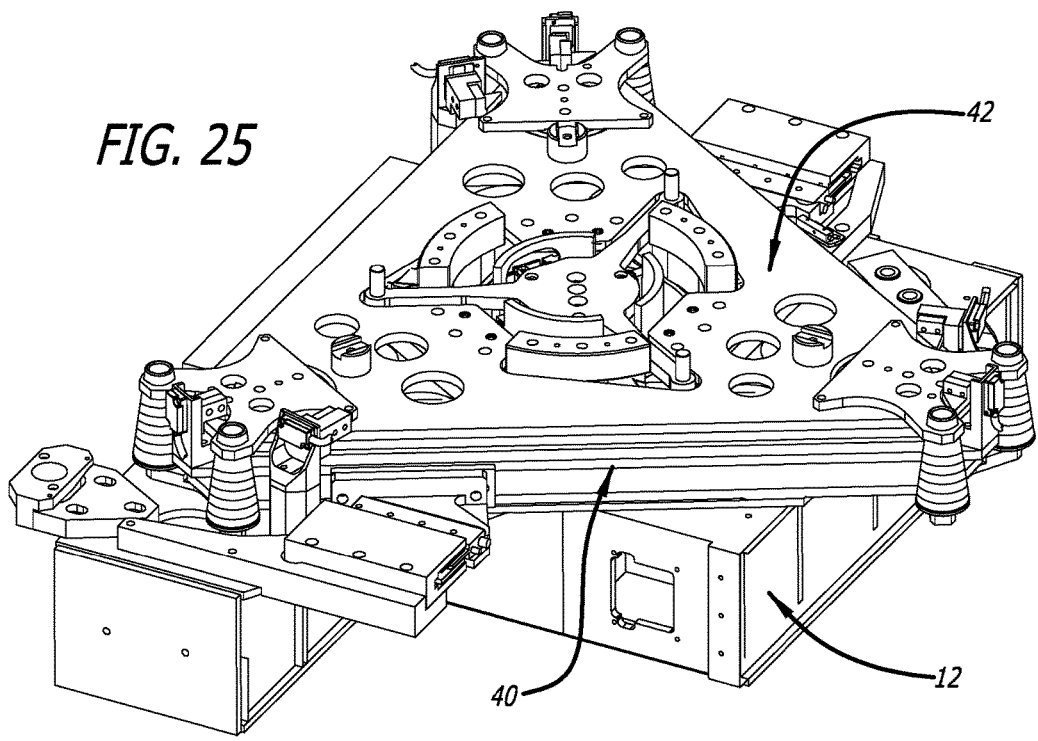
FIG. 25 depicts the top plate embodiment of FIG. 18 coupled to the embodiments shown in FIG. 16 including the x-y stage assembly of FIG. 5, the precision bearing embodiment of FIG. 7, the lift pin ejector embodiment of 9, and the bottom plate assembly embodiment of FIG. 12.

FIGS. 18 and 19 depict the top plate assembly embodiment 42. As has been previously discussed herein, the top plate body 43 of the top plate assembly 42 may be configured in a generally triangular shape and may incorporate a central aperture 154 which is located in the center of the triangle. The top plate assembly 42 may include multiple suspension member receptacles 134 which may be disposed near each apex of the triangle shaped top plate assembly 142. The suspension member receptacles 134 are configured such that they are substantially aligned with the resilient suspension member assemblies 126 of the bottom plate assembly 40 when the top plate assembly 42 is coupled to the bottom plate assembly 40 as is shown in FIG. 25. The central aperture 154 of the top plate assembly 42 includes three radial extensions 156 which are configured to allow clearance of the three piezoelectric motor mount surfaces 138 of the three piezoelectric motor assemblies 136 when the bottom plate assembly 40 is coupled to the top plate assembly 42 (see FIG. 25). The top plate assembly may also include three chuck mounts 159.

Figure 21:
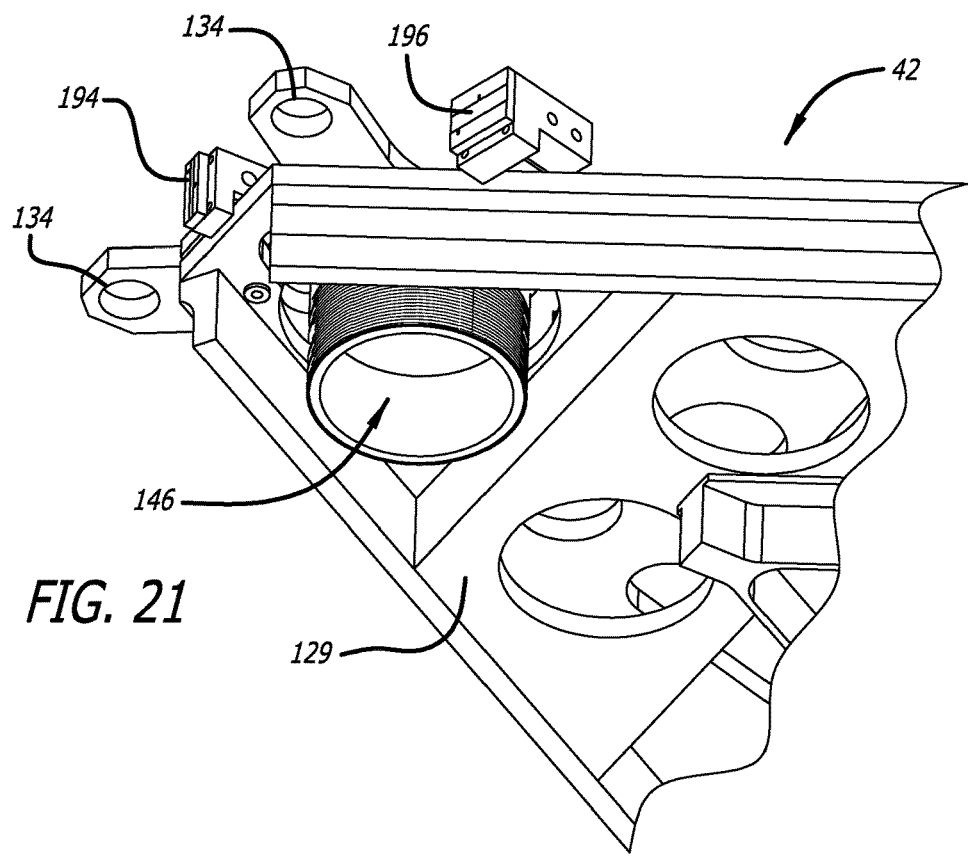
FIG. 21 is an enlarged view of the top plate assembly of FIG. 18 showing a Z axis motor coil assembly and multiple suspension member mounts.
Figure 22:
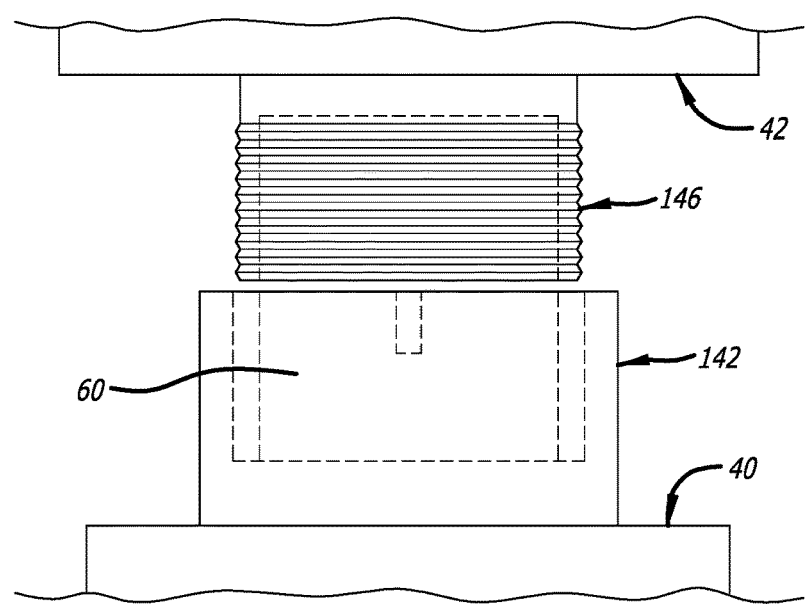
FIGS. 22-24 are hidden lines views of a Z axis motor assembly which includes a Z motor coil assembly and a Z motor magnet assembly.

The top plate assembly 42 may also include at least one Z motor coil assembly 146 (see FIG. 21). The top plate assembly embodiment 42 as shown in FIGS. 21 and 22 includes three Z motor coil assemblies 146 which are disposed on the top plate body 43 such that they are substantially radially equidistant from the central axis 154 of the top plate assembly 42. Additionally, the Z motor coil assemblies 146 are disposed circumferentially about the central axis 154 of the top plate assembly 42 at an angular separation of about 120 degrees. As discussed previously, the Z motor coil assemblies 146 are subcomponents of the Z axis motor assemblies 144 which also include the Z motor magnet assemblies 142 (see FIG. 20). When they are operatively coupled together (that is when the top plate assembly 42 is coupled to the bottom plate assembly 40) the Z motor magnet assemblies 142 and the Z motor coil assemblies 146 form the Z axis motor assemblies 144 which are configured as electromagnetic voice coil motors but any other suitable type of motor could be used.

Figure 23:
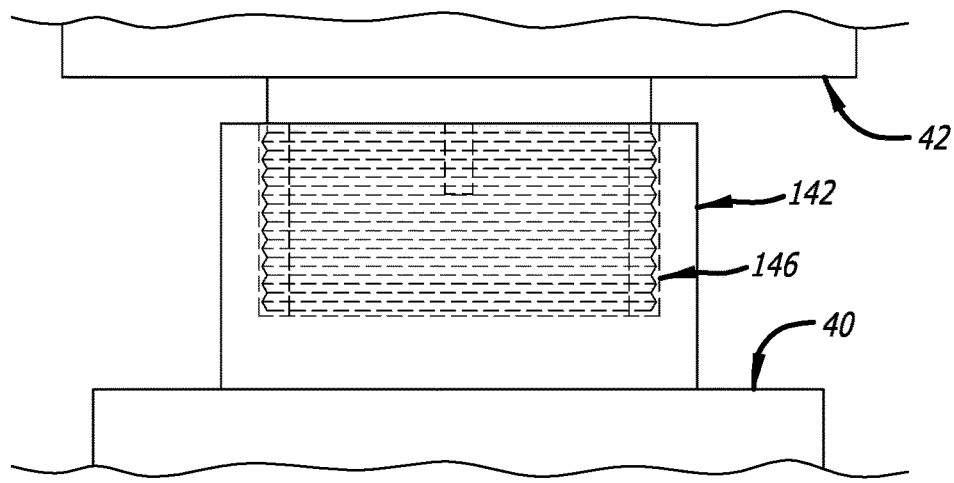
Figure 24:
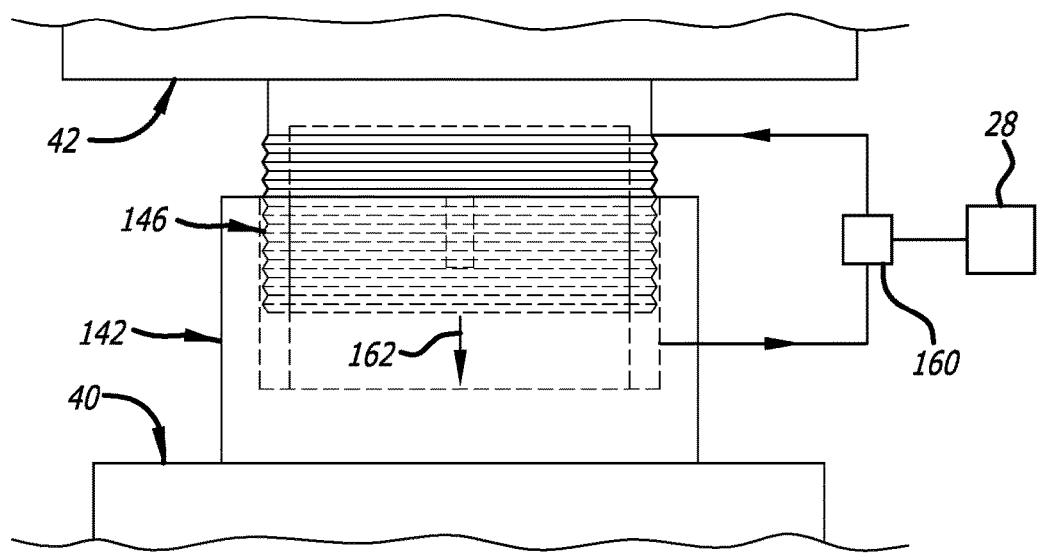

Each Z axis motor assembly 144 is operatively coupled to the controller system 28. FIGS. 22-24 illustrate an embodiment of a Z axis motor assembly 144 which depict a Z motor magnet assembly 142, a Z motor coil assembly 146, the top plate assembly 42, and the bottom plate assembly 40. FIG. 22 depicts the Z motor magnet assembly 142 completely decoupled from the Z motor coil assembly 146. FIG. 23 depicts the Z motor coil assembly 146 operatively engaged with the Z motor magnet assembly 142. FIG. 24 depicts a current supply 160 being activated by the controller system 28 thereby providing current to the Z motor coil assembly 146. This creates a magnetic field which in turn causes a Z axis motion (as indicated by arrow 162) of the upper plate assembly 42 with respect to the bottom plate assembly 40. Other possible embodiments of the multi-axis positioning system 10 may include configurations wherein the Z motor magnet assemblies 142 are disposed on the top plate assembly 42 and the Z motor coil assemblies 146 are disposed on the bottom plate assemblies 40. FIG. 25 depicts the top plate assembly 42 coupled to the bottom plate assembly embodiment 40 which is in turn coupled to the x-y stage assembly embodiment 12. The upper plate assembly 42 is coupled to the bottom plate assembly 42 by the flexure assembly 44 as will be discussed below.

Figure 26:
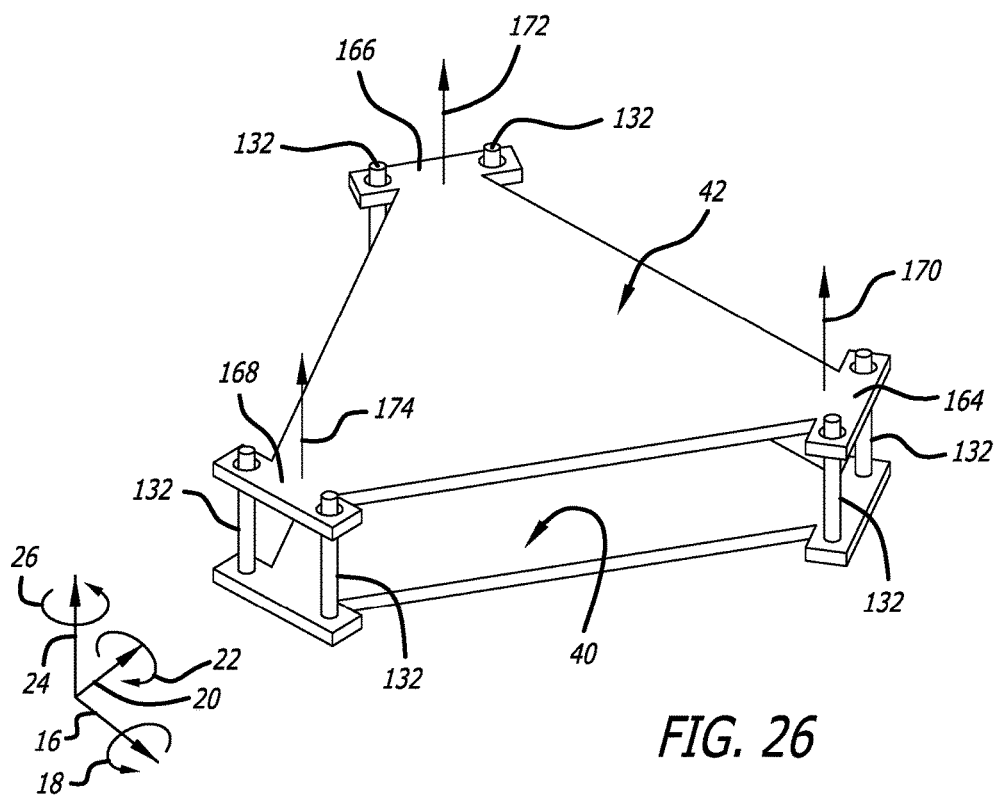
FIGS. 26-29 depict the motions of a top plate embodiment with respect to a bottom plate embodiment.

FIGS. 26-29 are intended to illustrate several (but not all) possible motions of the top plate assembly 42 with respect to the bottom plate assembly 40, with each possible motion being caused by the selective activation of the Z axis motor assemblies 142 by the controller system 28. FIG. 26 depicts schematic representations of the top plate assembly 42 and of the bottom plate assembly 40 which includes multiple suspension member pins 132 which are shown to provide a stationary reference to illustrate the motion of the top plate assembly 42 with respect to the bottom plate assembly 40. The Z axis motor assemblies 142 and suspension member coils 130 are not shown in FIGS. 26-29 (nor are other sub-components of the bottom plate assembly 40 and the top plate assembly 42) for purposes of clarity, but it is understood that the Z axis motor assemblies 144 provide the Z axis 24 motion of the top plate assembly 42 and the suspension member coils 130 oppose the Z axis 24 motion of the top plate assembly 42. That is the suspension member coils 130 provide a restorative force to a neutral position of the top plate assembly 42. After the Z axis motor assemblies 144 move the top plate assembly 42 from a neutral position with respect to the bottom plate assembly 40 this restorative force will return the top plate assembly 42 to the neutral position again once the Z axis motor assemblies 144 are turned off.

The top plate assembly 42 may include a first apex section 164, a second apex section 166, and a third apex section 168. The Z axis motor assemblies 144 (again not shown, see FIG. 27 for reference) are capable of translating each apex section along the Z axis 24 in either direction, and any of the translations depicted in the FIGS. 26-29 are assumed to be carried out by the Z axis motor assemblies 144. FIG. 26 depicts translation of the first apex section 164 in the positive Z axis direction 26 as indicated by arrow 170, motion of the second apex section 166 along the positive Z axis 24 as indicated by arrow 172, and motion of the third apex section 168 along the positive Z axis 24 as indicated by arrow 174. FIG. 26 thus depicts the translation of the top plate assembly 42 (with respect to the bottom plate assembly 40) along the positive Z axis 24 wherein the top plate assembly 42 is oriented such that it is substantially parallel to a plane which is formed by the X axis 16 and the Y axis 20. The top plate assembly 42 could also be translated (by the Z axis motor assemblies 144) in the negative Z axis 24 direction while the top plate assembly 42 remains oriented such that it is substantially parallel to the plane which is formed by the X axis 16 and the Y axis 20.

Figure 27:
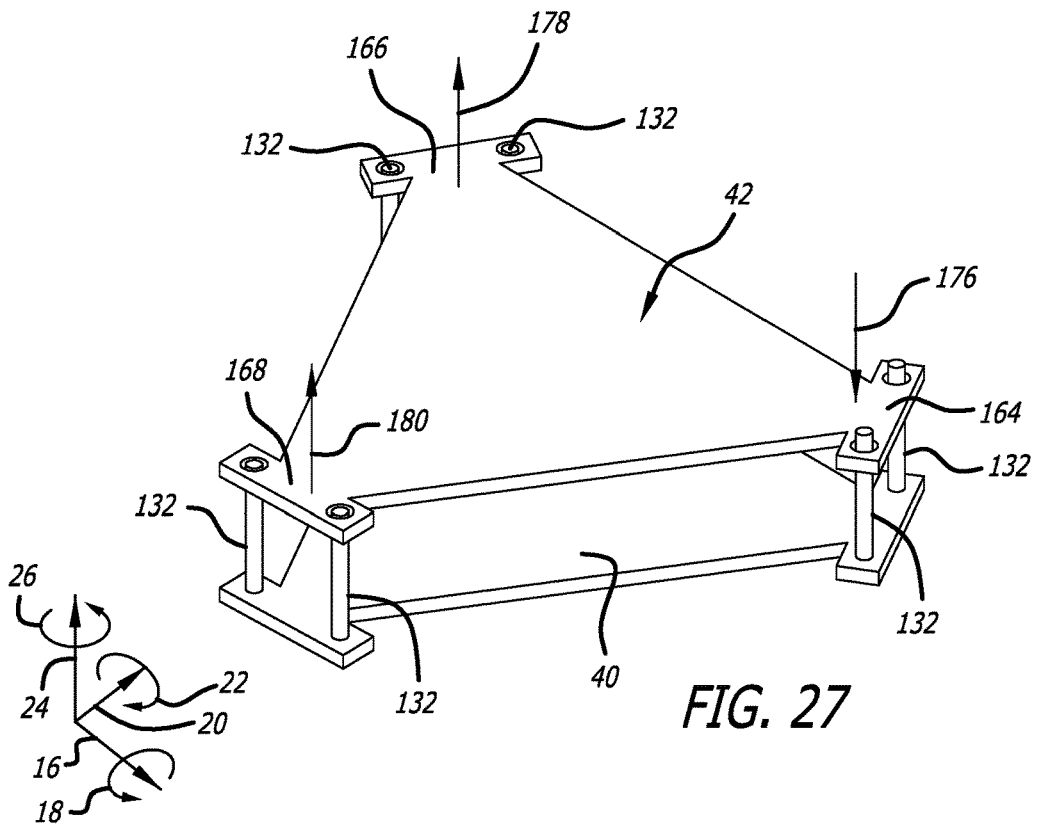
Figure 28:
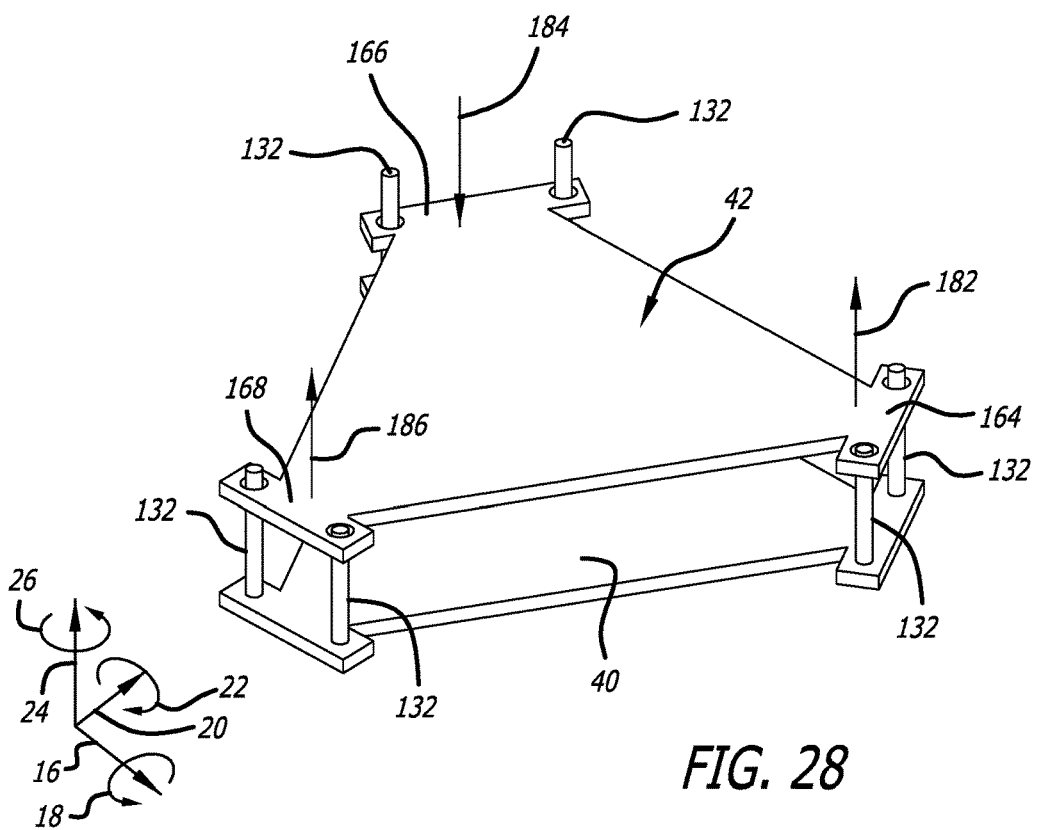

FIG. 27 depicts translation of the first apex section 164 along the negative Z axis direction as indicated by arrow 176, motion of the second apex section 166 along the positive Z axis 24 as indicated by arrow 178, and motion of the third apex section 168 along the positive Z axis 24 as indicated by arrow 180. This results in a "rotation" of the top plate assembly 42 with respect to the bottom plate assembly 40, with the total rotational motion of the top plate assembly 42 including a component of rotational motion about the Tilt axis 18 and a component of rotational motion about the Tip axis 22. FIG. 28 depicts translation of the first apex section 164 along the positive Z axis direction 24 as indicated by arrow 82, motion of the second apex section 166 along the negative Z axis 24 as indicated by arrow 184, and motion of the third apex section 168 along the positive Z axis 24 as indicated by arrow 186. This results in a "rotation" of the top plate assembly 42 with respect to the bottom plate assembly 40, with the total rotational motion of the top plate assembly 42 including a component of rotational motion about the Tilt axis 18 and a component of rotational motion about the Tip axis 22.

Figure 29:
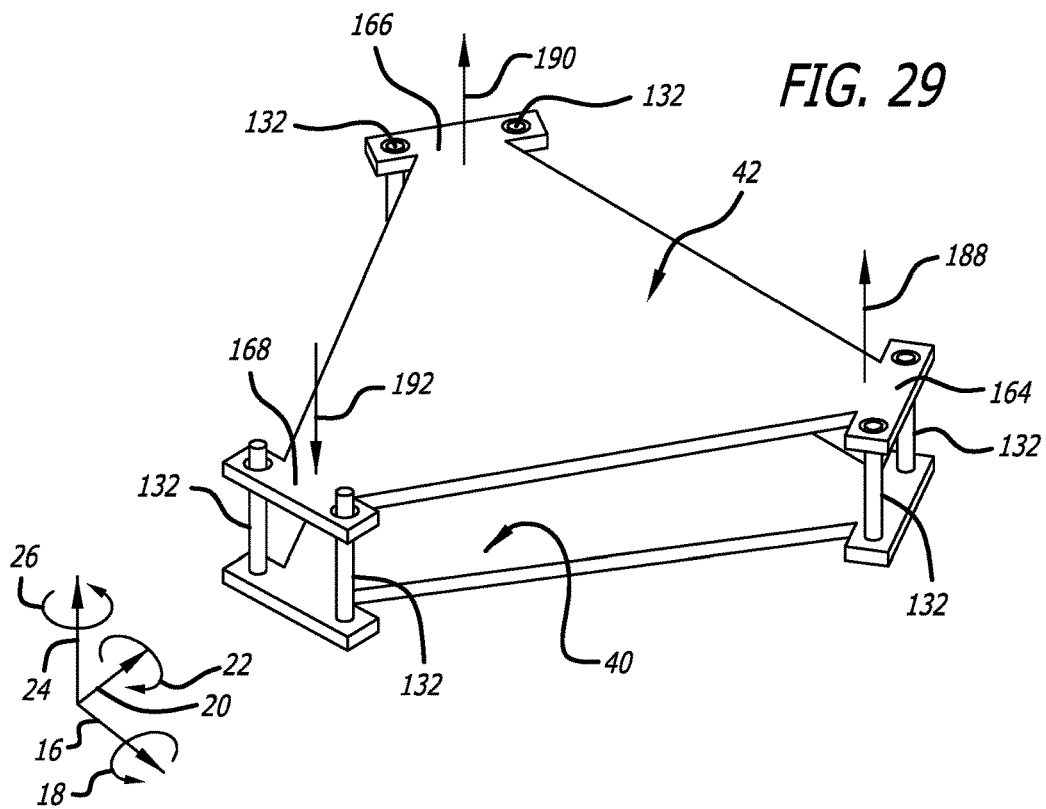

FIG. 29 depicts translation of the first apex section 164 along the positive Z axis direction 24 as indicated by arrow 188, motion of the second apex section 166 along the positive Z axis 24 as indicated by arrow 190, and motion of the third apex section 168 along the negative Z axis 24 as indicated by arrow 192. This results in a "rotation" of the top plate assembly 42 with respect to the bottom plate assembly 40, with the total rotational motion of the top plate assembly 42 including a component of rotational motion about the Tilt axis 18 and a component of rotational motion about the Tip axis 22. It should be noted that any permutation and or combination of the motions of the first apex section 164, the second apex section 166, and the third apex section 168 which have been discussed are allowable with respect to the translation and/or rotation of the top plate assembly 42 with respect to the bottom plate assembly 40.

FIG. 30 is an enlarged view of FIG. 25 which depicts a portion of the top plate assembly 42 coupled to the lower plate assembly embodiment 40 which is in turn coupled to the x-y stage assembly embodiment 12. As shown in FIGS. 18 and 19, the top plate assembly 42 may also include multiple Z encoder strips 194 and multiple θ encoder strips 196. For the top plate assembly embodiment 42 shown, three Z encoder strips 194 are disposed at each apex of the top plate body 43, with each Z encoder strip 194 being configured such that it aligned with its respective Z axis encoder post assembly 148 when the top plate assembly 42 is coupled to the bottom plate assembly 40 as shown in FIG. 30. Each Z encoder reader 152 can then read Z axis 24 position data of the top plate assembly 42 from its respective Z encoder strip 194. The top plate assembly 42 may also include multiple θ encoder strips 196. For the top plate embodiment 42 shown in FIGS. 18 and 19, three θ encoder strips 196 are disposed near each apex of the top plate body 43, with each θ encoder strip 196 being configured such that it aligned with its respective θ encoder post assembly 62 when the top plate assembly 42 is coupled to the bottom plate assembly 40 as shown in FIG. 30. Each θ encoder reader 152 can then read θ axis 26 position data of the top plate assembly 42 from its respective θ encoder strip 194.

Figure 31:
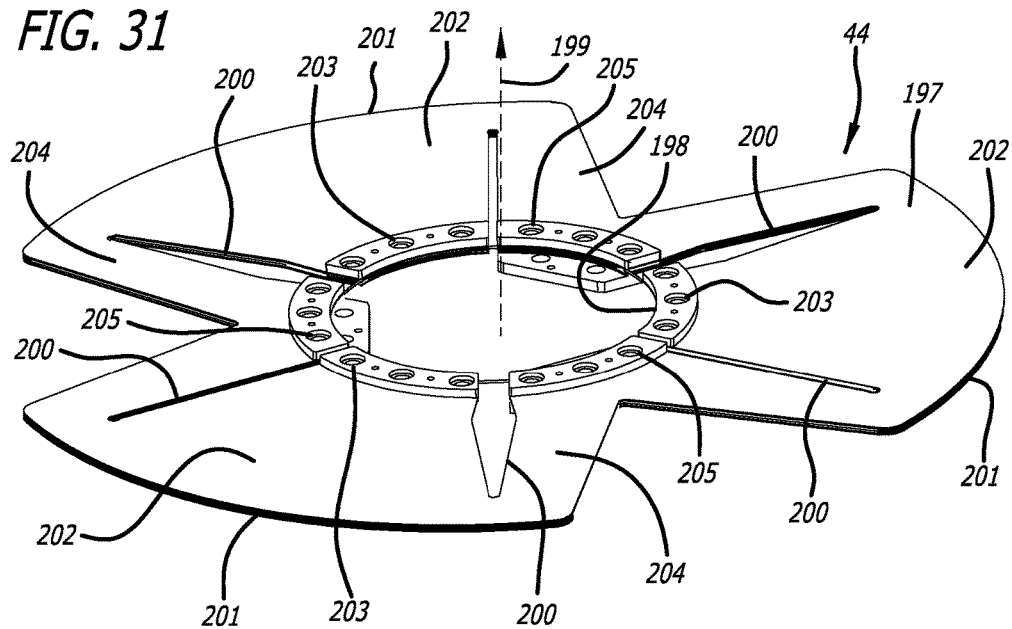
FIG. 31 is a perspective view of flexure assembly including fixed flexure sections and moveable flexure sections.
Figure 32:
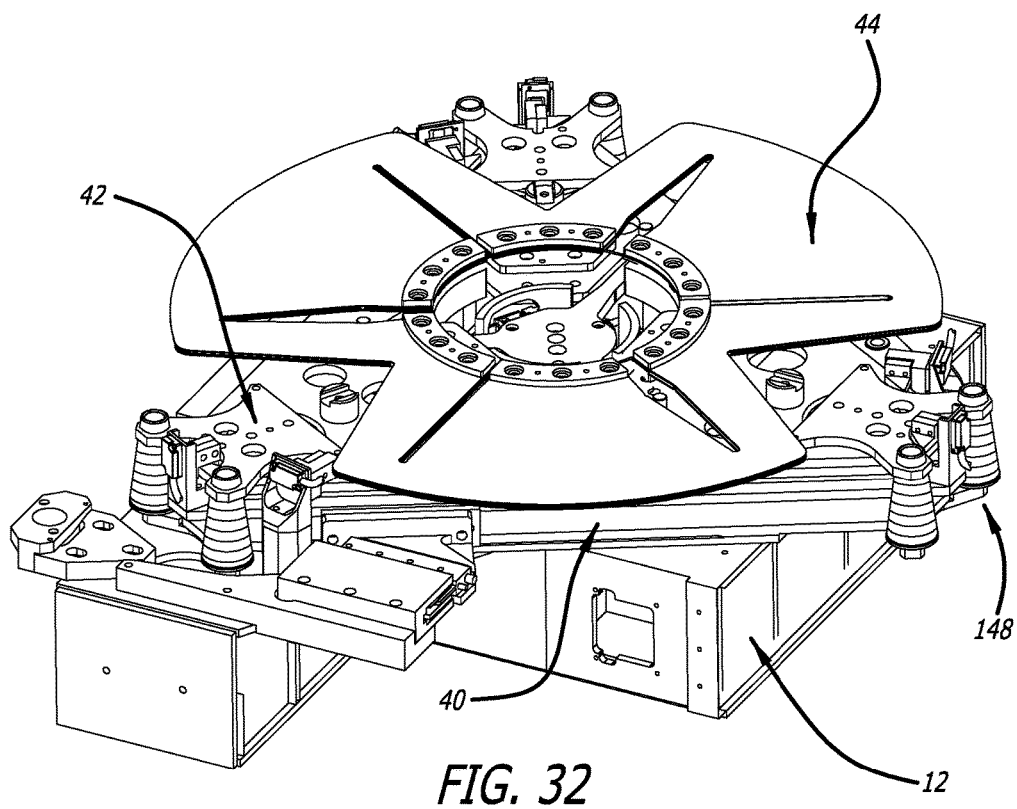
FIG. 32 depicts the flexure assembly of FIG. 31 coupled to the embodiments which are shown in FIG. 25.

The thin slotted flexure assembly 44 may include a flexure body 197 and may be coupled between the bottom plate assembly 40 and the top plate assembly 42 as shown in FIG. 31. The slotted flexure assembly 44 may incorporate a central aperture 198 which has a central axis 199. The flexure assembly 44 may also include a plurality of slots 200 which extend radially from the central axis 199 and central aperture 198 and which terminate inwardly of an outer radial edge 201 of the flexure body 197. For some embodiments, six such slots 200 extend radially from the central aperture 198 with slots separated by an angle of about 60 degrees. The six slots 198 delineate and separate three fixed flexure sections 202 of the flexure assembly 44 from three moving flexure sections 204 of the flexure assembly 44. Each fixed flexure section 202 may be circumferentially adjacent to each moving flexure section 204. The three fixed flexure sections 202 may incorporate three fixed flexure fixations 203, and the three moving flexure sections may incorporate three moving flexure fixations 205.

Figure 33:
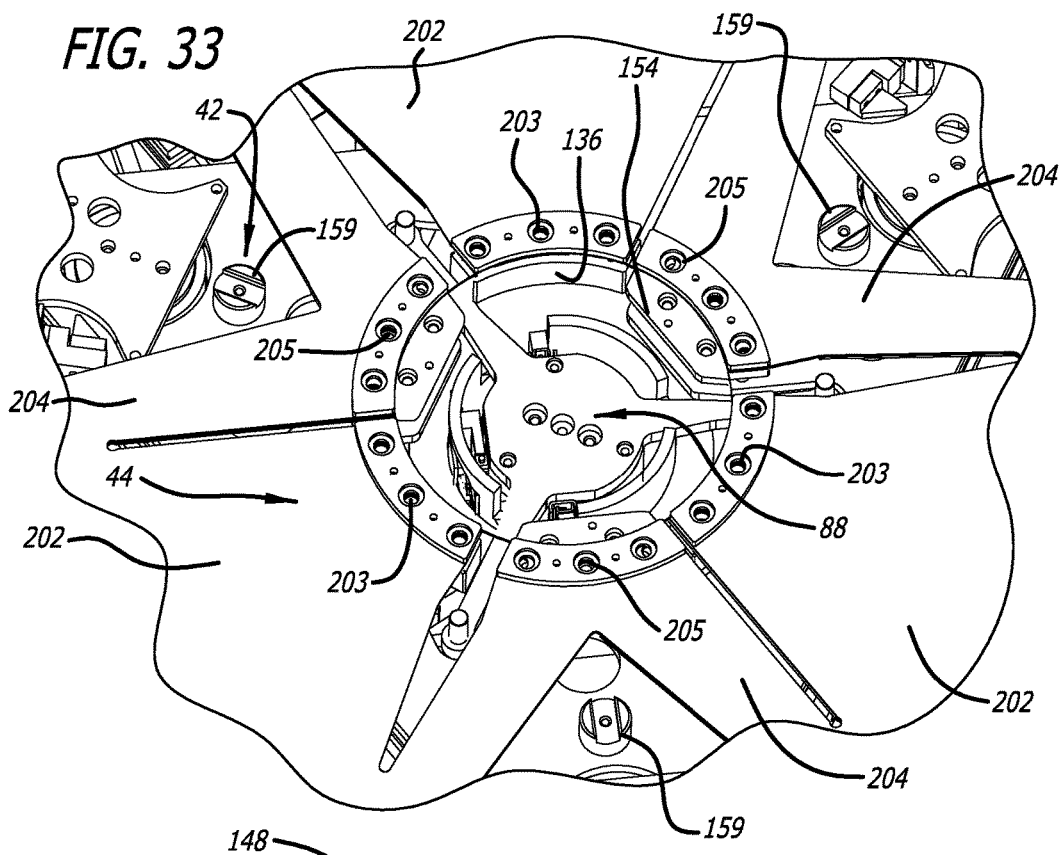
FIG. 33 is an enlarged view of FIG. 32 showing multiple chuck assembly mounts.
Figure 34:
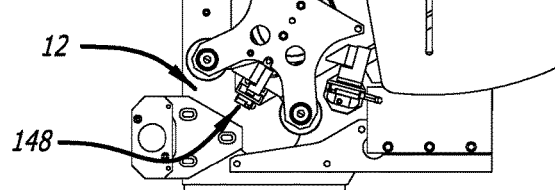
FIG. 34 is an elevation view of the embodiment of FIG. 33.
Figure 35:
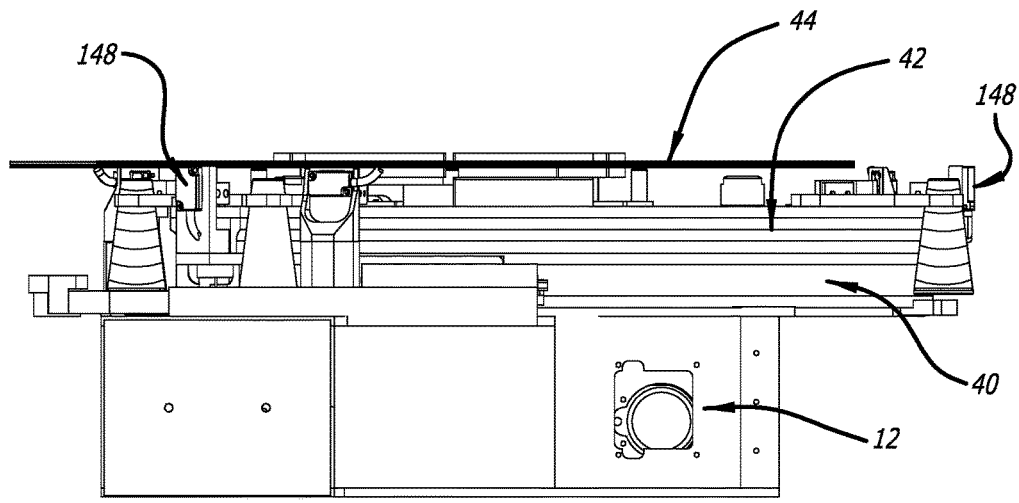
FIG. 35 is an elevation view of the embodiment of FIG. 33.

The three fixed flexure fixations 203 may be secured (by the use of fasteners which are not shown) to the three piezoelectric motor mount surfaces 138 and the three moving flexure fixations 205 may be secured (by the use of fasteners which are not shown) along the central aperture 154 of the top plate assembly 42 as shown in FIG. 33. In this manner, the three fixed flexure sections 202 are coupled to the three piezoelectric motor assemblies 136 which are secured to the bottom plate assembly 40. The three piezoelectric motor assemblies 136 can thereby induce rotational motion in the θ angular direction 26 of the piezoelectric motor mount surfaces 138 which in turn rotates the flexure assembly 44 in the θ angular direction 26. The rotation of flexure assembly 44 in the θ angular direction 26 in turn causes rotation of the top plate assembly 42 to rotate in the θ angular direction 26. The flexure assembly 44 thus functions as a drive coupling between the bottom plate assembly 40 and the top plate assembly 42 that efficiently transmits torque in a θ angular direction 26 from the bottom plate assembly 40 to the top plate assembly 42 but also effectively isolates the bottom plate assembly 40 from the top plate assembly 42 for motion of the top plate assembly 42 in a Z axis 24 direction. With this arrangement, fine θ adjustment between the bottom plate assembly 40 and the top plate assembly 42 can be carried out with the piezoelectric motor assemblies 136 without substantially affecting the Z axis 24 position of the top plate assembly 42. The flexure assembly 44 allows for the translation of the top plate assembly 42 with respect to the bottom plate assembly 40 along the Z axis 24, and for the rotation of the top plate assembly 42 with respect to the bottom plate assembly 40 in the Tip angular direction 22 and in the Tilt angular direction 18.

The flexure assembly 44 may be fabricated as a multi-layered composite that is it may incorporate several different layers of different materials. The materials which form the flexure assembly 44 may include any suitable metal, any suitable fabric, or any suitable polymer. For example, steel such as stainless steel and fabric such as scotch damp may comprise some of the layers which form the multi-layered composite of the flexure assembly.

FIGS. 32-36 illustrate the flexure assembly 44 coupled to the sub-assembly shown in FIG. 25 which includes the x-y stage assembly 12, the bottom plate assembly 40, and the top plate assembly 42. FIG. 1 shows an embodiment of a complete ZTTT assembly 14 which also includes the chuck assembly 46. The chuck assembly may include chuck mounting holes (not shown) which are disposed on the chuck body 48, with the chuck mounting holes being configured such that they align with chuck mounts 159 of the top plate body 43 which are shown in FIG. 33. The chuck assembly 46 may be secured to the top plate assembly 42 with the use of fasteners (not shown) which may be used in order to connect the chuck mounts 159 of the top plate assembly 42 to the chuck mounting holes of the chuck body 48. The chuck assembly 46 also includes ejector pin through holes 208 which allow for the lift pins 92 of the lift pin ejector assembly 88 to pass through the chuck body 48 and contact the specimen 220 in order to eject the specimen 220 from the chuck assembly 46.

Figure 37:
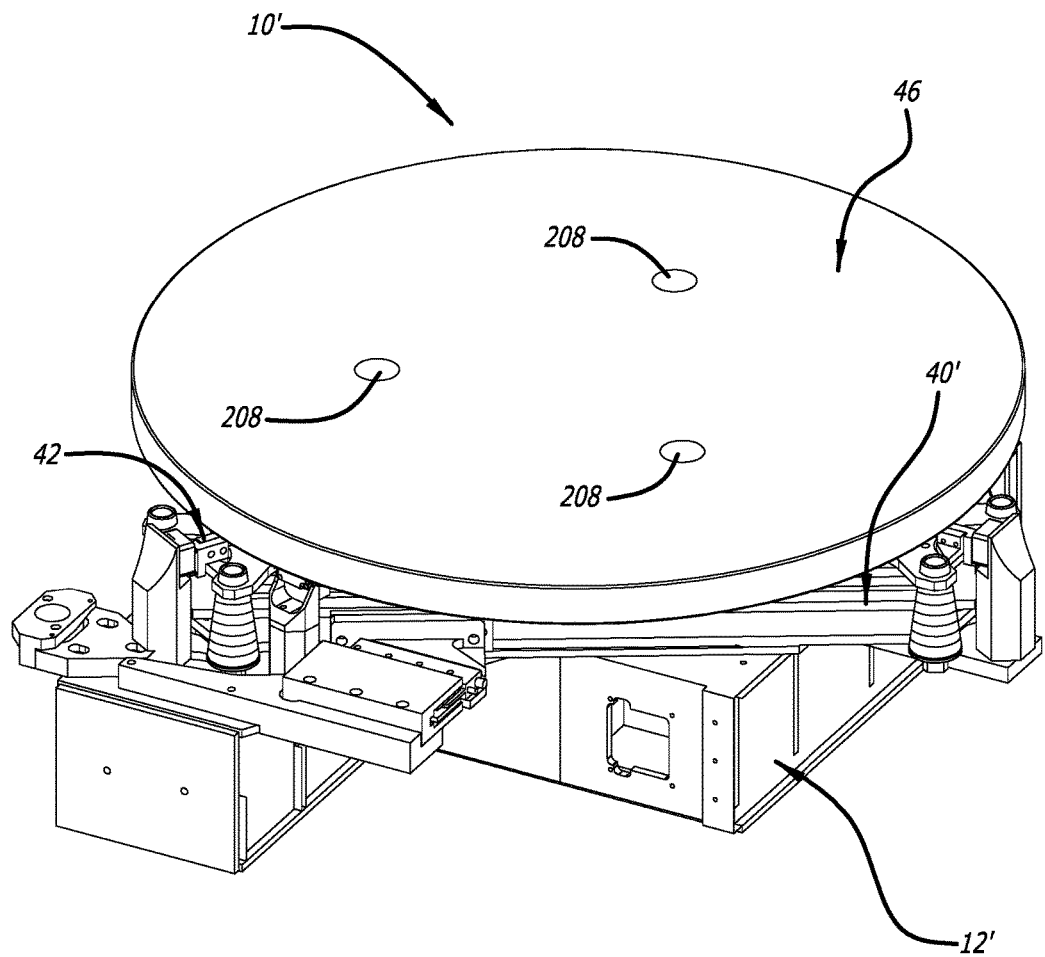
FIG. 37 is a perspective view of a multi-axis positioning system.
Figure 38:
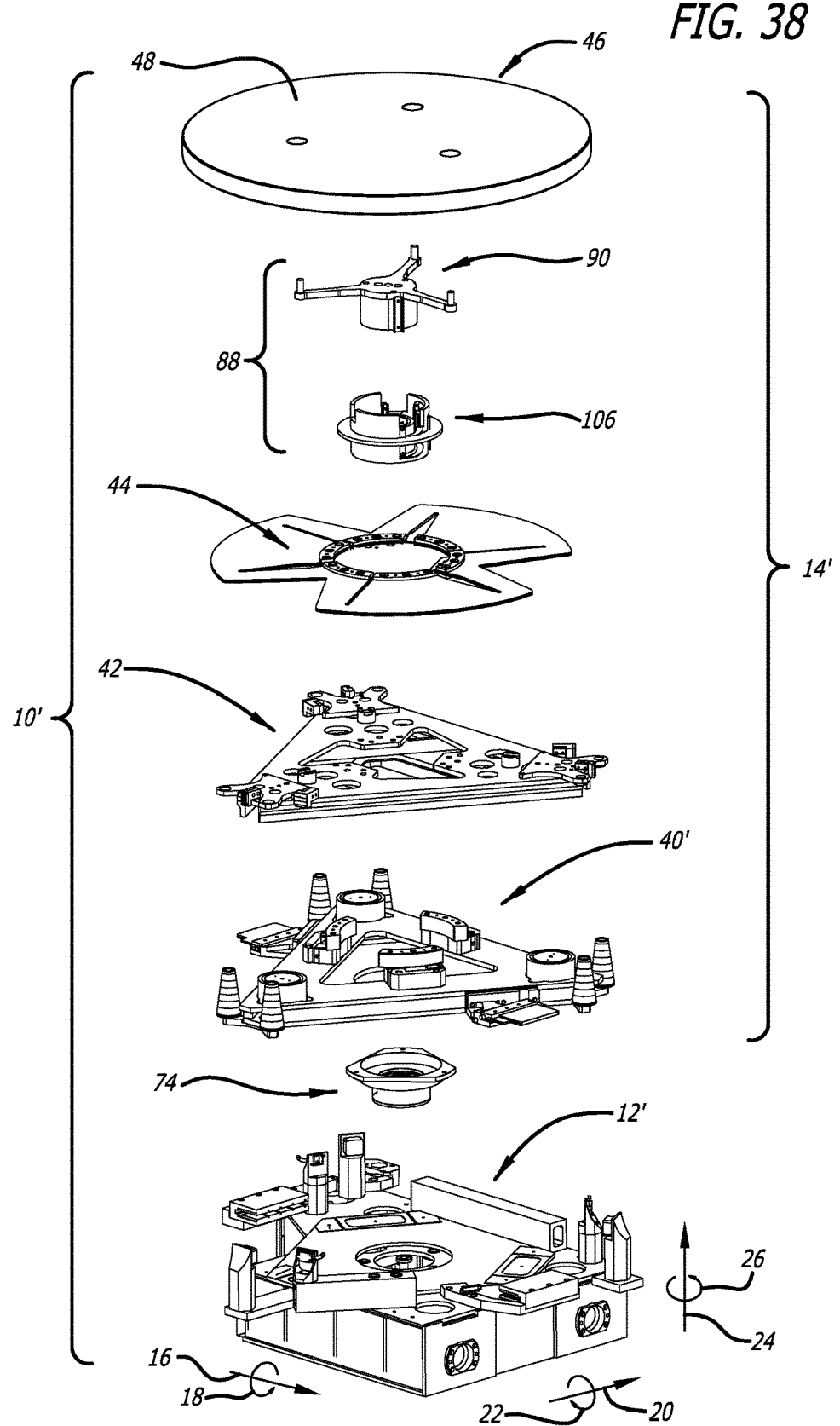
FIG. 38 is an exploded view of the multi-axis positioning system of FIG. 37.

Another embodiment of a multi-axis positioning system 10' is depicted in FIGS. 37-48. The multi-axis positioning system 10' may be configured such that it is substantially similar to the multi-axis positioning embodiment 10 which has been previously discussed herein. The multi-axis positioning system 10' may include an x-y stage assembly 12' and a ZTTT assembly 14' which may be operatively coupled to the x-y stage assembly 12'. The ZTTT assembly 14' may include a chuck assembly 46, a lift pin ejector assembly 88, a flexure assembly 44, a top plate assembly 42, a bottom plate assembly 40', and a precision bearing assembly 74 all of which are shown in FIG. 38. The difference between the multi-axis positioning system 10' and the multi-axis positioning system 10 is that the multi-axis positioning system 10' incorporates multiple Z axis encoder assemblies 67 which are disposed and operatively coupled between the x-y stage assembly 12' and the top plate assembly 42. As has been previously discussed, the multi-axis positioning system 10 includes multiple Z axis encoder assemblies 147 which are disposed and operatively coupled between the bottom plate assembly 40 and the top plate assembly 42 (see FIG. 4).

Other than the difference in the location of the respective Z axis encoder assembly sub-assemblies, the multi-axis positioning system embodiment 10' is configured such that it is substantially similar to the multi-axis positioning system 10 which has been discussed herein. Each of the following sub-assemblies (and respective sub-assemblies thereof) of the multi-axis positioning system 10 which have been previously discussed including the top plate assembly 42, the flexure assembly 44, the chuck assembly 46, the precision bearing assembly 74, the lift pin ejector assembly 88, may be configured and function within the multi-axis positioning system 10' in a manner which is analogous to the way that each of the sub-assemblies are configured and function within the multi-axis positioning system 10.

The multi-axis positioning system 10' also includes the following sub-assemblies (and respective sub-assemblies thereof) each of which may be configured and operate within the multi-axis positioning system 10' in a manner which is analogous to the way in which each respective sub-assembly is configured and operates within multi-axis positioning system 10: multiple passive reference surfaces 114 and active reference surfaces 50 (and sub-assemblies thereof) which are disposed and operatively coupled between the x-y stage assembly 12' and the bottom plate assembly 40' (see FIGS. 14 and 15), multiple θ motor assemblies 58 which are disposed and operatively coupled between the x-y stage assembly 12' and the bottom plate assembly 40' (see FIG. 46), multiple θ encoder assemblies 61 which are disposed and operatively coupled between the x-y stage assembly 12' and the top plate assembly 42 (see FIGS. 39 and 40), multiple resilient suspension member assemblies 126 and suspension member receptacles 134 which are disposed and operatively coupled between the bottom plate assembly 40' and the top plate assembly 42 (see FIG. 47), and multiple Z axis motor assemblies 144 which are disposed and operatively coupled between the bottom plate assembly 40' and the top plate assembly 42 (see FIGS. 22-24).

Figure 39:
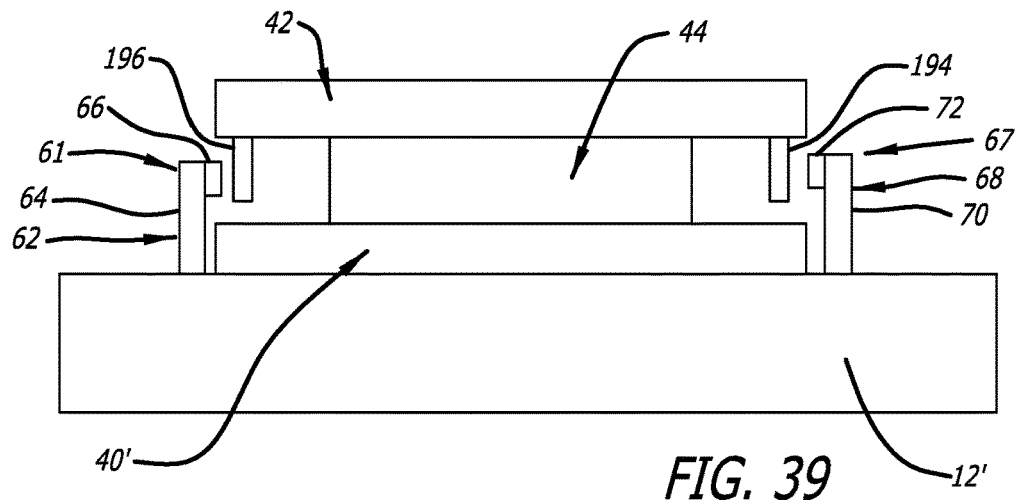
FIG. 39 is a two dimensional block diagram of a multi-axis positioning system of FIG. 38.

As discussed above the multi-axis positioning system 10' may incorporate multiple position sensors. Some position sensor embodiments may include optical encoders which may be used to measure the position of the top plate assembly 42 relative to other sub-components of the multi-axis positioning system 10'. The optical encoders of the multi-axis positioning system 10' may include Z axis encoder assemblies 67 and θ encoder assemblies 61. FIG. 39 is a two dimensional block diagram showing representations of several sub-assemblies of the multi-axis positioning system 10', as well as representations of sub-assemblies of a Z axis encoder assembly 67 and θ encoder assembly 61. The block diagram shown in FIG. 39 does not in general accurately depict the relative size or shape of each sub-assembly which is depicted in the block diagram; the block diagram is intended to illustrate the position of the encoder assemblies with respect to each sub-assembly of the multi-axis positioning system 10' which is depicted in the block diagram.

FIG. 39 depicts representations of an x-y stage assembly 12', a bottom plate assembly 40', a flexure assembly 44, a top plate assembly 42, sub-assemblies of a θ optical encoder assembly 61, and sub-assemblies of a Z axis encoder assembly 61. The θ optical encoder assembly 61 includes a θ encoder strip 196 and a θ encoder post assembly 62 which includes a θ encoder post 64 and a θ encoder reader 66. As can be seen in the block diagram, the θ optical encoder assembly 61 is disposed and operatively coupled between the x-y stage assembly 12' and the top plate assembly 42. The θ encoder assembly 61 is configured to measure the θ axis 26 angular displacement of the top plate assembly 42 with respect to the x-y stage assembly 12' when the θ encoder reader 66 measures θ axis 26 position data from the θ encoder strip 196 which is rigidly secured to the top plate assembly 42. The Z axis encoder assembly 67 includes a Z encoder strip 194 and a Z encoder post assembly 68 which in turn includes a Z encoder post 70 and a Z encoder reader 72. The Z axis encoder assembly 67 is disposed and operatively coupled between the x-y stage assembly 12" and the top plate assembly 42. The Z axis encoder assembly 67 is configured to measure the Z axis 24 displacement of the top plate assembly 42 with respect to the x-y stage assembly 12' when the Z encoder reader 72 measures Z axis 24 position data from the Z encoder strip 194 which is secured to the top plate assembly 42.

Figure 40:
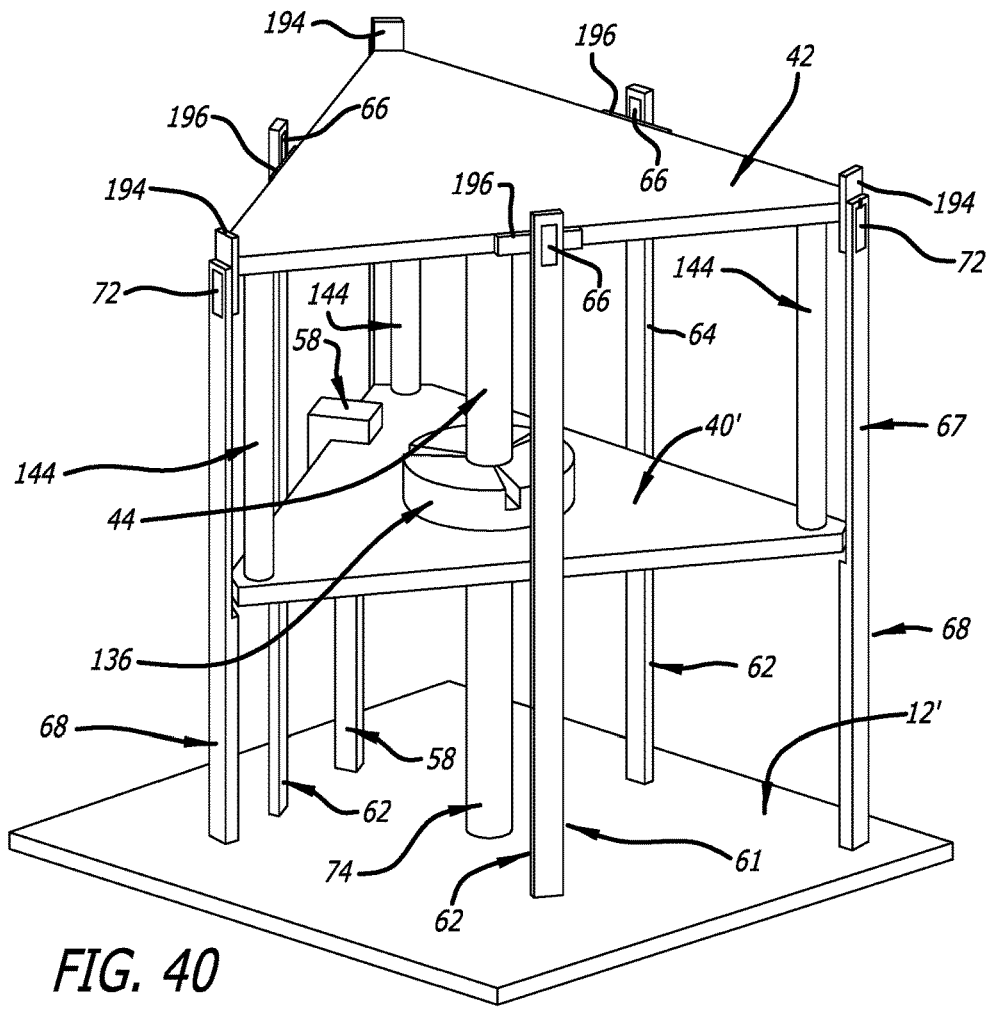
FIG. 40 is a three dimensional block diagram of the multi-axis positioning system of FIG. 38.

FIG. 40 is a three dimensional block diagram of the multi-axis positioning system 10' of FIG. 37 which is intended to further clarify the position of the encoder assemblies with respect to various sub-assemblies of the multi-axis positioning system 10'. Again the block representations of the sub-assemblies of the multi-axis positioning system 10' depicted in FIG. 40 are not intended to accurately represent each sub-assembly, they are intended for illustration of the function relationships of the various elements of the sub-assemblies and components of the multi-axis positioning system 10' shown. The representation of the multi-axis positioning system 10' in FIG. 40 includes the x-y stage assembly 12', the bottom plate assembly 40', a top plate assembly 42, piezoelectric motor assemblies 136, θ motor assemblies 58, and three Z motor assemblies 144. Also represented are a flexure assembly 44 and a precision bearing assembly 74.

Three Z axis encoder assemblies 67 are disposed and operatively coupled between the x-y stage assembly 12' and the top plate assembly 42 as represented in FIG. 40. The three Z axis encoder assemblies 67 include three Z encoder post assemblies 68 which are each rigidly secured to the x-y stage assembly 12'. Each Z encoder post assembly 68 includes a Z encoder post 70 and a Z encoder reader 72. Each Z axis encoder assembly 67 is configured to measure the Z axis 24 displacement of the top plate assembly 42 with respect to the x-y stage assembly 12' when each Z encoder reader 72 measures Z axis 24 position data from a respective Z encoder strip 194 which is rigidly secured to the top plate assembly 42. Three θ encoder assemblies 61 are disposed and operatively coupled between the x-y stage assembly 12' and the top plate assembly 42 as represented in FIG. 40. The three θ encoder assemblies 61 include three θ encoder post assemblies 62 which are each rigidly secured to the x-y stage assembly 12'. Each θ encoder post assembly 62 includes a θ encoder post 64 and a θ encoder reader 66. Each θ axis encoder assembly 61 is configured to measure the θ axis 26 displacement of the top plate assembly 42 with respect to the x-y stage assembly 12' when each θ encoder reader 66 measures θ axis 26 position data from a respective θ encoder strip 196 which is rigidly secured to the top plate assembly 42.

Figure 41:
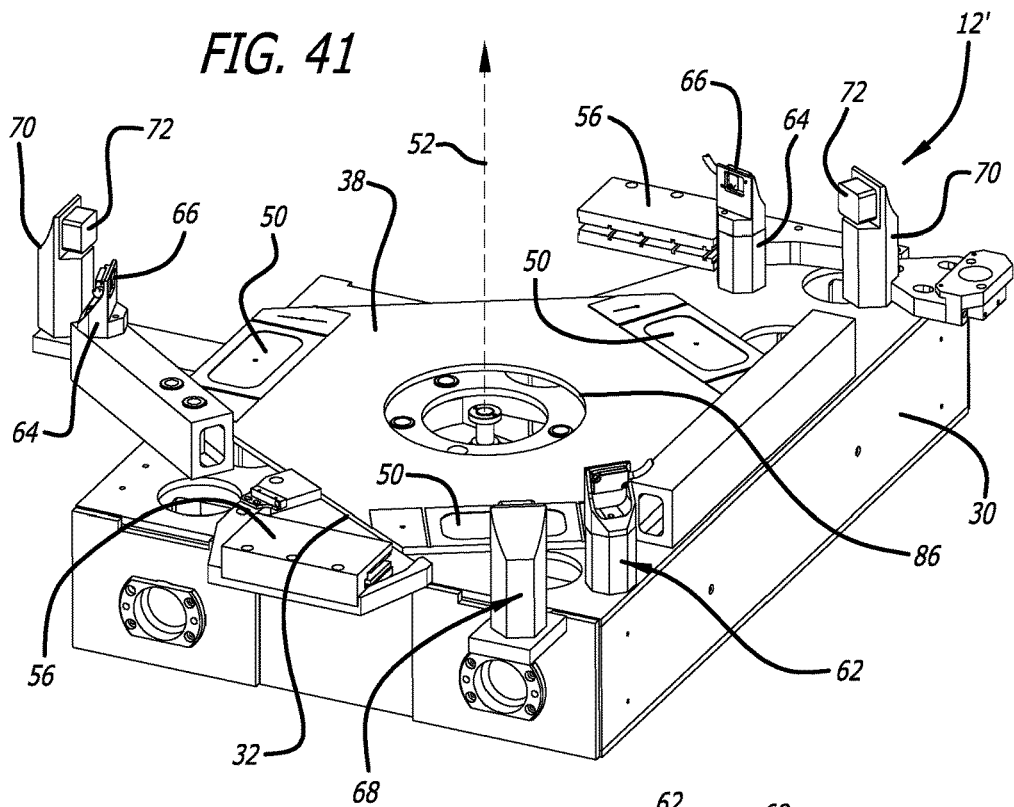
FIG. 41 is a perspective view of an X-Y stage assembly embodiment.
Figure 42:
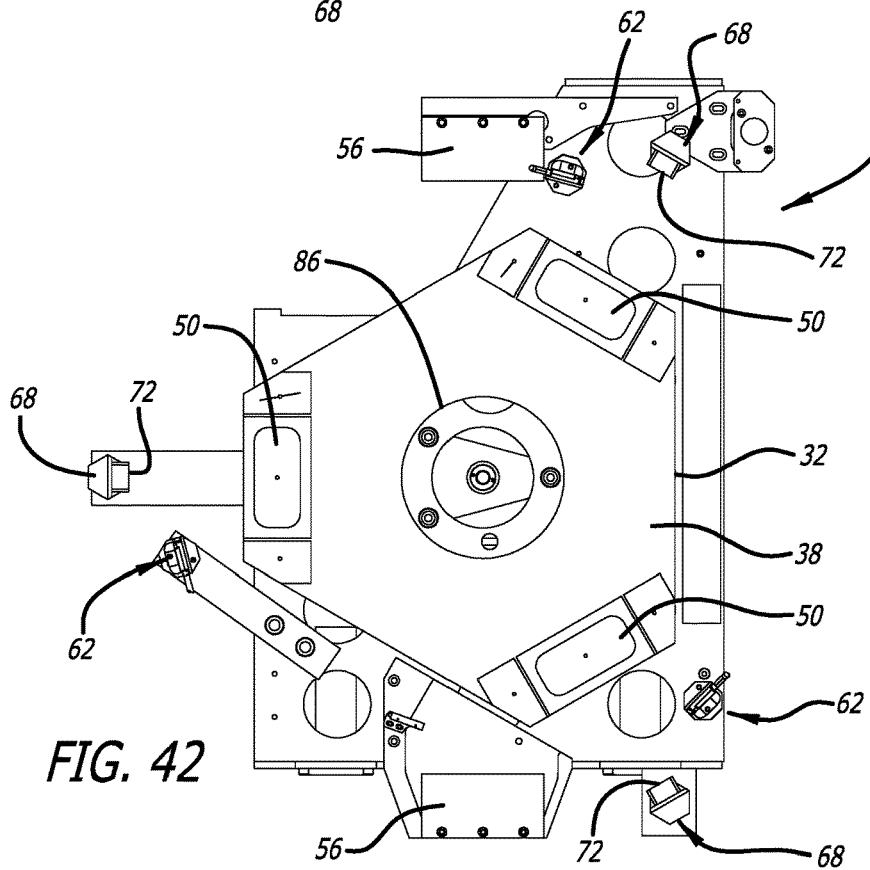
FIG. 42 is an elevation view of the X-Y stage embodiment of FIG. 41.

FIGS. 41 and 42 depict the x-y stage assembly 12'. The x-y stage assembly embodiment 12' is configured such that it is substantially equivalent to the XY stage embodiment 12 with the following exception. The x-y stage assembly 12' is configured with three Z encoder post assemblies 68. As shown in FIGS. 41 and 42, each Z encoder post assembly 68 may include a Z encoder post 70 and a Z encoder reader 72 which is disposed on a distal end of each Z encoder post 70. Each Z encoder post 70 may be rigidly secured to and extend from an upper surface 38 of the x-y stage 12' or some rigid extension member that extends from the upper stage. In some cases the each Z encoder post may be substantially perpendicular to the x-y stage 12' upper surface 38. The extension of the Z encoder posts 70 from the upper surface 38 may be configured to allow for the Z encoders 72 to be operatively coupled to the top plate assembly 42. The Z encoder post assemblies 68 may be radially spaced substantially radially equidistant from the central axis 52 of the x-y stage assembly 12', and the Z encoder post assemblies 68 may have an angular separation in the θ angular direction 26 of about 120 degrees. The Z encoder post assemblies 68 of the x-y stage assembly 12' are configured to measure displacement of the top plate assembly 42 along the Z axis 24.

Figure 43:
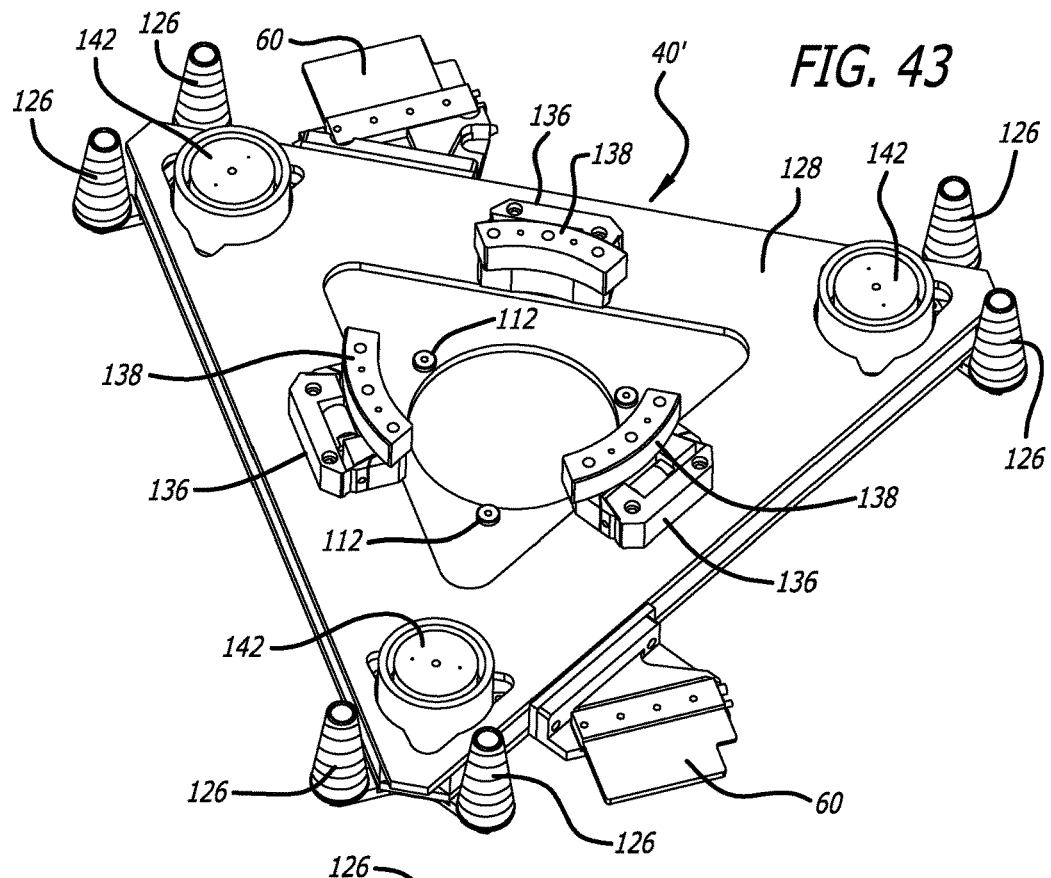
FIG. 43 is a perspective view of a bottom plate embodiment.
Figure 44:
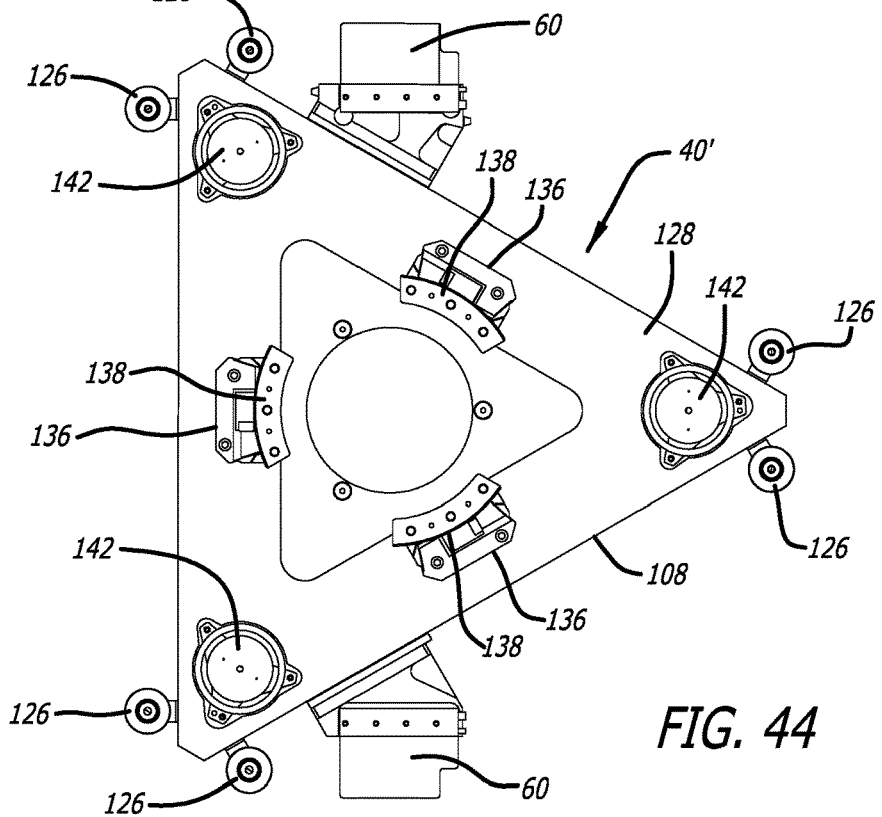
FIG. 44 is an elevation view of the bottom plate embodiment of FIG. 43.
Figure 45:
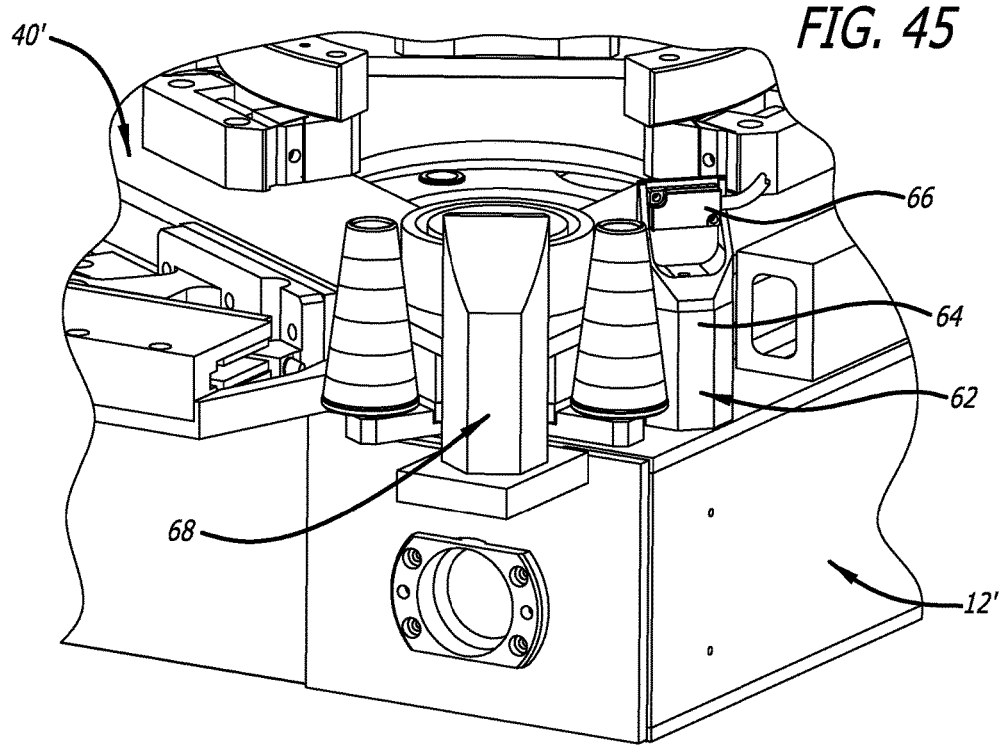
FIG. 45 is an enlarged view of the X-Y stage embodiment of FIG. 41.
Figure 46:
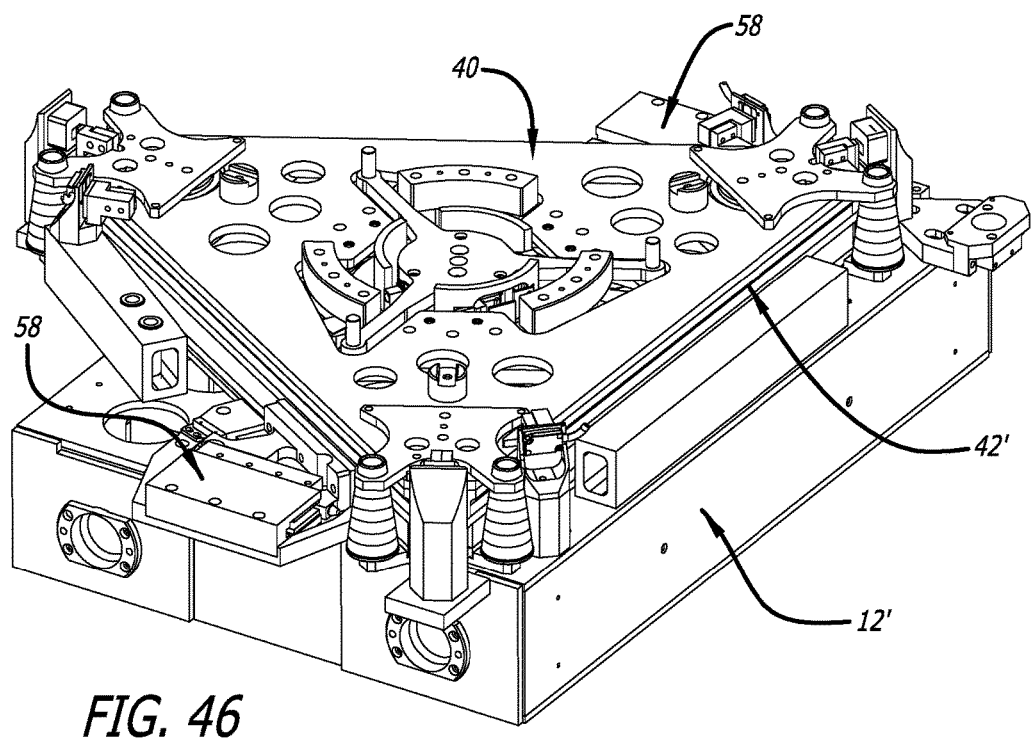
FIG. 46 depicts the top plate embodiment of FIG. 18, the precision bearing of FIG. 7, the lift pin ejector of FIG. 9, and the bottom plate of FIG. 43 coupled to the X-Y stage of FIG. 41.

FIGS. 43 and 44 depict an embodiment of a bottom plate assembly 40' which is substantially similar to the bottom plate assembly 40 which is depicted in FIGS. 12 and 13 with the exception that the bottom plate embodiment 40' does not incorporate any encoder assembly components. Thus the bottom plate assembly embodiment 40 which incorporates multiple Z encoder post assemblies 148 is meant to be coupled with x-y stage assembly 12 which incorporates no Z axis encoder components. Similarly, bottom plate assembly 40' which incorporates no Z axis encoders is meant to be coupled to x-y stage assembly 12' which incorporates multiple Z encoder post assemblies 68. FIG. 45 is an enlarged view of FIG. 37 (with the chuck assembly 46 hidden) depicting the bottom plate assembly embodiment 40' coupled to the x-y stage assembly 12' and showing the Z axis post assembly 68 (which is secured to the x-y stage assembly 12') θ encoder post assembly 62. FIG. 46 depicts the top plate assembly 42 coupled to the bottom plate assembly 40' which is in turn coupled to the x-y stage embodiment 12'. The upper plate assembly 42 is secured to the bottom plate assembly 42' by the flexure assembly 44 in a manner analogous to the embodiment shown in FIG. 33.

Figure 48:
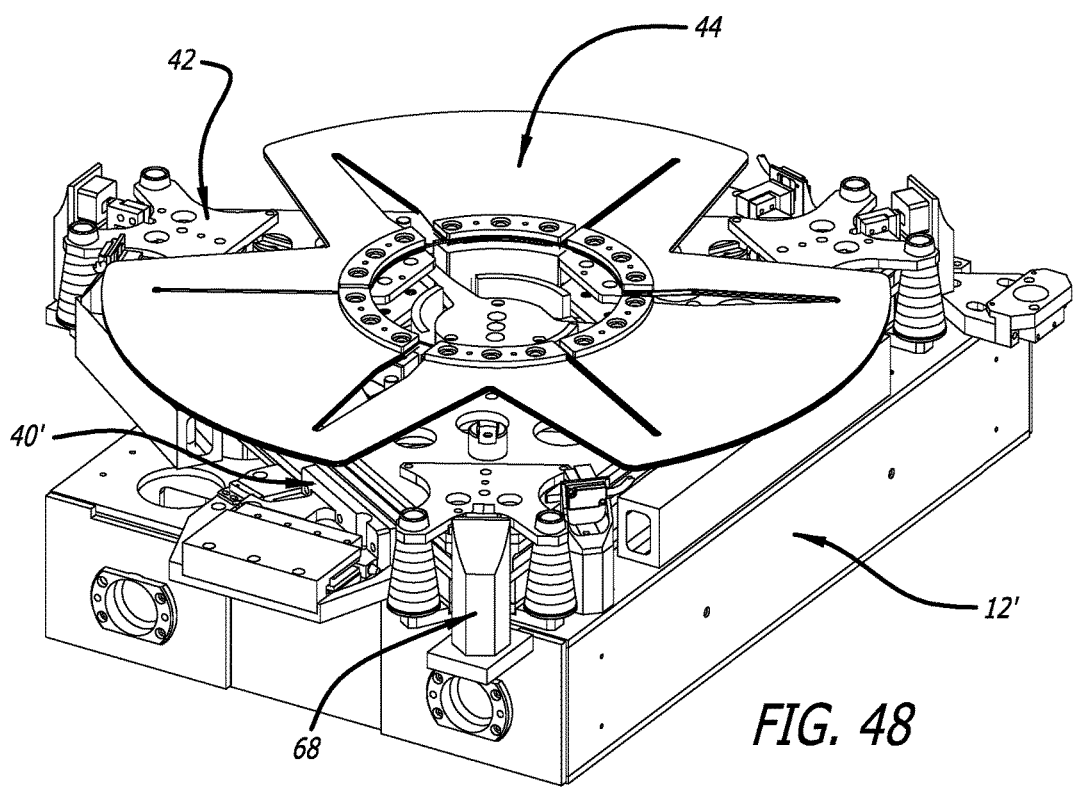
FIG. 48 depicts the flexure assembly of FIG. 31 coupled to the embodiments of FIG. 46.

FIG. 46 depicts the top plate assembly 42 coupled to the bottom plate assembly 40' which is in turn coupled to the x-y stage embodiment 12'. FIG. 47 depicts the Z encoder post assembly 68 (which is secured to the x-y stage 12') aligned with a respective Z encoder strip 194 of the top plate assembly 42. Each Z encoder strip 194 may be configured to have a scale pitch of about 5 μm to about 20 μm. FIG. 47 also depicts a θ encoder strip 196 of the top plate assembly 42 aligned with a θ encoder post assembly 62 which is secured to the x-y stage assembly 12'. Each θ encoder strip 196 may be configured to have a scale pitch of about 5 μm to about 20 μm. FIG. 48 depicts the flexure assembly 44 coupled to the embodiment of FIG. 46 wherein the Z encoder post assemblies 68 are disposed on the x-y stage 12'. The top plate assembly 42 is secured to the bottom plate assembly 42 by the slotted flexure assembly 44. The fully assembled multi-axis positioning system 10' is shown in FIG. 37 and includes the attached chuck assembly 44.

The remaining discussion applies to both the multi-axis positioning system embodiments 10 and the corresponding elements of the embodiment 10'. The top plate assembly 42 rotates with respect to the bottom plate assembly 40 when the top plate assembly 42 is powered by the piezoelectric motor assemblies 136 during the positioning of a specimen 220. The plurality of Z axis motor assemblies 144 which are operatively coupled between the top plate assembly 42 and the bottom plate assembly 40 may be configured to allow for relative rotation of the top plate assembly 42 with respect to the bottom plate assembly 40 in the θ angular direction 26. Specifically, the magnitude of the relative θ rotational displacement between the top plate assembly 42 and the bottom plate assembly 40 which is allowed by a θ direction clearance between the components of each Z axis motor assembly may be up to about 5 degrees. This means that each Z encoder strip 194 may be rotating in the θ angular direction 26 with respect to each Z axis post assembly 147 as each Z encoder reader 152 reads Z axis position data from its respective Z encoder strip 194. Therefore the Z encoder strips 194 must be configured such that they are sufficiently wide for the Z axis encoder readers 152 to still be able to read them while the Z encoder strips 194 are rotating in the θ angular direction 26 with respect to the Z encoder readers 152.

Figure 49:
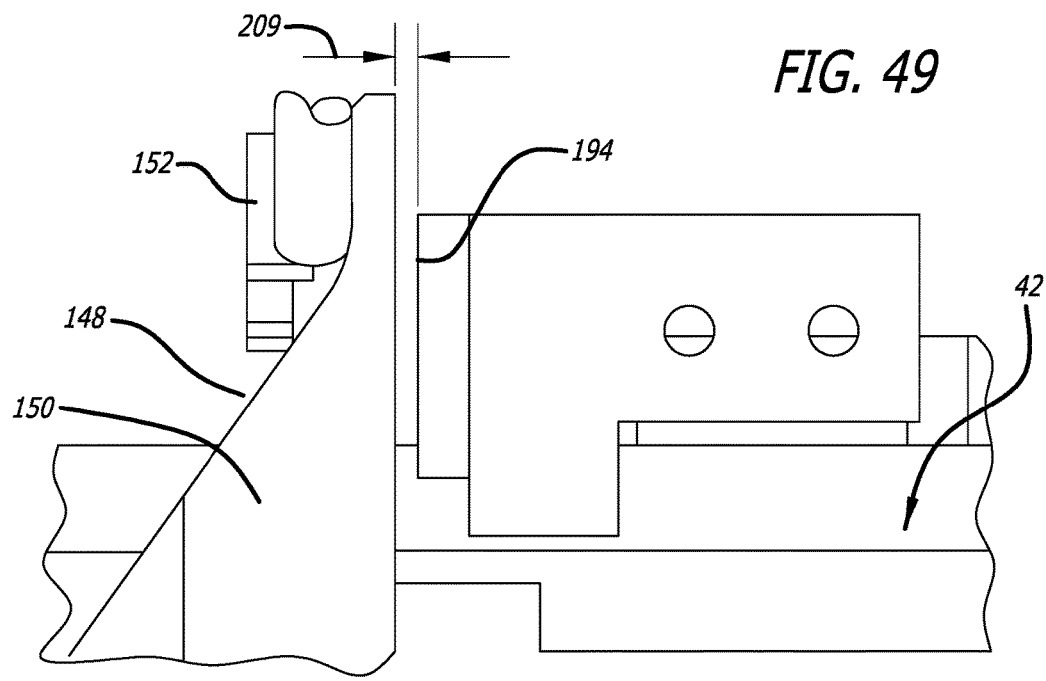
FIG. 49 is an enlarged view of FIG. 48 showing a Z axis encoder assembly including a Z encoder strip, a Z encoder, and a Z encoder post.

Similarly, each Z encoder strip 194 must be sufficiently separated from each respective Z encoder reader 152 in order to allow clearance for the rotation of the Z encoder strips 194 with respect to the Z encoder reader. A Z encoder reader 152, Z encoder post assembly 148, and a Z encoder strip 194 are shown in FIG. 49 along with a gap 209 which is disposed between the Z encoder strip 194 and the Z encoder reader 152. The gap 209 between the Z encoder strip 194 and the Z encoder reader 152 may need to be large enough in some cases to allow for θ axis 26 rotational motion of the Z encoder strip 194 with respect to the Z encoder reader 152 without interference between the two components. Similarly, the gap 209 may need to be large enough to allow for Z axis 24 translational motion of the Z encoder strip 194 with respect to the Z encoder reader 152 without interference between the two components. The three Z axis encoder assemblies 147 may be configured to measure displacement of the Z encoder reader 152 at a gap 209 (separation) of up to about 5 mm from the Z encoder strips 194. Similarly, the three θ encoder readers 66 of the θ encoder assemblies 61 and the three θ encoder strips 196 may be separated by a gap which is analogous to the gap 209. The three θ encoder readers 66 may be configured to accurately function and measure displacement at a gap 209 (separation) of up to about 5 mm from the θ encoder strips 196.

As has been discussed previously, the controller system 28 of the multi-axis positioning system 10 may be operatively coupled to the various motors and the encoders by any suitable means such as conductive wires, fiber optic cable, wireless transmission or the like. The controller system 28 may be used to activate any combination of motors or actuators of the multi-axis positioning system in order to translate and/or rotate the chuck assembly 46 along/about the desired axes relative to a reference surface upon which the multi-axis positioning system 10 is secured. The controller system 28 may also be used to measure the magnitude of the translational and/or rotational motion of the chuck assembly 46 using measurements from any single encoder or combination of encoders of the multi-axis positioning system 10. The position data acquired from one or more of the various encoders may also be recorded or stored in a memory device. The controller system 28 of the multi-axis positioning system 10 may include a processor and at least one memory device. The processor may be configured to read processor instructions which are stored on the memory device and then perform activities based on those instructions. For example the processor may follow processor instructions which are read from the memory device, and which instruct the processor to process position data from the encoder assemblies and then to actuate the motors of the multi-axis positioning system 10 to position the top plate assembly 42 in a desired position. The processor instructions may be configured to operate a closed loop position control algorithm.

The three θ encoder readers 62 each read position data from their respective θ encoder strips 196, with the position data from each θ encoder reader 62 indicating an angular position (about the θ axis 26) of the top plate assembly 42 with respect to the x-y stage assembly 12. Thus, three sets of θ angular position datum for the top plate assembly 42 with respect to the x-y stage assembly 12 may be communicated to the controller system 28 by each of the three θ encoder assemblies 62 at any given instant. The three sets of θ angular position data for the top plate assembly 42 with respect to the x-y stage assembly 12 may be suitably averaged by the controller system 28 in order to obtain an average θ angular position datum for the top plate assembly 42. The processor of the controller system 28 may follow a suitable averaging algorithm in order to average the angular position data which may be stored in the system memory or processed in real time.

Figure 50:
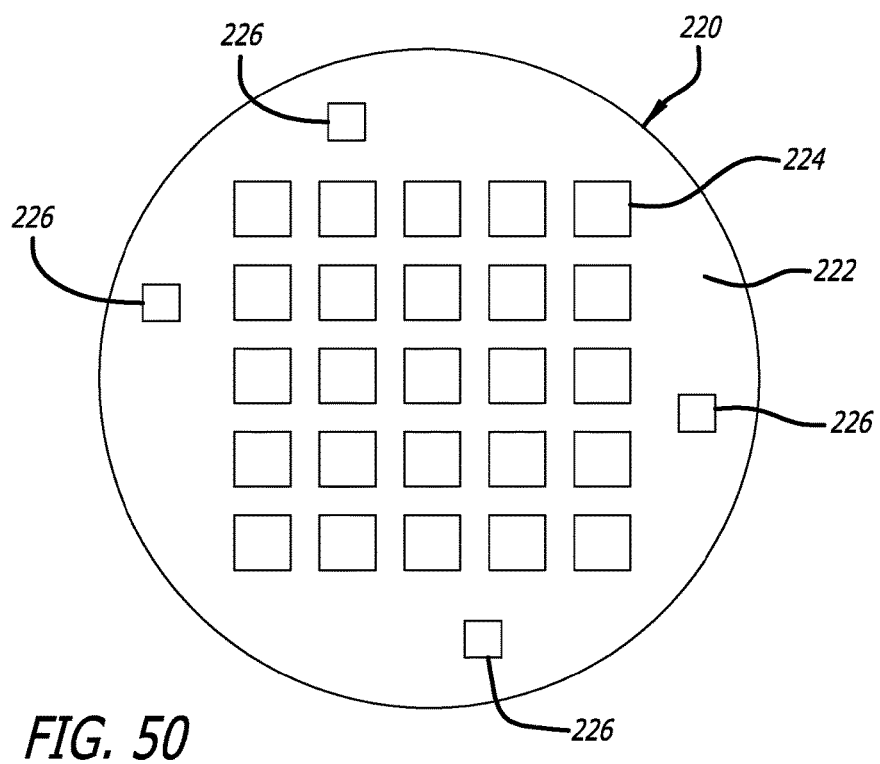
FIG. 50 is an elevation view of a silicon wafer specimen.

The multi axis position system may be used in order to inspect a specimen 220 which may include semiconductor based wafer chips, micro-electrical elements such as processor chips, LED's, and the like. A typical semi-conductor wafer specimen 220 is depicted in FIG. 50. The specimen 220 may generally be configured as a cylindrical disk and may include a variety of surface features which are disposed on a specimen upper surface 222 such as an array of micro electrical elements 224, multiple specimen test features 226, and the like. The test features 226 of the specimen 220 may be used by an optical inspection system 210 (see FIG. 51) in order to properly position the specimen 220 using the multi-axis positioning system 10 of the optical inspection system 210 during the inspection or other processing of the specimen 220.

Figure 51:
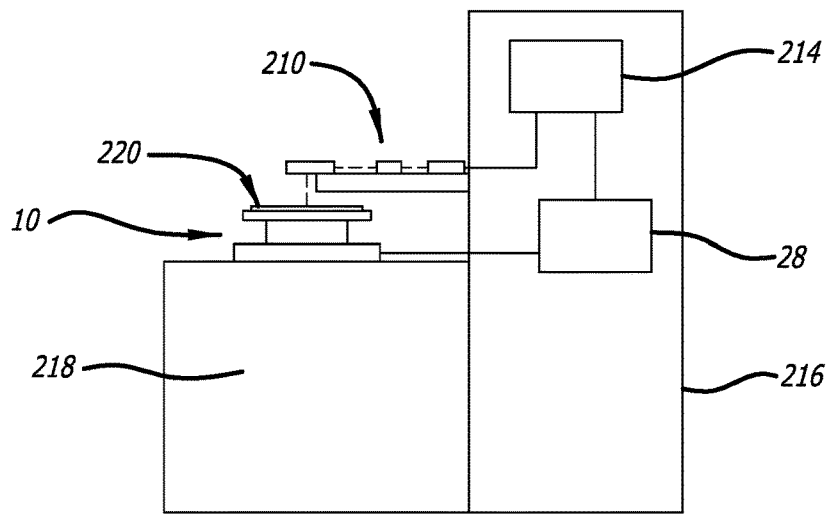
FIG. 51 is a schematic elevation view of an optical inspection system assembly.

The controller system 28 may optionally be used in conjunction with any suitable external controller system for the purposes of inspecting or processing specimens. For example the controller system 28 of the multi-axis positioning system 10 may be used in conjunction with an inspection tool controller 214 of an optical inspection system 210 which is depicted in FIG. 51. The optical inspection system 20 may include (but is not limited to) a multi-axis positioning system 10, a light source (not shown), an optical objective 212, and a detector assembly (not shown). The optical inspection tool may further include an optical train (not shown) which optically couples light source, the optical objective, and the detector assembly. When used in conjunction with the optical objective 212, the detector assembly can be used to determine Z axis 24 position data from a specimen 220 which is secured to the chuck assembly 46 of the multi-axis positioning system 10. The optical inspection system 210 shown includes the inspection tool controller 214 which may be configured to process optical information which is received by the detector assembly. The inspection tool controller 214 may be in operative communication with the controller system 28 of the multi-axis positioning system 10. The components of the optical inspection system 210 may be suitably disposed in a optical housing assembly 216 which may include an optical support 218 which may be used to hold the multi-axis positioning system 10 as shown in FIG. 51.

Figure 52:
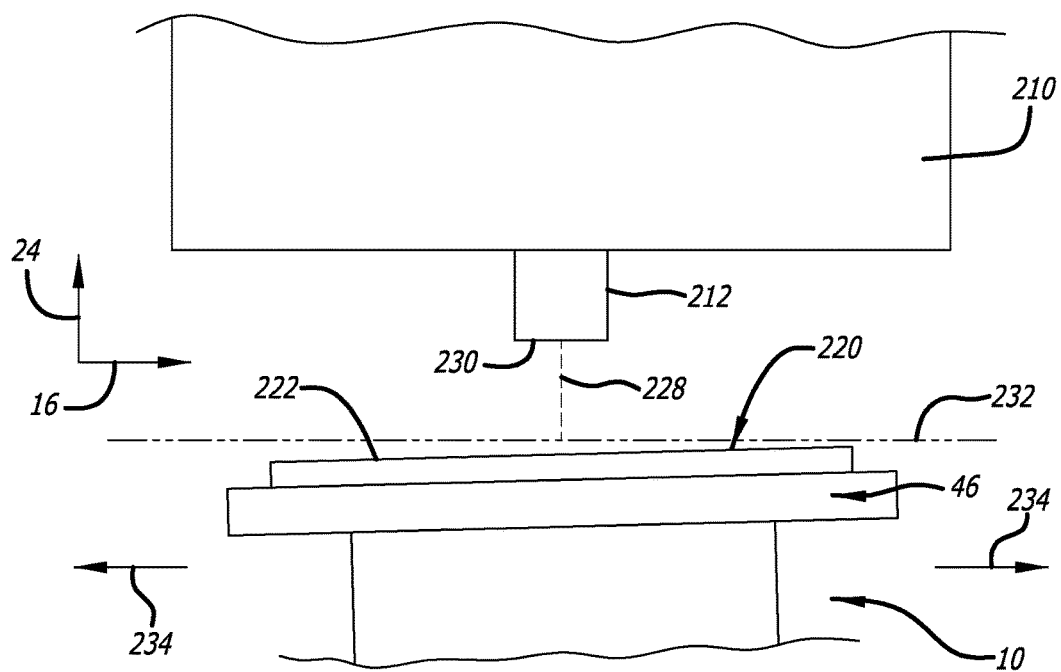
FIGS. 52 and 53 are enlarged views of the optical inspection system embodiment of FIG. 51.
Figure 53:
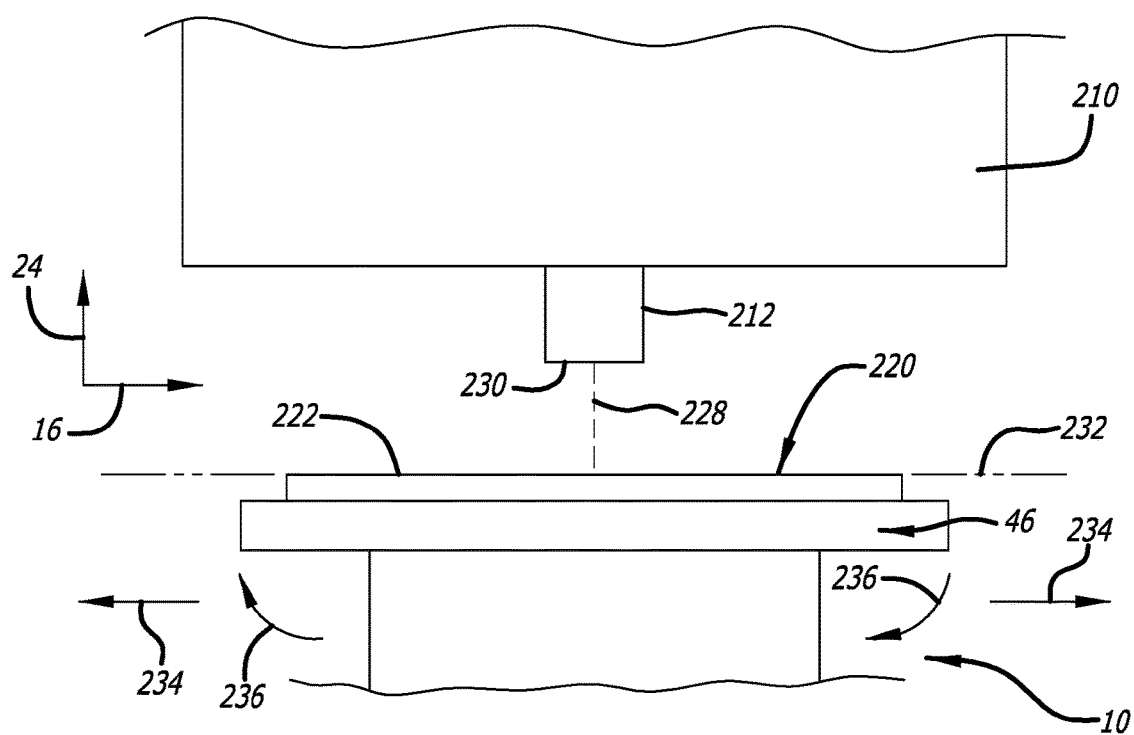

The optical inspection system 210 may be used in order to inspect the specimen 220 for flaws or defects by loading the specimen 220 onto the chuck assembly 46 of the multi-axis positioning system 10 as shown in FIG. 52. The optical inspection system 210 may also be configured to measure a position of one or more of the test features 226 which are disposed on the specimen 220 to in order to generate test feature position data. The test feature position data may include Z axis 24 position data of the test features 226 which are disposed on the specimen 220 upper surface 222 along an optical axis 228 of the optical objective 212 of the optical inspection system 210. The optical axis 228 of the optical objective 212 represents a theoretical axis which extends from the optical objective 212 such that it is substantially perpendicular to an optical surface 230 of the optical objective 212 (as shown in FIGS. 52 and 53). During the inspection process, it may be desirable to orient the upper surface 222 of the specimen 220 such that it is parallel to an optical plane 232 which is perpendicular to the optical axis 228, with all points of the optical plane 232 being substantially equidistant from the optical surface 230 of the optical objective 212. The multi-axis positioning system 10 may translate the specimen 220 (as indicated by arrows 234) with respect to the optical objective 212 along the X axis 18 or along the Y axis 20 (not shown, into and out of the page in FIGS. 52 and 53). In addition, the multi-axis positioning system 10 may rotate the specimen (as indicated by arrows 236 in FIG. 53) about the Tip axis 22, the Tilt axis 18, and the θ axis 26 with respect to the optical objective 212. Thus the controller system 28 of the multi axis position system 10 may be instructed by the inspection tool controller 214 (which is receiving test feature position data from the optical objective 212) to translate the specimen 220 along the X axis 16 and/or the Y axis 18 as the test feature position data is measured by the optical objective 212.

The test feature position data may then be stored in a memory storage device of the inspection tool controller 214. The inspection tool controller 214 may then generate a look up chart of a surface orientation of the specimen 220 from the test feature position data which was measured by the optical objective 212 and then stored in the memory storage device. The inspection tool controller 214 may then proceed with the inspection process by instructing the multi-axis positioning system 10 to translate the specimen 220 relative to the optical objective 212 in the plane 232 along the X axis 16 and the Y axis 18 in order to inspect features of the specimen 220 such as multiple micro electrical elements 224. While the specimen 220 is being translated along the X axis 16 and/or the Y axis 18 to inspect features such as the micro electrical elements 224 (as indicated by arrows 234 in FIG. 53), the multi-axis positioning system 10 is being instructed by the inspection tool controller 214 (which is reading test feature position data from the lookup chart) to orient the upper surface 222 of the specimen 220 such that it is parallel to the optical plane 232 (as shown in FIG. 53). The inspection tool controller 214 accomplishes this by comparing test feedback data from the lookup chart to θ position data feedback from the multiple θ encoder assemblies 62 of the multi-axis positioning system 10 (the position data feedback being fed to the inspection tool controller from the controller system) in order to orient the upper surface 222 of the specimen 220 such that it is parallel to the optical plane 232. Similarly, the inspection tool controller 214 compares test feedback data from the lookup chart to Z position data feedback from the multiple Z axis encoder assemblies 147 of the multi-axis positioning system 10 (the position data feedback being fed to the inspection tool controller from the controller system) in to orient the upper surface 222 of the specimen 220 such that it is parallel to the optical plane 232. Maintaining the upper surface 222 of the specimen 220 parallel to the optical plane 232 is equivalent to ensuring that the upper surface 222 remains perpendicular to the optical axis 228, and that the upper surface 222 of the specimen 220 remains at a constant distance from the optical objective 212. The inspection procedure which has just been discussed can also analogously be used for the fabrication of specimens with any suitable fabrication equipment which is used in conjunction with the multi-axis positioning system.

Look up charts can also be used to correct for known anomalies in the translation path of components such as the x-y stage assembly 12. In addition, the Z axis separation between the objective 212 and the specimen 220 may be maintained by the multi-axis positioning system 10 based on optical focus feedback from the inspection tool controller 214 communicated to the controller system 28.

With regard to the above detailed description, like reference numerals used therein may refer to like elements that may have the same or similar dimensions, materials and configurations. While particular forms of embodiments have been illustrated and described, it will be apparent that various modifications can be made without departing from the spirit and scope of the embodiments discussed. Accordingly, it is not intended that the invention be limited by the forgoing detailed description.

The entirety of each patent, patent application, publication and document referenced herein is hereby incorporated by reference. Citation of the above patents, patent applications, publications and documents is not an admission that any of the foregoing is pertinent prior art, nor does it constitute any admission as to the contents or date of these documents.

Modifications may be made to the foregoing embodiments without departing from the basic aspects of the technology. Although the technology may have been described in substantial detail with reference to one or more specific embodiments, changes may be made to the embodiments specifically disclosed in this application, yet these modifications and improvements are within the scope and spirit of the technology. The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" may refer to one of or a plurality of the elements it modifies (e.g., "a reagent" can mean one or more reagents) unless it is contextually clear either one of the elements or more than one of the elements is described. Although the present technology has been specifically disclosed by representative embodiments and optional features, modification and variation of the concepts herein disclosed may be made, and such modifications and variations may be considered within the scope of this technology.

Certain embodiments of the technology are set forth in the claim(s) that follow(s).

What is claimed is:

1. A multi-axis positioning system, comprising:
a translation stage configured to provide displacement in two dimensions between a base and an upper stage of the translation stage;
a bottom plate rotatably coupled to the translation stage such that an axis of rotation of the bottom plate in a θ rotation direction is perpendicular to a plane defined by the two dimensions of displacement of the translation stage;
at least one bottom plate motor operatively coupled between the bottom plate and the translation stage, the at least one bottom plate motor being configured to rotate the bottom plate assembly in the θ rotation direction relative to the translation stage;

a top plate operatively coupled to the bottom plate with at least three Z axis motors disposed and operatively coupled between corresponding outer portions of the bottom plate and respective outer portions of the top plate and which are configured to generate displacement between the respective outer portions of the bottom plate and top plate in a Z axis direction substantially parallel to the axis of rotation of the bottom plate;

a chuck configured to releasably secure a specimen secured to the top plate;

at least three Z axis position sensors which are disposed and operatively coupled between the upper stage of the translation stage and the top plate and which are configured to measure relative displacement in the Z axis direction between the upper stage and the top plate;

at least three θ position sensors which are operatively coupled between the upper stage of the translation stage and the top plate and which are configured to measure relative angular displacement in the θ rotation direction between the upper stage and the top plate; and a controller which is operatively coupled to the Z axis motors, the at least one bottom plate motor, the Z axis position sensors and the θ position sensors and which is configured to control actuation of the Z axis motors and at least one bottom plate motor.

2. The multi-axis positioning system of claim 1 wherein the three Z axis position sensors comprise optical encoder assemblies.

3. The multi-axis positioning system of claim 1 wherein the three θ position sensors comprise optical encoder assemblies.

4. The multi-axis positioning system of claim 1 wherein the at least three Z axis motors comprise voice coil motors.

5. The multi-axis positioning system of claim 1 wherein the bottom plate motor comprises a voice coil motor.

6. The multi-axis positioning system of claim 1 wherein the three Z axis motors are separated by an angular displacement about the axis of rotation of the bottom plate of about 120 degrees from each other.

7. The multi-axis positioning system of claim 6 wherein each of the three Z axis position sensors are disposed adjacent a corresponding Z axis motor.

8. The multi-axis positioning system of claim 6 wherein each of the three θ position sensors are disposed adjacent a corresponding Z axis motor.

9. An optical inspection system, comprising:
A. an optical inspection tool including a light source, an optical objective, a detector assembly, an optical train which optically couples the light source, optical objective and detector and an inspection tool controller that is configured to process optical information received by the detector assembly; and
B. a multi-axis positioning system, comprising:
a translation stage configured to provide displacement in two dimensions between a base and an upper stage of the translation stage;
a bottom plate rotatably coupled to the translation stage such that an axis of rotation of the bottom plate in a θ rotation direction is perpendicular to a plane defined by the two dimensions of displacement of the translation stage;
at least one bottom plate motor operatively coupled between the bottom plate and the translation stage, the at least one bottom plate motor being configured to rotate the bottom plate assembly in the θ rotation direction relative to the translation stage;

a top plate operatively coupled to the bottom plate with at least three Z axis motors disposed and operatively coupled between corresponding outer portions of the bottom plate and respective outer portions of the top plate and which are configured to generate displacement between the respective outer portions of the bottom plate and top plate in a Z axis direction substantially parallel to the axis of rotation of the bottom plate;

a chuck secured to the top plate which is configured to releasably secure a specimen thereto and which is disposed in communication with an optical path of the optical objective of the optical inspection tool;

at least three Z axis position sensors which are disposed and operatively coupled between the upper stage of the translation stage and the top plate and which are configured to measure relative displacement in the Z axis direction between the upper stage and the top plate;

at least three θ position sensors which are operatively coupled between the upper stage of the translation stage and the top plate and which are configured to measure relative angular displacement in the θ rotation direction between the upper stage and the top plate; and a positioning system controller which is operatively coupled to the Z axis motors, the at least one bottom plate motor, the Z axis position sensors and the θ position sensors and which is configured to control actuation of the Z axis motors and at least one bottom plate motor.

10. The inspection system of claim 9 wherein the three Z axis position sensors comprise optical encoder assemblies.

11. The inspection system of claim 9 wherein the three θ position sensors comprise optical encoder assemblies.

12. The inspection system of claim 9 wherein the at least three Z axis motors comprise voice coil motors.

13. The inspection system of claim 9 wherein the bottom plate motor comprises a voice coil motor.

14. The inspection system of claim 9 wherein the three Z axis motors are separated by an angular displacement about the axis of rotation of the bottom plate of about 120 degrees from each other.

15. The inspection system of claim 14 wherein each of the three Z axis position sensors are disposed adjacent a corresponding Z axis motor.

16. The inspection system of claim 14 wherein each of the three θ position sensors are disposed adjacent a corresponding Z axis motor.

17. The inspection system of claim 9 wherein the inspection tool controller is operatively coupled to the positioning system controller and configured to transmit Z axis position data of the chuck from the optical objective to the positioning system controller.

18. A method of inspecting a specimen, comprising:
loading the specimen into a chuck of a multi-axis positioning system, the multi-axis positioning system including a translation stage, a bottom plate rotatably coupled to the translation stage, a top plate operatively coupled to the bottom plate such that the top plate may be displaced relative to the bottom plate along a Z axis, a tip axis, a tilt axis and along a θ rotation direction, and the chuck being secured to the top plate;
measuring a position of one or more test features disposed on the specimen to generate test feature position data, the test feature position data including a Z axis position of the one or more test features along an optical axis of an objective of an optical inspection tool;

storing the test feature position data in a memory storage device;

generating a look up chart of a surface orientation of the specimen from the test feature position data; and translating the specimen relative to the objective in an x-y plane perpendicular to the optical axis of the objective while positioning the specimen with the multi-axis positioning system according to the look up chart using theta position data feedback from a plurality of θ position sensors disposed and operatively coupled between the translation stage and top plate of the multi-axis positioning system and using Z axis position feedback from a plurality of Z axis position sensors disposed and operatively coupled between the translation stage and top plate of the multi-axis positioning system, the specimen being translated such that an upper surface of the specimen remains perpendicular to an optical axis of the objective and the upper surface of the specimen remains at a constant distance from the objective.

19. A method of inspecting a specimen, comprising:

loading the specimen into a chuck of a multi-axis positioning system, the multi-axis positioning system including a translation stage, a bottom plate rotatably coupled to the translation stage, a top plate operatively coupled to the bottom plate such that the top plate may be displaced relative to the bottom plate along a Z axis, a tip axis, a tilt axis and along a θ rotation direction, and the chuck being secured to the top plate;

translating the specimen relative to an optical inspection tool while positioning the specimen with the multi-axis positioning system using theta position data feedback from a plurality of θ position sensors disposed and operatively coupled between the translation stage and top plate of the multi-axis positioning system and using Z axis position feedback from a plurality of Z axis position sensors disposed and operatively coupled between the translation stage and top plate of the multi-axis positioning system, wherein translating the specimen comprises translating the specimen such that an upper surface of the specimen remains perpendicular to an optical axis of an objective of an optical inspection tool and the upper surface of the specimen remains at a constant distance from the objective along an optical axis of the objective; and transmitting Z axis position data of the specimen from an inspection tool controller of the inspection tool to a positioning system controller of the multi-axis positioning system.

* * * * *